(12) United States Patent
Ganesh et al.

(10) Patent No.: US 12,240,829 B2
(45) Date of Patent: Mar. 4, 2025

(54) PROSTAGLANDIN RECEPTOR EP2 ANTAGONISTS, DERIVATIVES, AND USES RELATED THERETO

(71) Applicant: Emory University, Atlanta, GA (US)

(72) Inventors: Thota Ganesh, Atlanta, GA (US); Raymond J. Dingledine, Atlanta, GA (US); Radhika Amaradahi, Atlanta, GA (US); Shabber Mohammed, Atlanta, GA (US)

(73) Assignee: Emory University, Atlanta, GA (US)

( * ) Notice: Subject to any disclaimer, the term of this patent is extended or adjusted under 35 U.S.C. 154(b) by 789 days.

(21) Appl. No.: 17/440,437

(22) PCT Filed: Mar. 19, 2020

(86) PCT No.: PCT/US2020/023659
§ 371 (c)(1),
(2) Date: Sep. 17, 2021

(87) PCT Pub. No.: WO2020/191208
PCT Pub. Date: Sep. 24, 2020

(65) Prior Publication Data
US 2022/0162186 A1    May 26, 2022

Related U.S. Application Data

(60) Provisional application No. 62/821,163, filed on Mar. 20, 2019.

(51) Int. Cl.
*C07D 401/14* (2006.01)
*A61P 35/00* (2006.01)
*C07D 403/12* (2006.01)

(52) U.S. Cl.
CPC ............ *C07D 401/14* (2013.01); *A61P 35/00* (2018.01); *C07D 403/12* (2013.01)

(58) Field of Classification Search
CPC ........................... C07D 401/14; C07D 403/12
See application file for complete search history.

(56) References Cited

U.S. PATENT DOCUMENTS

| | | |
|---|---|---|
| 5,342,851 A | 8/1994 | Sanfilippo |
| 9,518,044 B2 | 12/2016 | Jiang |
| 10,040,783 B2 | 8/2018 | Jiang |
| 10,052,332 B2 | 8/2018 | Ganesh |
| 10,568,889 B2 | 2/2020 | Ganesh |
| 11,077,120 B2 | 8/2021 | Ganesh et al. |
| 2005/0277773 A1 | 12/2005 | Kataoka |
| 2009/0023741 A1 | 1/2009 | Buchmann |
| 2009/0163545 A1 | 6/2009 | Goldfarb |
| 2017/0081314 A1 | 3/2017 | Jiang |
| 2020/0085837 A1 | 3/2020 | Ganesh |
| 2022/0000883 A1 | 1/2022 | Ganesh |
| 2022/0162186 A1 | 5/2022 | Ganesh |

FOREIGN PATENT DOCUMENTS

| | | |
|---|---|---|
| CN | 01157668 | 4/2008 |
| EP | 2002838 | 12/2008 |
| EP | 2014287 | 1/2009 |
| EP | 2476667 | 7/2012 |
| JP | 2008115088 | 5/2008 |
| WO | 1999031064 | 6/1999 |
| WO | 2004035525 | 4/2004 |
| WO | 2008152097 | 12/2008 |
| WO | 2008152099 | 12/2008 |
| WO | 2009022104 | 2/2009 |
| WO | 2009147121 | 12/2009 |
| WO | 2010012396 | 2/2010 |
| WO | 2010012397 | 2/2010 |
| WO | 2010100606 | 9/2010 |
| WO | 2012080220 | 6/2012 |
| WO | 2012177618 | 12/2012 |
| WO | 2015167825 A1 | 11/2015 |

OTHER PUBLICATIONS

Amaradhi et al. Potent, Selective, Water Soluble, Brain-Permeable EP2 Receptor Antagonist for Use in Central Nervous System Disease Models, J. Med. Chem, 2020, 63, 1032-1050.

Amaradhi et al. Second-Generation Prostaglandin Receptor EP2 Antagonist, TG8-260, with High Potency, Selectivity, Oral Bioavailability, and Anti-Inflammatory Properties. ACS Pharmacol Transl Sci, 2022, 5, 118-133.

Baryawno et al. Tumor-growth—promoting cyclooxygenase-2 prostaglandin E2 pathway provides medulloblastoma therapeutic targets, Neuro-Oncology, 10, 661-674, 2008.

Battaglia et al. Indole amide derivatives: synthesis, structure—activity relationships and molecular modelling studies of a new series of histamine H1-receptor antagonists, Eur J Med Chem. 1999, 34(2) 93-105.

Chemical Abstracts, CAS Registry No. 749890-20-8, C18H16N6O, Benzamide, N-[2-(1H-indol-3-yl) ethyl]-4-(1H-tetrazol-1-yl)-, downloaded Feb. 21, 2019.

Fu et al. EP2 Receptor Signaling Regulates Microglia Death, Mol Pharmacol, 88: 161-170, 2015.

Ganesh et al. Development of second generation EP2 antagonists with high selectivity, Eur J Med Chem. 2014, 23, 82: 521-535.

(Continued)

*Primary Examiner* — Susanna Moore

(74) *Attorney, Agent, or Firm* — Emory Patent Group

(57) ABSTRACT

The disclosure relates to Prostnglandin receptor EP2 antagonists, derivatives, compositions, and methods related thereto. In certain embodiments, the disclosure relates to methods of treating or preventing conditions and diseases in which EP2 receptor activation has a physiological role, such as but not limited to, brain injury, inflammatory diseases, epilepsy, neuroinflammation after a seizure, pain, endometriosis, cancer, rheumatoid arthritis, skin inflammation, vascular inflammation, colitis, and neurological disorders by administering a pharmaceutical composition comprising a compound disclosed herein to a subject in need thereof.

2 Claims, 27 Drawing Sheets

(56) References Cited

OTHER PUBLICATIONS

Ganesh et al. Lead Optimization Studies of Cinnamic Amide EP2 Antagonists, J. Med. Chem., 2014, 57 (10), 4173-4184.
Ganesh et al. Peripherally Restricted, Highly Potent, Selective, Aqueous-Soluble EP2 Antagonist with Anti-Inflammatory Properties, Mol. Pharmaceutics, 2018, 15, 5809-5817.
Hou et al. Prostaglandin E2 in neuroblastoma: Targeting synthesis or signaling? Biomedicine & Pharmacotherapy 156 (2022) 113966.
Hou et al Targeting EP2 receptor with multifaceted mechanisms for high-risk neuroblastoma, 2022, Cell Reports 39, 111000, pp. 1-18 and e1-e5.
Jiang et al. Prostaglandin receptor EP2 in the crosshairs of anti-inflammation, anti-cancer, and neuroprotection, Trends in Pharmacological Sciences, 2013, vol. 34, No. 7, 413-420.
Jiang et al. Small molecule antagonist reveals seizure-induced mediation of neuronal injury by prostaglandin E2 receptor subtype EP2. Proc Natl Acad Sci U S A. 2012, 109(8):3149-54.
Jiang et al. Therapeutic window for cyclooxygenase-2 related anti-inflammatory therapy after status epilepticus, Neurobiology of Disease, 76 (2015) 126-136.
Legriel. et al. Functional outcome after convulsive status epilepticus, Crit Care Med, 2010, vol. 38, No. 12, 2295.
Liang et al. Deletion of the Prostaglandin E2 EP2 Receptor Reduces Oxidative Damage and Amyloid Burden in a Model of Alzheimer's Disease, The Journal of Neuroscience, 2005, 25(44): 10180-10187.
Qiu et al. Small-molecule inhibition of prostaglandin E receptor 2 impairs cyclooxygenase-associated malignant glioma growth, Br J Pharmacol. 2019, 176:1680-1699.
Rojas et al. Inhibition of the prostaglandin EP2 receptor is neuroprotective and accelerates functional recovery in a rat model of organophosphorus induced status epilepticus, Neuropharmacology. 2015, 93: 15-27.
Rojas et al.Inhibition of the prostaglandin E2 receptor EP2 prevents status epilepticus-induced deficits in the novel object recognition task in rats, Neuropharmacology 110 (2016) 419e430.
Shishido et al. Synthesis of benzamide derivatives as TRPV1 antagonists. Bioorganic & Medicinal Chemistry Letters 2007;18(3):1072-8.
Silva et al. Advances in prodrug design, Mini Rev Med Chem, 2005, 5(10):893-914.
Yang et al., Altered hippocampal long-term synaptic plasticity in mice deficient in the PGE2 EP2 receptor. J Neurochem 108:295-304 (2009).
Pubchem, Substance Record for SID 373402298. Available Date: May 25, 2018. [retrieved on May 4, 2020) Retrieved from the Internet: <URL: https://pubchem.ncbi.nlm.nih.gov/substance/373402298>. entire document.
Pubchem, Substance Record for SID 253164928. Available Date: Oct. 22, 2015. (retrieved on Jun. 23, 2020]. Retrieved from the Internet: <URL:https://pubchem .ncbi.nim .nih .gov/substance/253164928>. entire document.
International Search Report and Written Opinion issued in PCT/US2020/023659, mailed Jul. 17, 2020, 12 Pages.
Amaradhi Radhika et al: "Potent, Selective, Water Soluble, Brain-Permeable EP2 Receptor Antagonist for Use in Central Nervous System Disease Models", Journal of Medicinal Chemistry, vol. 63, No. 3, Jan. 6, 2020, pp. 1032-1050.
Extended European Search Report issued in EP20774593.6, mailed Oct. 25, 2022.
Battaglia et al. Indole amide derivatives: synthesis, structure—activity relationships and molecular modelling studies of a new series of histamine H1-receptor antagonists, Eur J Med Chem., vol. 34, Issue 2, Feb. 1999, pp. 93-105.
Fu et al. EP2 Receptor Signaling Regulates Microglia Death, Mol Pharmacol 88:161-170, Jul. 2015.
Ganesh et al. Development of second generation EP2 antagonists with high selectivity, Eur J Med Chem. Jul. 23, 2014; 82: 521-535.
Ganesh et al. Lead Optimization Studies of Cinnamic Amide EP2 Antagonists, J. Med. Chem., 2014,57 (10), pp. 4173-4184.
Ganesh, et al.., Peripherally restricted, highly potent, selective, aqueous-soluble EP2 antagonist with anti-inflammatory properties. Molecular pharmaceutics, 15(12), 2018, 5809-5817.
Rojas et al. Inhibition of the prostaglandin EP2 receptor is neuroprotective and accelerates functional recovery in a rat model of organophosphorus induced status epilepticus, Neuropharmacology. Jun. 2015 93: 15-27.
Silva, A., Mini-Reviews in Medicinal Chemistry, 2005, vol. 5, pp. 893-014.
Yang (2009) Altered hippocampal long-term synaptic plasticity in mice deficient in the PGE2 EP2 receptor. J Neurochem 108:295-304.
Shishido, Yuji, et al. "Synthesis of benzamide derivatives as TRPV1 antagonists." Bioorganic & medicinal chemistry letters 18.3 (2008): 1072-1078.
Database Registry Chem Abstract Service Ohio; database accession No. 749890-20-08, C18H16N6, Benzamide, Abstract.
Supplementary European Search Report issued for Application 15785214, dated Sep. 28, 2017.
Extended Supplementary European Search Report issued for Application No. 15785214, dated Oct. 10, 2018.
International Search Report and Written Opinion issued for Application No. PCT/US2015/026364, dated Nov. 5, 2015.
CAPLUS 2008:1508627.

| Compound | Structure | Compound | Structure |
|---|---|---|---|
| TG11-77.HCl |  | TG8-224 |  |
| TG11-163 |  | TG11-283. HCl |  |
| TG11-214 |  | | |
| TG11-199 |  | TG15-48 |  |
| TG11-215 |  | TG11-265 |  |
| TG11-275 |  | TG11-237 |  |
| TG15-03 |  | TG10-06 |  |
| TG15-40 |  | TG11-167 |  |
| | | TG11-169 |  |
| TG11-228 |  | TG11-163 |  |
| | | TG7-229 |  |
| TG8-242 |  | TG7-228 |  |

| Compound | EP2 $K_B$ (nM) | Solubility μM |
|---|---|---|
| TG11-77.HCl | 8.0 | 2520 (1.1 mg/mL) in water) |
| TG11-163 | 7.5 | ND |
| TG11-214 | 6.1 | |
| TG11-199 | 5.8 | >100 (SGF) |
| TG11-215 | 96 | 37 (SGF) |
| TG11-275 | 7.8 | ND |
| TG15-03 | 1225 | <10 |
| TG15-40 | 230 | ND |
| TG11-228 | 13.0 | ND |
| TG8-242 | 28.3 | ND |
| TG8-224 | 20 | >100 (SGF) |
| TG11-283. HCl | 1.7 | 2643 (1.2 mg/mL) in water |
| TG15-48 | 64.0 | 45 |
| TG11-265 | 10.7 | 27 |
| TG11-237 | 8.3 | 17 |
| TG10-06 | 1410 | 38 |
| TG11-167 | 22 | ND |
| TG11-169 | 22.1 | ND |
| TG11-163 | 7.5 | ND |
| TG7-229 | 19.5 | ND |
| TG7-228 | 1.6 | 70 |

FIG. 2B

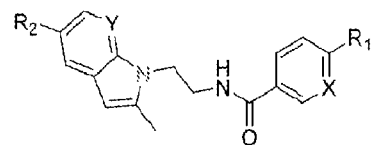

| Compd. ID | R₁ | R₂/X/Y | EP2 $K_B$ (nM) | DP1 $K_B$ (nM) | Aq. Sol.[b] (µM) |
|---|---|---|---|---|---|
| TG10-31 | piperidinyl | X=N, R₂=Y=H | 185 | ND | ND |
| TG10-44 | morpholinyl | Y=N, R₂=X=H | 2400 | ND | 302 |
| TG10-79 | -NHCSNHPh | R₂=X=Y=H | 55.8 | 240 | ND |
| TG10-104 | 4-oxopiperidinyl | R₂=X=Y=H | 83 | 4530 | ND |
| TG10-106 | 4-hydroxy-4-ethylpiperidinyl | R₂=X=Y=H | 48 | 2215 | ND |
| TG10-107 | -NHCONHPh | R₂=X=Y=H | 6.6 | 900 | ND |
| TG10-113 | morpholinyl | R₂=F, X=Y=H | 32.6 | 1340 | ND |
| TG10-114 | imidazolyl | R₂=F, X=Y=H | 62 | 935 | ND |
| TG10-118 | 4-(hydroxyimino)piperidinyl | R₂=X=Y=H | 14.5 | ND | ND |
| TG10-127 | pyrazolyl | R₂=F, X=Y=H | 13.4 | 841 | ND |
| TG10-130 | -NHCOPh(4-F) | R₂=X=Y=H | 21.3 | 8025 | ND |
| TG10-135 | -NHC(O)-C₆H₄-pyridyl | R₂=X=Y=H | 12.8 | 32240 | 75 (SGF) |
| Compd. ID | R₁ | R₂/X/Y | EP2 $K_B$ (nM) | DP1 $K_B$ (nM) | Aq. Sol.[b] (µM) |
| TG12-68 | pyrimidinyl-NHAc | R₂=X=Y=H | 26.8 | >3000 | ND |
| TG10-168 | pyrimidinyl-NH₂ | R₂=X=Y=H | 1.0 | 560 | 70 |

FIG. 6A

| Compd. ID | R₁ | R₂/X/Y | EP2 $K_B$ (nM) | DP1 $K_B$ (nM) | Aq. Sol.[b] (μM) |
|---|---|---|---|---|---|
| TG10-30 | piperidinyl | X=N, R₂=Y=H | 185 | ND | ND |
| TG10-33 | morpholinyl | R₂=Br, X=Y=H | 350 | ND | ND |
| TG10-38 | morpholinyl | R₂=3-pyridyl, X=Y=H | 1710 | ND | ND |
| TG10-40 | morpholinyl | R₂=Ph(2F), X=Y=H | 2170 | ND | ND |
| TG10-51 | NH-Ph | Y=N, R₂=X=H | 440 | ND | ND |
| TG10-57 | morpholinyl | R₂=Cl, X=Y=H | 230 | ND | ND |
| TG10-58 | morpholinyl | R₂=F, X=Y=H | 161 | ND | ND |
| TG10-59 | morpholinyl | R₂=F, X=N, Y=H | 392 | ND | ND |
| TG10-60 | imidazolyl | R₂=F, X=N, Y=H | 168 | ND | ND |

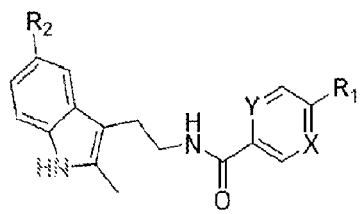

| | | | | | |
|---|---|---|---|---|---|
| TG10-71 | ⸺NH-Ph | R₂=X=Y= H | 4.7 | ND | 10 |
| TG10-74 | N-piperidin-4-one | R₂=X=Y= H | 220 | ND | ND |
| TG10-175 | 2-aminopyrimidin-4-yl | R₂=X=Y= H | 51.4 | 2160 | 75 |
| TG10-108 | -NHCOPh | R₂=X=Y= H | 5.5 | 440 | ND |
| TG10-110B | ⸺NH-(3-F-C₆H₄) | R₂=X=Y= H | 21.3 | 690 | ND |
| TG10-136 | 4-(pyridin-4-yl)benzamide | R₂=X=Y= H | 2.15 | 1956 | ND |
| TG10-202 | 2-chloropyrimidin-5-yl | R₂=X=Y= H | 29 | ND | ND |
| TG10-211 | 2-morpholinopyrimidin-5-yl | R₂=X=Y= H | 39.5 | ND | ND |
| TG10-214 | 2-(3-methoxypropylamino)pyrimidin-5-yl | R₂=X=Y= H | 19.5 | 1175 | 25 |
| TG10-218 | -B(OH)₂ | R₂=X=Y= H | 291 | ND | ND |
| TG10-219 | 4-methoxyphenyl | R₂=X=Y= H | 3.3 | 440 | ND |
| TG10-220 | 2-methoxypyrimidin-5-yl | R₂=X=Y= H | 43 | 1660 | ND |
| TG10-224 | 2-(trifluoromethyl)pyridin-5-yl | R₂=X=Y= H | 188 | ND | ND |
| TG10-227 | 4-(hydroxymethyl)-1H-pyrazol-1-yl | R₂=X=Y= H | 84.2 | ND | ND |

FIG. 6C

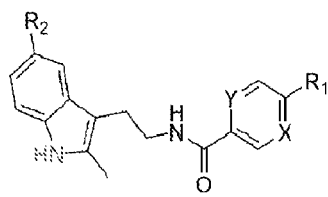

| Compound | R group | Substituents | | | |
|---|---|---|---|---|---|
| TG10-228 | triazole-C(CH3)2OH | R2=X=Y=H | 21.4 | 125000 | >100 |
| TG10-230 | pyridin-2(1H)-one | R2=X=Y=H | 137 | ND | ND |
| TG10-231 | pyrimidin-2(1H)-one | R2=X=Y=H | 322 | ND | ND |
| TG10-233 | indole | R2=X=Y=H | 0.5 | 117 | ND |
| TG10-239 | isoquinolin-1(2H)-one | R2=X=Y=H | 0.6 | 186 | 12 |
| TG10-240 | 3-hydroxyquinoline | R2=X=Y=H | 4.2 | 582 | 25 |
| TG10-250 | 4-chloroimidazole | R2=X=Y=H | 68 | 24390 | ND |
| TG10-251 | 4-chloropyrazole | R2=X=Y=H | 34 | 4460 | 18 |
| TG10-282 | 2-aminopyrimidine | X=N, R2=Y=H | 38 | ND | 204 |
| TG10-284 | N-methylimidazole | R2=X=Y=H | 90 | ND | ND |
| TG10-287 | pyrazole-C(CH3)2NH2 | R2=X=Y=H | 614 | ND | ND |
| TG10-293 | imidazole | R2=X=Y=H | 58 | ND | ND |
| TG12-18 | 4-methylimidazole | R2=X=Y=H | 72 | ND | ND |
| TG12-21 | indoline | R2=X=Y=H | 0.6 | ND | ND |

FIG. 6D

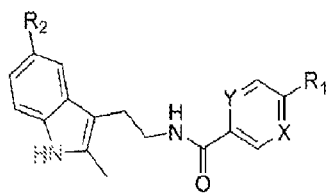

| | | | | | |
|---|---|---|---|---|---|
| TG12-25 | pyrimidin-4-yl-2-amine | R₂=5,6-difluoro, X=Y= H | 18.3 | ND | ND |
| TG12-30 | 1H-pyrrolo[2,3-b]pyridin-5-yl | R₂=X=Y= H | 0.6 | ND | ND |
| TG12-31 | pyrimidin-4-yl-2-amine | R₂=F, X=Y= H | 28.8 | ND | ND |
| TG12-35 | pyrimidin-4-yl-2-amine | R₂=Cl, X=Y= H | 8.9 | ND | ND |
| TG12-06 | 1H-indazol-5-yl | R₂=X=Y= H | 0.6 | ND | ND |
| TG12-37 | 1-methyl-1H-imidazol-4-yl | R₂=X=Y= H | 43.5 | ND | ND |
| TG12-41 | -O-CH₂-Ph | X=N, R₂=Y= H | 1875 | ND | ND |
| TG10-215 -Salt | pyrimidin-5-yl-2-amine·HCl | R₂=X=Y= H | 15.7 | 720 | 74 |
| TG12-44 | pyrimidin-5-yl-2-amine | Y=N, R₂=X= H | 13.7 | 25450 | ND |
| TG12-48 | adamantyl-C(O)NH- | R₂=X=Y= H | 175 | ND | ND |
| TG12-59 | 6-methylpyridin-2-yloxy | R₂=X=Y= H | 103 | 3022 | ND |
| TG12-69 | pyrimidin-5-yl-2-amine | R₂=Cl, X=Y= H | 7.8 | 890 | ND |

FIG. 6E

| Compd. ID | R₁ | EP2 K_B (nM) | Aq. sol. (nM) | Compd. ID | R₁ | EP2 K_B (nM) | Aq. sol. (nM) |
|---|---|---|---|---|---|---|---|
| TG8-15 |  | 22.3 | 257 | TG8-69 |  | 48.5 | 500 |
| TG8-130 |  | 6.6 | 100 | TG8-192 |  | 3.9 | 116 |
| TG8-168 |  | 4.4 | 100 | TG11-160 |  | 18.9 | ND |
| TG8-184 |  | 50 | 223 | TG8-197 |  | 50 | 221 |
| TG8-237 |  | 19.5 | 130 | TG8-260 |  | 12.8 | 158 |
| TG8-239 |  | 31.4 | 75 | TG8-242 |  | 29.5 | 135 |
| TG8-186 |  | 35 | 127 | TG9-57 |  | 86 | ND |
| TG8-238 |  | 46.6 | 75 | TG8-240 |  | 41.7 | 70 |
| TG8-258 |  | 30.5 | 76 | TG8-249 |  | 23.7 | 70 |

| Compd. ID | Structure | EP2 $K_B$ (nM) | Aq. Sol. (μM) |
|---|---|---|---|
| TG7-174 | 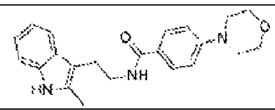 | 28.6 | 70 |
| TG9-175 | 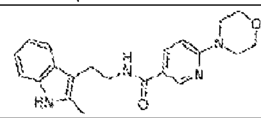 | 118 | 206 |
| TG9-77 | 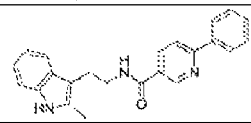 | 23.2 | ND |
| TG9-76 | 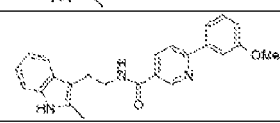 | 9.5 | 13 |
| TG9-100 | 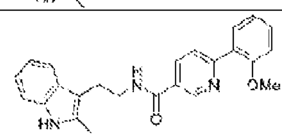 | 10 | >100 |
| TG9-131 | 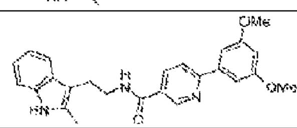 | 2.9 | >100 |
| TG9-83 | 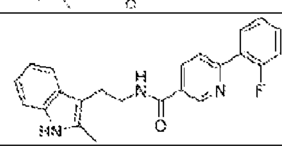 | 48.4 | 22 |
| TG11-167 | 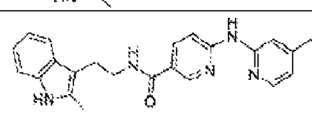 | 22 | ND |
| TG11-169 | 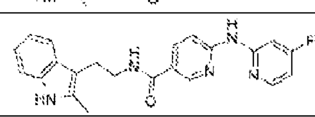 | 22.1 | ND |
| TG9-84-2 | 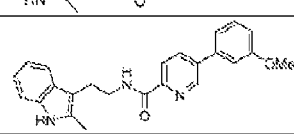 | 48.6 | ND |
| TG9-143 | 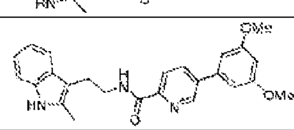 | 33.6 | ND |
| TG9-126 | 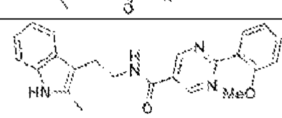 | 29.6 | >100 |
| TG11-265 | 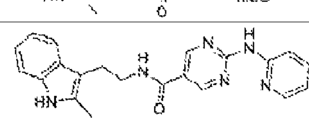 | 5.0 | |

FIG. 9A

| Compound | Structure | EP2 K$_B$ (nM) | Solubility μM |
|---|---|---|---|
| TG11-85 | 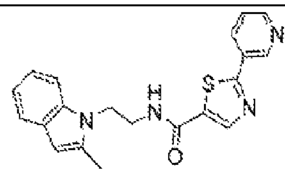 | 25.2 | IP |
| TG11-83 | 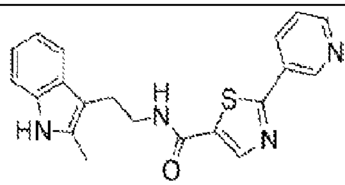 | 50.6 | IP |
| TG10-191 | 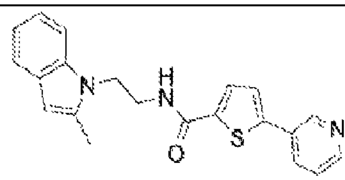 | 23.8 | ND |
| TG10-192 | 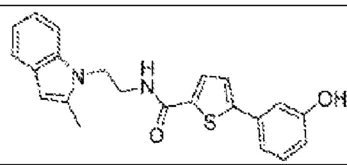 | 76 | ND |
| TG10-185 | 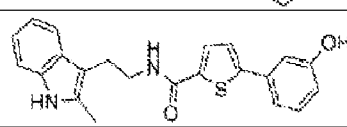 | 48.4 | ND |
| TG10-131 | 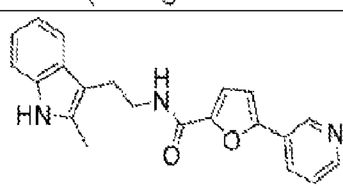 | 215 | ND |
| TG10-184 | 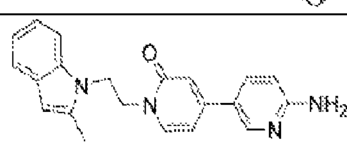 | 490 | ND |

FIG. 9B

| Compound | Structure | EP2 $K_B$ (nM) | Solubility μM |
|---|---|---|---|
| TG9-77 | 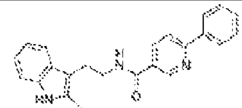 | 23.2 | ND |
| TG9-76 | 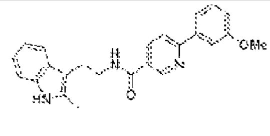 | 9.5 | 13.4 >100 (SGF) |
| TG9-78 | 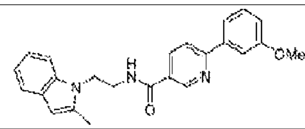 | 12.4 | ND |
| TG9-79 | 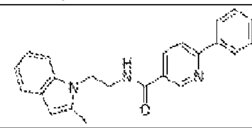 | 31 | ND |
| TG9-83 | 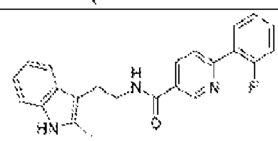 | 48.4 | 22 |
| TG9-84-2 | 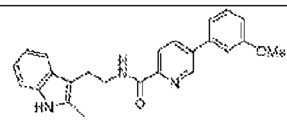 | 48.6 | ND |
| TG9-87-2 | 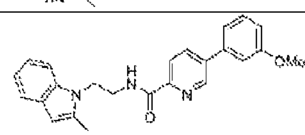 | 49.5 | ND |
| TG9-70 | 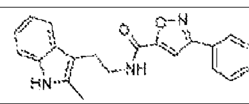 | 113 | 25 |
| TG7-249 | 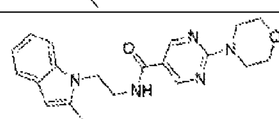 | 76.5 | >100 |
| TG8-9 | 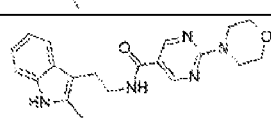 | 282 | >100 |
| TG7-244 | 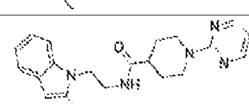 | 380 | ND |
| TG8-250 | 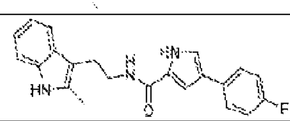 | 9.8 | 25 |
| TG11-73 | 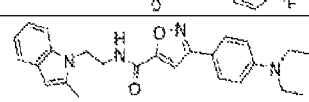 | 42.0 | ND |

| | | | |
|---|---|---|---|
| TG9-176 |  | 71 | 175 |
| TG10-09 |  | 4.4 | 25 |
| TG10-13 |  | 6.3 | 30 |
| TG10-15 |  | 9.3 | ND |
| TG11-35 |  | 57.5 | >100 |
| TG11-75 |  | 92.2 | ND |
| TG10-282 |  | 15.6 | >100 |
| TG7-230 |  | 19.5 | 22 |
| TG7-245 |  | 22.7 | 35 |
| TG7-242 |  | 29.5 | 25 |

PROSTAGLANDIN RECEPTOR EP2 ANTAGONISTS, DERIVATIVES, AND USES RELATED THERETO

CROSS REFERENCE TO RELATED APPLICATIONS

This application is a National Stage Application filed under 35 U.S.C. § 371 of PCT/US2020/023659, filed Mar. 19, 2020, which claims the benefit of priority to U.S. Provisional Application 62/821,163, filed Mar. 20, 2019, which are incorporated by reference herein in their entireties.

STATEMENT REGARDING FEDERALLY FUNDED RESEARCH

The invention was made with government support under AG052460, NS101167 and NS097776 awarded by the National Institutes of Health. The government was certain rights in the invention.

BACKGROUND

Cyclooxygenase-2 (COX-2), the inducible isoform of cyclooxygenase, is a major driver of inflammation in many diseases and disorders, both in brain and periphery. These diseases include rheumatoid arthritis, osteoarthritis, endometriosis, postoperative pain, inflammatory bowel disorders, Alzheimer's Disease, certain cancers, and epilepsy, among others. COX-2 is rapidly upregulated in damaged tissue, for example in the central nervous system (CNS) after a prolonged seizure or cerebral ischemia. Status epilepticus is a condition in which the brain is in a state of persistent seizure. There is evidence that 30-60 minutes of persistent seizure is sufficient to damage neurons and such a seizure is unlikely to self-terminate. Status epilepticus survivors may die soon after or have severe functional impairments accompanied by neuroinflammation. Longer seizure duration, cerebral insult, and refractory convulsive status epilepticus were strongly associated with poor outcomes suggesting a role for early neuroprotective strategies. See Legriel et al., Critical Care Medicine, 2010, 38 (12):2295-2303. Thus, there is a need to identify improved methods for treating or preventing patients recovering from prolonged seizures.

In the CNS, COX-2 induction overall contributes to neuroinflammation and neurodegeneration by producing prostaglandins. In the periphery COX-2 induction has both beneficial and harmful consequences. Pharmacological inhibition of COX can provide relief from the symptoms of inflammation and pain. Current non-steroidal anti-inflammatory drugs (NSAIDs), such as aspirin, ibuprofen, and naproxen, exert their therapeutic effects via nonselectively inhibiting COX. However, multiple downstream COX-2 signaling pathways that promote and oppose tissue injury are complex, which suggests that modulation of a specific prostaglandin receptor could be a superior therapeutic strategy compared with blocking the entire COX-2 cascade.

Prostaglandin $E_2$ ($PGE_2$), a dominant enzymatic product of COX-2 in CNS, can activate four G protein-coupled receptors (GPCRs): EP1, EP2, EP3 and EP4. When activated by $PGE_2$, EP2 stimulates adenylate cyclase (AC) resulting in elevation of cytoplasmic cyclic AMP (cAMP) concentration, which triggers multiple downstream events mediated by protein kinase A (PKA) and exchange protein activated by cAMP (Epac). $PGE_2$/EP2 signaling plays a variety of roles. For example, $PGE_2$ is a major mediator of inflammation and pain. $PGE_2$ is observed as one of the major prostanoid species in inflammatory lesions such as arthritic joints and endometriotic lesions, and shows pleiotropic proinflammatory actions in vitro. Therefore, the beneficial effect of NSAIDs could be at least partially if not fully, caused by their inhibition of $PGE_2$ production, and the $PGE_2$/EP2 signaling pathway might induce inflammation actions observed in chronic inflammatory diseases such as rheumatoid arthritis (RA).

$PGE_2$/EP2 signaling regulates UV-induced acute skin inflammation by increasing skin microenviromental blood flow, and EP2 activation by oxidized 1-palmitoyl-2-arachidonoyl-sn-glycero-3-phosphorylcholine (OxPAPC) that might contribute to vascular inflammation. $PGE_2$ signaling through EP2/EP4 exacerbates symptoms of inflammation by increasing IL-23 expression and reducing IL-12/IL-27, which together causes T-cells to differentiate to Th17 effectors both in inflammatory bowel disease (colitis) and arthritis. The $PGE_2$/EP2 system up-regulates a variety of inflammatory mediators including chemokines, cytokines, nitric oxide, prostaglandins, etc., to develop and maintain the inflammatory response.

In the brain, based on the phenotype of EP2 knockout mice, it appears that EP2 activation in microglia promotes inflammation and neurotoxicity in animal models of neurodegenerative diseases including Alzheimer's disease (AD), Parkinson's disease (PD), and amyotrophic lateral sclerosis (ALS). Genetic ablation of EP2 receptor reduced oxidative stress and improved cell survival, accompanied by substantial down-regulation of enzymes in glia that produce reactive oxygen species (ROS), such as inducible nitric oxide synthase (iNOS), COX-2, and NAPDH oxidase. EP2 receptor activation by $PGE_2$ upregulates iNOS/NO expression in activated astrocytes by potentiating the response to inflammatory cytokines like TNF-α and IFN-γ.

Because $PGE_2$/EP2 signaling mediates both peripheral and neural inflammation, pharmacological targeting of this pathway can have beneficial implications for the treatment of inflammatory diseases. Thus, there is a need to identify agents that can inhibit $PGE_2$/EP2 signaling.

Buchmann et al., (WO/2008/152099) report compositions for the treatment of disorders connected with the EP2 receptor. See also U.S. Published Patent Applications 2014/0179750 2017/0042905, 2017/0081314, and 2018/0318315.

Rojas et al. report inhibition of the prostaglandin E2 receptor EP2 prevents status epilepticus-induced memory deficits. Neuropharmacology. 2016, 110(Pt A):419-430.

Ganesh et al. report an EP2 antagonist with anti-inflammatory properties, Mol. Pharmaceutics, 2018, 15 (12), pp 5809-5817.

Aoki et al. report prostaglandin E2-EP2-NF-κB signaling in macrophages as a potential therapeutic target for intracranial aneurysms. Sci Signal. 2017, 10(465). pii: eaah6037.

References cited herein are not an admission of prior art.

SUMMARY

It has been discovered that certain compounds antagonize EP2 signaling. In some embodiments, this disclosure relates to compounds and methods of treating or preventing related diseases or conditions comprising administering to a subject a therapeutically effective amount of pharmaceutical composition comprising a compound disclosed herein, derivatives, or substituted compounds, e.g., compounds substituted with one or more substitutes including optional salt and prodrug forms. Typically, the compounds display selectivity in inhibiting the EP2 receptor over the EP4 receptor.

In certain embodiments, the compounds can be combined with one or more pharmaceutically acceptable excipients to form a pharmaceutical composition. Example excipients include dilutent, carrier or filler. The compositions can be formulated for enteral, parenteral, topical, transdermal, or pulmonary administration. The compounds can be formulated for immediate release, controlled release, and combinations thereof. Examples of controlled release formulations include delayed release, extended release, pulsatile release, and combinations thereof.

In certain embodiments, the compounds described herein can be used to treat a variety of diseases or conditions related to a EP2 receptor including, but not limited to, brain injury, neuropathic pain, hypertension, ischemic or hemorrhagic injury, neuroinflammation after a seizure, endometriosis, cancer, inflammatory bowel disease (colitis), arthritis/rheumatoid arthritis, skin inflammation, vascular inflammation, Alzheimer's disease (AD), Parkinson's disease (PD), amyotrophic lateral sclerosis (ALS), kidney disease/transplant rejection, atherosclerosis, ischaemic heart disease, acne vulgaris, asthma, chronic prostatitis, glomerulonephritis, hypersensitivities, pelvic inflammatory disease, sarcoidosis, vasculitis, interstitial cystitis, preterm delivery, and autoimmune diseases.

In certain embodiments, the compounds described herein can be used to treat subarachnoid haemorrhage or to prevent rupture of intracranial aneurysms.

In certain embodiments, the compounds described herein can be used to treat colon cancer, colon or colon tumor growth.

In certain embodiments, compounds described herein can be used to treat or prevent pain, e.g., post surgical pain.

In certain embodiments, compounds described herein can be used to treat or prevent mechanical hyperalgesia or delayed-onset muscle soreness.

In certain embodiments, compounds described herein can be used to treat or prevent diabetes mellitus-induced inflammation and microvascular dysfunction or diabetic retinopathy.

In certain embodiments, the disclosure relates to the use of a compound as described herein in the production of a medicament for the treatment of a disease or condition related to an EP2 receptor. Compounds disclosed here can be contained in pharmaceutical compositions and administered alone or in combination with one or more additional active agents. The active agents can be administered simultaneously in the same dosage form or in separate dosage forms. Alternatively, the active agents can be administered sequentially in different dosage forms.

In certain embodiments, the disclosure relates to method of making compounds disclosed herein by mixing starting materials and reagents disclosed herein under conditions such that the compounds are formed.

BRIEF DESCRIPTION OF THE DRAWINGS

FIG. 2B shows data on EP2 antagonistic activity for compounds shown in FIG. 2A.

FIG. 6A shows data for additional compounds of this disclosure.

FIG. 6C shows data for additional compounds of this disclosure.

FIG. 6D shows data for additional compounds of this disclosure.

FIG. 6E shows data for additional compounds of this disclosure.

ethan-1-amine or 2-(2-methyl-1H-indol-3-yl)ethan-1-amine using EDCl, DMAP, DCM/DMF, at RT.

Figure 8A:
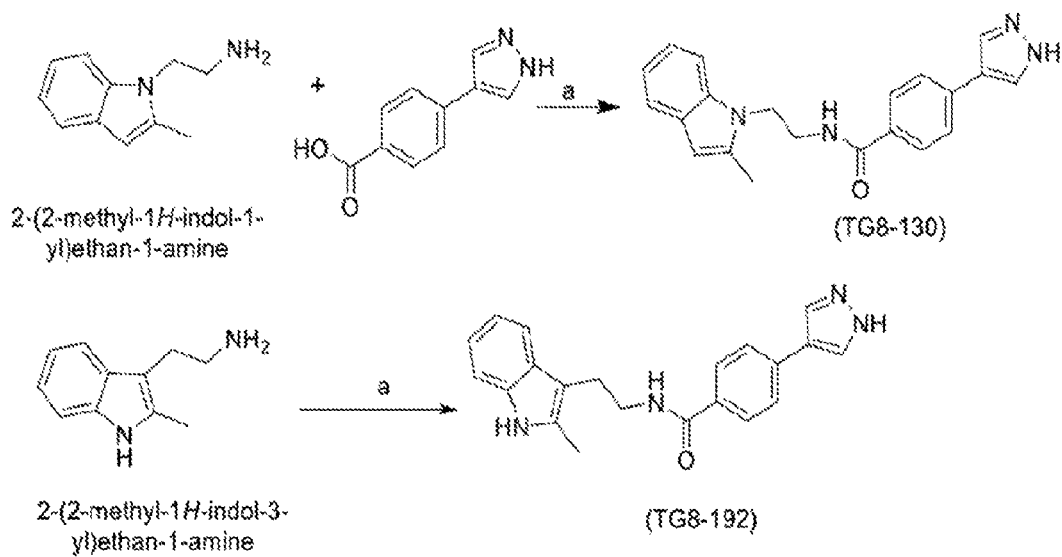
FIG. 8A illustrates the synthesis of bioisosteric derivatives by amide coupling to 2-(2-methyl-1H-indol-1-yl)
Figure 8B:

FIG. 8B illustrates the activity of the corresponding derivatives.

FIG. 9A shows data for additional compounds of this disclosure.

FIG. 9B shows data for additional compounds of this disclosure.

Figure 9C:
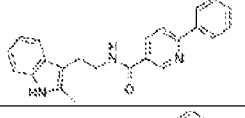
Figure 9C:
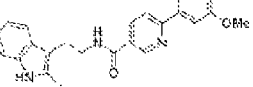
Figure 9C:
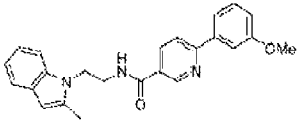
Figure 9C:
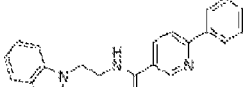
Figure 9C:
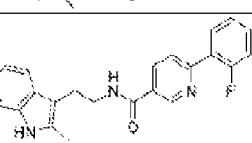
Figure 9C:
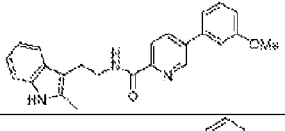
Figure 9C:
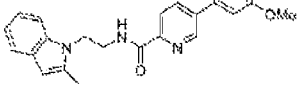
Figure 9C:
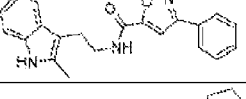
Figure 9C:
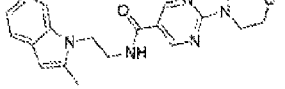
Figure 9C:
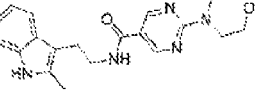
Figure 9C:
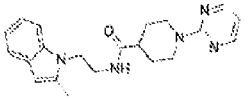
Figure 9C:
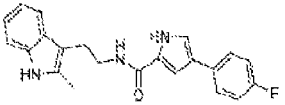
Figure 9C:
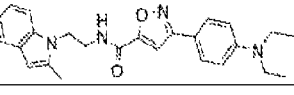

FIG. 9C shows data for additional compounds of this disclosure.

Figure 9D:
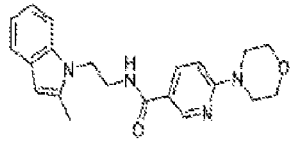
Figure 9D:
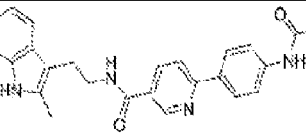
Figure 9D:
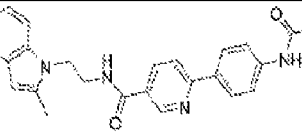
Figure 9D:
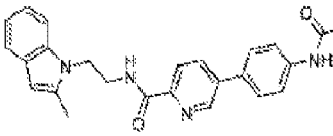
Figure 9D:
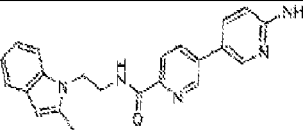
Figure 9D:
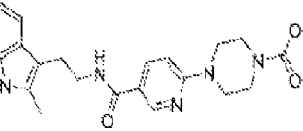
Figure 9D:
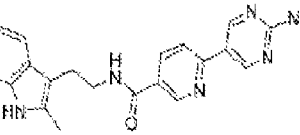
Figure 9D:
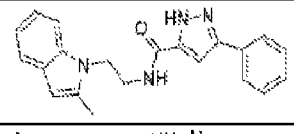
Figure 9D:
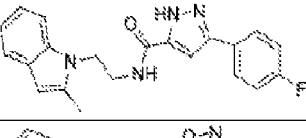
Figure 9D:
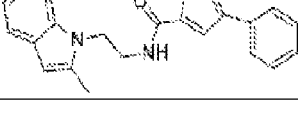

FIG. 9D shows data for additional compounds of this disclosure.

Figure 10:
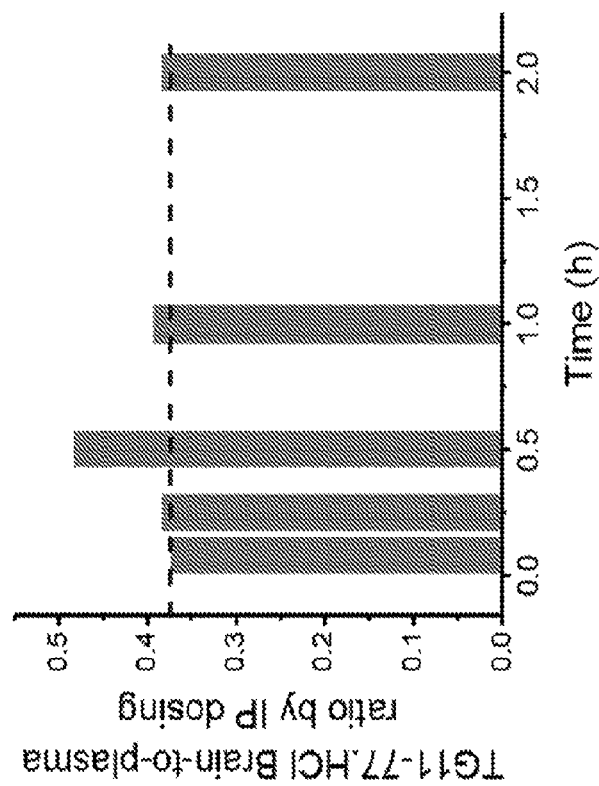
Figure 10:
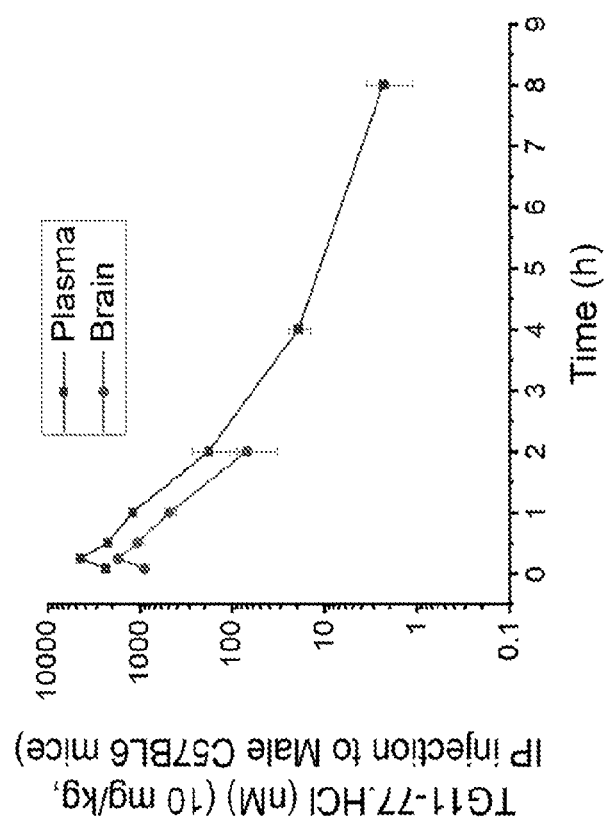

FIG. 10 shows pharmacokinetic parameters of 20o.HCl. Compound 20o.HCl (TG11-77HCl) was administered in to male C57BL/6 mice via intraperitoneal injection at single dose of 10 mg/kg in the vehicle of 5% NMP, 5% Solutol-HS15 and 90% water. Concentrations in plasma and brain are determined by LC-MS/MS and plotted against time.

Figures 11A, 11B:
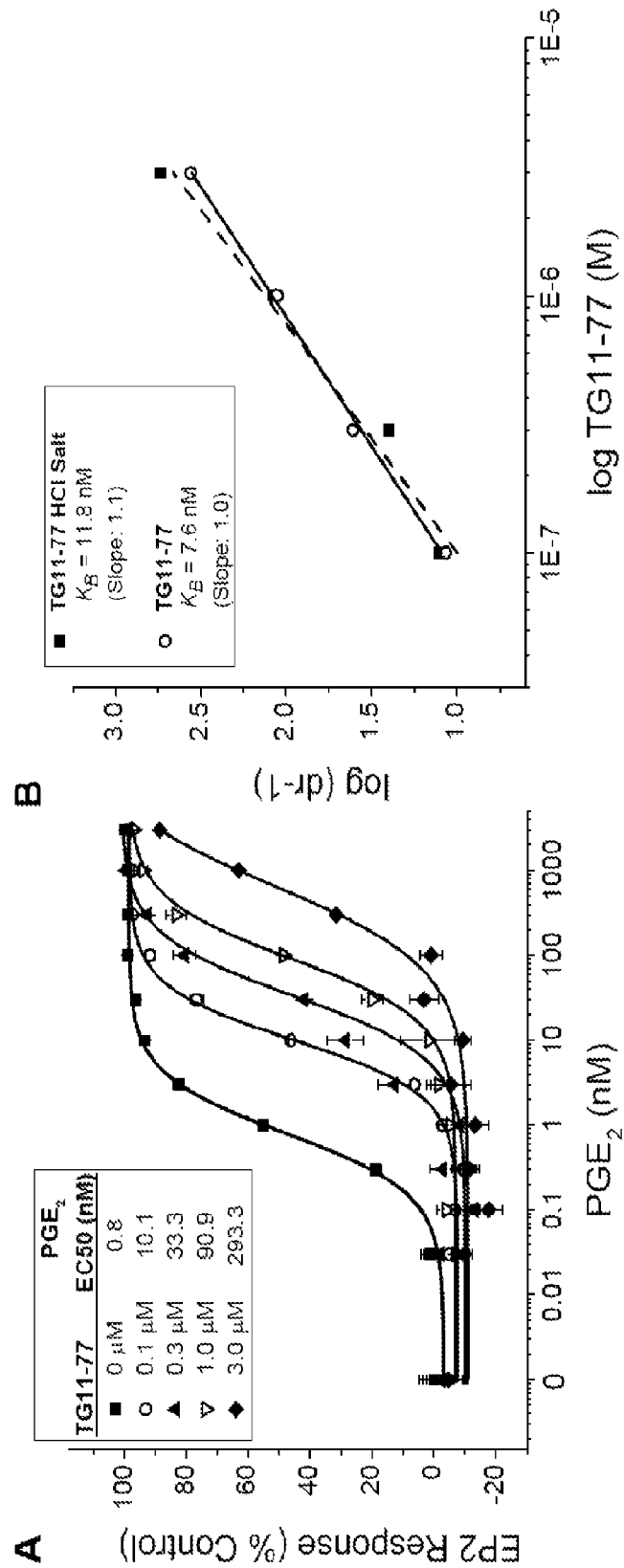
Figure 11C:
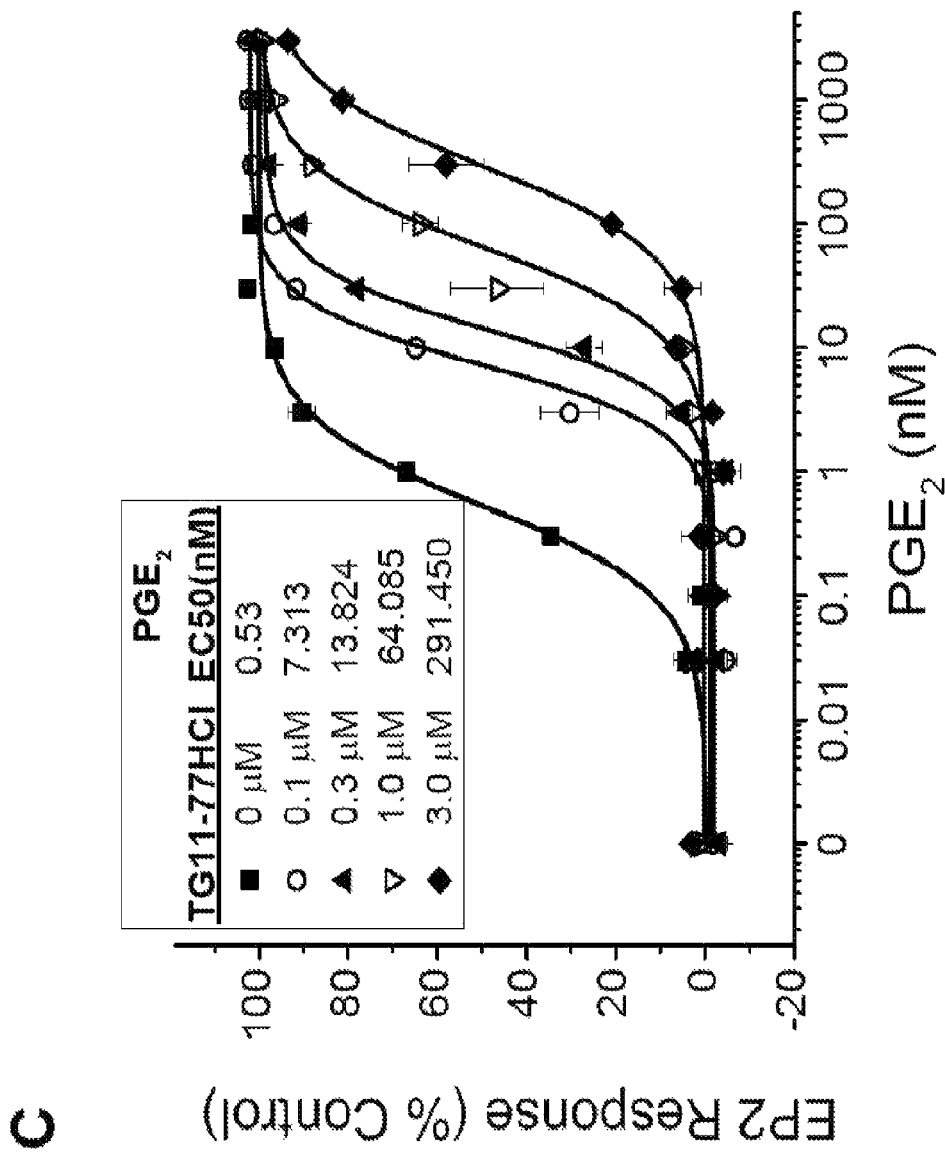
Figure 11D:
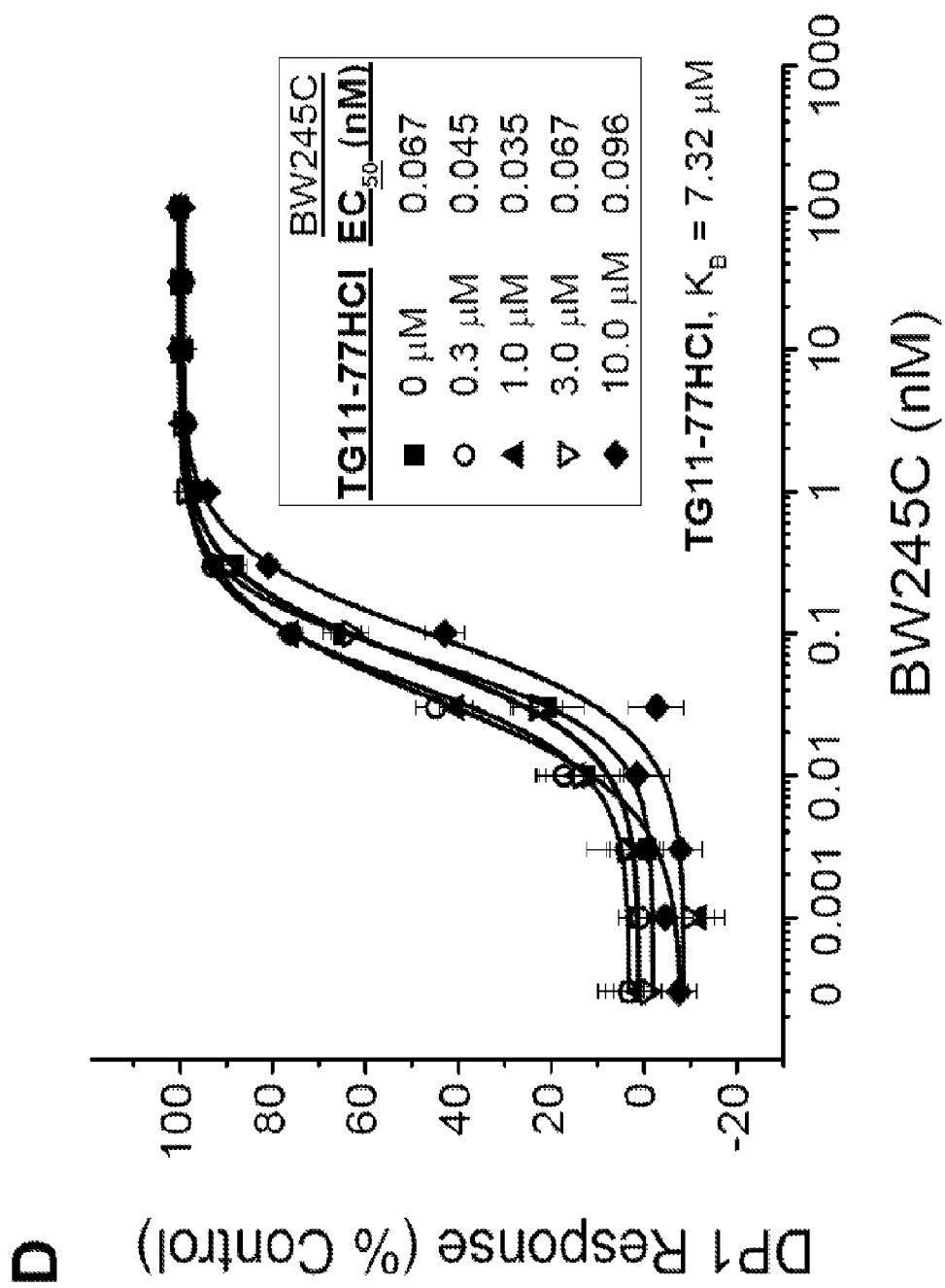

FIGS. 11A-11D show the competitive antagonism of EP2 receptor by TG11-77HCl. FIG. 11A shows TG11-77 (neutral) inhibited PGE2-induced human EP2 receptor activation in a concentration dependent manner. FIG. 11B shows Schild regression analysis performed to determine the modality of antagonism by this compound. FIG. 11C show the TG11-77 hydrochloride salt (TG11-77.HCl) similarly inhibited PGE2-induced human EP2 receptor activation in a concentration-dependent manner. Schild KB values for neutral compound and the hydrochloride salt along with their slope values are shown in inset of FIG. 11B. FIG. 11D show the concentration-response test of TG11-77.HCl on DP1 receptors, which indicates it does not significantly inhibit DP1 receptor activation by agonist BW245C. Data were normalized as percentage of maximum response; points represent mean±SEM (n=3).

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise.

Terms

As used herein, "alkyl" means a noncyclic straight chain or branched, unsaturated or saturated hydrocarbon such as those containing from 1 to 10 carbon atoms, typically 1 to 6 carbon atoms. Within any embodiments, herein alkyl may refer to an alkyl with 1 to 6 carbons ($C_{1-6}$alkyl). Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like.

"Heterocarbocycles" or heterocarbocyclyl" groups are carbocycles which contain from 1 to 4 heteroatoms independently selected from nitrogen, oxygen and sulfur which may be saturated or unsaturated (but not aromatic), monocyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Aryl" means an aromatic carbocyclic monocyclic or polycyclic ring such as phenyl or naphthyl. Polycyclic ring systems may, but are not required to, contain one or more non-aromatic rings, as long as one of the rings is aromatic.

As used herein, "heteroaryl" refers an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Alkylthio" refers to an alkyl group as defined above with the indicated number of carbon atoms attached through a sulfur bridge. An example of an alkylthio is methylthio, (i.e., —S—$CH_3$).

"Alkoxy" refers to an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy.

"Alkylamino" refers an alkyl group as defined above attached through an amino bridge. An example of an alkylamino is methylamino, (i.e., —NH—$CH_3$).

"Alkanoyl" refers to an alkyl as defined above attached through a carbonyl bride (i.e., —(C=O)alkyl).

"Alkyloxycarbonyl" refers to an alkyl as defined above attached through a carboxy bridge (i.e., —(C=O)Oalkyl.

"Alkylcarbamoyl" refers to an alkyl as defined above attached through a carbonyl bridge (i.e., —(C=O)NHalkyl).

"Alkanoyl" refers to an alkyl as defined above attached through a carbonyl bridge (i.e., —(C=O)alkyl).

"Alkylsulfonyl" refers to an alkyl as defined above attached through a sulfonyl bridge (i.e., —S(=O)$_2$alkyl) such as mesyl and the like, and "Arylsulfonyl" refers to an aryl attached through a sulfonyl bridge (i.e., —S(=O)$_2$aryl).

"Alkylsulfonamide" refers to an alkyl as defined above attached through a sulfamoyl bridge (i.e., —S(=O)$_2$NHalkyl), and an "Arylsulfonamide" refers to an alkyl attached through a sulfamoyl bridge (i.e., (i.e., —S(=O)$_2$NHaryl).

"Alkylsulfinyl" refers to an alkyl as defined attached through a sulfinyl bridge (i.e. —S(=O)alkyl).

The terms "halogen" and "halo" refer to fluorine, chlorine, bromine, and iodine.

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —$NR_aR_b$, —$NR_aC(=O)R_b$, —$NR_aC(=O)NR_aNR_b$, —$NR_aC(=O)OR_b$, —$NR_aSO_2R_b$, —C(=O)$R_a$, —C(=O)$OR_a$, —C(=O)$NR_aR_b$, —OC(=O)$NR_aR_b$, —$OR_a$, —$SR_a$, —$SOR_a$, —S(=O)$_2R_a$, —OS(=O)$_2R_a$ and —S(=O)$_2OR_a$. $R_a$ and $R_b$ in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

The term "optionally substituted," as used herein, means that substitution is optional and therefore it is possible for the designated atom to be unsubstituted.

As used herein, "salts" refer to derivatives of the disclosed compounds where the parent compound is modified making acid or base salts thereof. Examples of salts include, but are not limited to, mineral or organic acid salts of basic residues such as amines, alkylamines, or dialkylamines; alkali or organic salts of acidic residues such as carboxylic acids; and the like. In certain embodiment the salts are conventional nontoxic pharmaceutically acceptable salts including the quaternary ammonium salts of the parent compound formed, and non-toxic inorganic or organic acids. Contemplated salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

"Subject" refers any animal, preferably a human patient, livestock, or domestic pet.

The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g. patient) is cured and the disease is eradicated. Rather, embodiments, of the present disclosure also contemplate treatment that merely reduces symptoms, and/or delays disease progression.

As used herein, the term "combination with" when used to describe administration with an additional treatment means that the agent may be administered prior to, together with, or after the additional treatment, or a combination thereof.

As used herein, the term "derivative" refers to a structurally similar compound that retains sufficient functional attributes of the identified analogue. The derivative may be structurally similar because it is lacking one or more atoms, substituted, a salt, in different hydration/oxidation states, or because one or more atoms within the molecule are switched, such as, but not limited to, replacing a oxygen atom with a sulfur atom or replacing an amino group with a hydroxyl group. The derivative may be a prodrug. Derivatives may be prepared by any variety of synthetic methods or appropriate adaptations presented in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference.

Prostaglandin Receptor EP2 Antagonists/Inhibitors

Certain compounds were identified as antagonists of the human EP2 receptor. Although it is not intended that certain embodiments of the disclosure be limited by any specific mechanism, certain of these compounds have low cellular toxicity and represent competitive antagonists of the EP2 prostaglandin receptor.

In certain embodiments, compounds have Formula I,

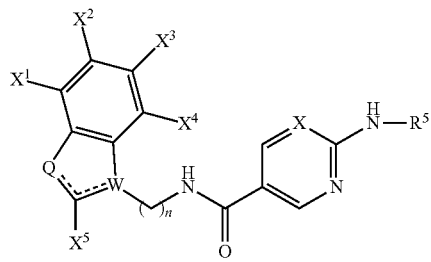

Formula I or salt or prodrug thereof, wherein:
a dotted line represents a double or single bond,
n is 1, 2, 3, or 4;
Q is CH, N, or $NX^6$;
W is N or C;
X is N or CH;
$R^5$ is alkyl, carbocyclyl, aryl, or heterocyclyl, wherein $R^5$ is optionally substituted with one or more, the same or different, $R^{10}$;
$X^1$, $X^2$, $X^3$, and $X^4$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^1$, $X^2$, $X^3$, and $X^4$ are optionally substituted with one or more, the same or different, $X^{10}$;
$X^5$ and $X^6$ are each, the same or different, hydrogen or alkyl, wherein $X^5$ and $X^6$ are optionally substituted with one or more, the same or different, $X^{10}$;
$X^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^{10}$ is optionally substituted with one or more, the same or different, $X^{11}$;
$X^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;
$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;
$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$; and
$R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, Q is $NX^6$ and W is C.
In certain embodiments, Q is CH and W is N.
In certain embodiments, Q is N and W is N.
In certain embodiments, $R^5$ is pyridin-2-yl or pyridin-3-yl optionally substituted with one or more, the same or different, $R^{10}$.

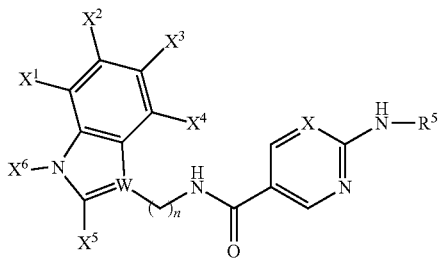

Formula IA or pharmaceutically acceptable salt or prodrug thereof, wherein:
n is 1, 2, 3, or 4;
W is N or C;
X is N or CH;
$R^5$ is alkyl, carbocyclyl, aryl, or heterocyclyl, wherein $R^5$ is optionally substituted with one or more, the same or different, $R^{10}$;
$X^1$, $X^2$, $X^3$, and $X^4$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^1$, $X^2$, $X^3$, and $X^4$ are optionally substituted with one or more, the same or different, $X^{10}$;
$X^5$ and $X^6$ are each, the same or different, hydrogen or alkyl, wherein $X^5$ and $X^6$ are optionally substituted with one or more, the same or different, $X^{10}$;
$X^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^{10}$ is optionally substituted with one or more, the same or different, $X^{11}$;
$X^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$; and $R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, compounds have Formula IB,

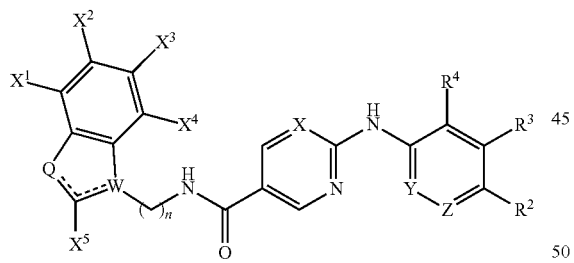

Formula IB or salt or prodrug thereof, wherein:
a dotted line represents a double or single bond,
n is 1, 2, 3, or 4;
Q is CH, N, or $NX^6$;
W is N or C;
X is N or CH;
Y is N or CH;
Z is N or $CR^1$
$R^1$, $R^2$, $R^3$, and $R^4$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^1$, $R^2$, $R^3$, and $R^4$ are optionally substituted with one or more, the same or different, $R^{10}$;

$X^1$, $X^2$, $X^3$, and $X^4$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^1$, $X^2$, $X^3$, and $X^4$ are optionally substituted with one or more, the same or different, $X^{10}$;

$X^5$ and $X^6$ are each, the same or different, hydrogen or alkyl, wherein $X^5$ and $X^6$ are optionally substituted with one or more, the same or different, $X^{10}$;

$X^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^{10}$ is optionally substituted with one or more, the same or different, $X^{11}$;

$X^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$; and $R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, Q is $NX^6$ and W is C.

In certain embodiments, Q is CH and W is N.

In certain embodiments, Q is N and W is N.

In certain embodiments, compounds have Formula IC,

Formula IC

[Chemical structure image]

or salt or prodrug thereof, wherein:
n is 1, 2, 3, or 4;
W is N or C;
X is N or CH;
Y is N or CH;
Z is N or $CR^1$
$R^1$, $R^2$, $R^3$, and $R^4$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^1$, $R^2$, $R^3$, and $R^4$ are optionally substituted with one or more, the same or different, $R^{10}$;
$X^1$, $X^2$, $X^3$, and $X^4$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^1$, $X^2$, $X^3$, and $X^4$ are optionally substituted with one or more, the same or different, $X^{10}$;
$X^5$ and $X^6$ are each, the same or different, hydrogen or alkyl, wherein $X^5$ and $X^6$ are optionally substituted with one or more, the same or different, $X^{10}$;
$X^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^{10}$ is optionally substituted with one or more, the same or different, $X^{11}$;
$X^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;
$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;
$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$; and
$R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, W is C, X is N, Y is N, and Z is $CR^1$.

In certain embodiments, $R^1$ is halogen, alkyl, hydroxy, alkoxy, or cyano and $R^3$ is hydrogen, halogen, or alkyl.

In certain embodiments, $R^3$ is halogen or alkyl, and $R^1$ is hydrogen, halogen, alkyl, hydroxy, alkoxy, or cyano.

In certain embodiments, $X^3$ is halogen, $R^1$ is hydrogen, halogen, alkyl, hydroxy, alkoxy, or cyano and $R^3$ is hydrogen, halogen, or alkyl.

In certain embodiments, $X^1$ is halogen, $X^3$ is hydrogen or halogen, $R^1$ is hydrogen, halogen, alkyl, hydroxy, alkoxy, or cyano and $R^3$ is hydrogen, halogen, or alkyl.

In certain embodiments, $X^5$ is alkyl or alkyl substituted with one or more halogens.

In certain embodiments, n is 2, $R^1$ is halogen, alkyl, hydroxy, alkoxy, or cyano and $R^3$ is hydrogen, halogen, or alkyl.

In certain embodiments, n is $2R^3$ is halogen or alkyl, and $R^1$ is hydrogen, halogen, alkyl, hydroxy, alkoxy, or cyano.

In certain embodiments, n is 2, $X^3$ is halogen, $R^1$ is hydrogen, halogen, alkyl, hydroxy, alkoxy, or cyano and $R^3$ is hydrogen, halogen, or alkyl.

In certain embodiments, n is 2, $X^1$ is halogen, $X^3$ is hydrogen or halogen, $R^1$ is hydrogen, halogen, alkyl, hydroxy, alkoxy, or cyano and $R^3$ is hydrogen, halogen, or alkyl.

In certain embodiments, n is 2, $X^5$ is alkyl or alkyl substituted with one or more halogens.

In certain embodiments, the compound is 2-((4,6-dimethylpyridin-2-yl)amino)-N-(2-(2-methyl-1H-indol-3-yl)ethyl)pyrimidine-5-carboxamide (TG11-77) or salts thereof.

In certain embodiments, the compound is 2-((4,6-dimethylpyridin-2-yl)amino)-N-(2-(7-fluoro-2-methyl-1H-indol-3-yl)ethyl)pyrimidine-5-carboxamide (TG11-283) or salts thereof.

In certain embodiments, the compound is selected from:
N-(2-(2-methyl-1H-indol-3-yl)ethyl)-2-(pyridin-2-ylamino)pyrimidine-5-carboxamide (TG11-265);
N-(2-(2-methyl-1H-indol-3-yl)ethyl)-2-((4-methylpyridin-2-yl)amino)pyrimidine-5-carboxamide (TG11-163);
N-(2-(2-methyl-1H-indol-3-yl)ethyl)-2-((6-methylpyridin-2-yl)amino)pyrimidine-5-carboxamide (TG11-214);
2-((4-fluoropyridin-2-yl)amino)-N-(2-(2-methyl-1H-indol-3-yl)ethyl)pyrimidine-5-carboxamide (TG11-199);
2-((6-fluoropyridin-2-yl)amino)-N-(2-(2-methyl-1H-indol-3-yl)ethyl)pyrimidine-5-carboxamide (TG11-215);
2-((6-methoxypyridin-2-yl)amino)-N-(2-(2-methyl-1H-indol-3-yl)ethyl)pyrimidine-5-carboxamide (TG11-275);
2-((6-hydroxypyridin-2-yl)amino)-N-(2-(2-methyl-1H-indol-3-yl)ethyl)pyrimidine-5-carboxamide (TG15-03);

2-((6-cyanopyridin-2-yl)amino)-N-(2-(2-methyl-1H-indol-3-yl)ethyl)pyrimidine-5-carboxamide (TG15-40);
N-(2-(5-fluoro-2-methyl-1H-indol-3-yl)ethyl)-2-((4,6-dimethylpyridin-2-yl)amino)pyrimidine-5-carboxamide (TG11-228);
N-(2-(5-chloro-2-methyl-1H-indol-3-yl)ethyl)-2-((4,6-dimethylpyridin-2-yl)amino)pyrimidine-5-carboxamide (TG11-242);
N-(2-(5,7-difluoro-2-methyl-1H-indol-3-yl)ethyl)-2-((4,6-dimethylpyridin-2-yl)amino)pyrimidine-5-carboxamide (TG11-224);
2-((4,6-dimethylpyridin-2-yl)amino)-N-(2-(2-(trifluoromethyl)-1H-indol-3-yl)ethyl)pyrimidine-5-carboxamide (TG15-48);
N-(2-(2-methyl-1H-indol-3-yl)ethyl)-2-((4-methylpyridin-2-yl)amino)pyrimidine-5-carboxamide (TG11-163);
or salt thereof.

In certain embodiments, W is C, X is CH, Y is N or CH, and Z is $CR^1$.

In certain embodiments, n is 2, W is C, X is CH, Y is N or CH, and Z is $CR^1$.

In certain embodiments, the compound is selected from:
N-(2-(2-methyl-1H-indol-3-yl)ethyl)-2-((4-methylpyridin-2-yl)amino)pyrimidine-5-carboxamide (TG11-167) and
2-((4-fluoropyridin-2-yl)amino)-N-(2-(2-methyl-1H-indol-3-yl)ethyl)pyrimidine-5-carboxamide (TG11-169).

In certain embodiments, compounds have Formula ID,

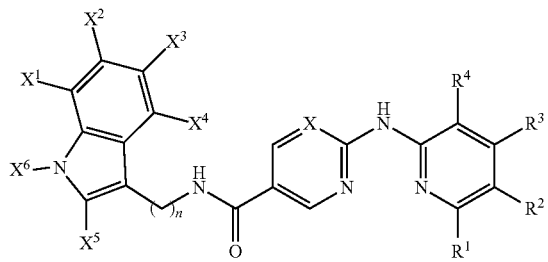

Formula ID or salt or prodrug thereof, wherein:
n is 1, 2, 3, or 4;
$R^1$, $R^2$, $R^3$, and $R^4$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^1$, $R^2$, $R^3$, and $R^4$ are optionally substituted with one or more, the same or different, $R^{10}$;
$X^1$, $X^2$, $X^3$, and $X^4$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^1$, $X^2$, $X^3$, and $X^4$ are optionally substituted with one or more, the same or different, $X^{10}$;
$X^5$ and $X^6$ are each, the same or different, hydrogen or alkyl, wherein $X^5$ and $X^6$ are optionally substituted with one or more, the same or different, $X^{10}$;
$X^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^{10}$ is optionally substituted with one or more, the same or different, $X^{11}$;
$X^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;
$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;
$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$; and
$R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, n is 2.
In certain embodiments, compounds have Formula IE,

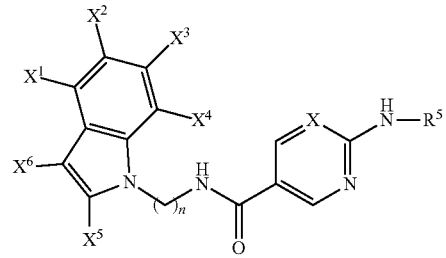

Formula IE or salt or prodrug thereof, wherein:
n is 1, 2, 3, or 4;
X is N or CH;
$R^5$ is alkyl, carbocyclyl, aryl, or heterocyclyl, wherein $R^5$ is optionally substituted with one or more, the same or different, $R^{10}$;
$X^1$, $X^2$, $X^3$, and $X^4$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^1$, $X^2$, $X^3$, and $X^4$ are optionally substituted with one or more, the same or different, $X^{10}$;

$X^5$ and $X^6$ are each, the same or different, hydrogen or alkyl, wherein $X^5$ and $X^6$ are optionally substituted with one or more, the same or different, $X^{10}$;

$X^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^{10}$ is optionally substituted with one or more, the same or different, $X^{11}$;

$X^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$; and $R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, n is 2.

In certain embodiments, compounds have Formula IF,

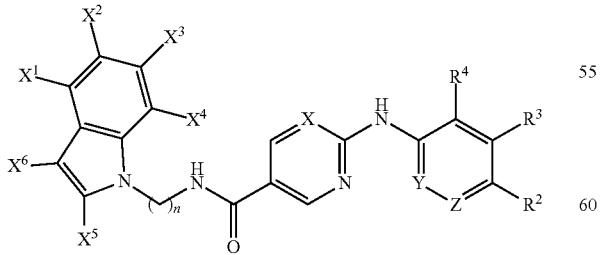

Formula IF or pharmaceutically acceptable salt or prodrug thereof, wherein:

n is 1, 2, 3, or 4;

X is N or CH;

Y is N or CH;

Z is N or $CR^1$ $R^1$, $R^2$, $R^3$, and $R^4$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^1$, $R^2$, $R^3$, and $R^4$ are optionally substituted with one or more, the same or different, $R^{10}$;

$X^1$, $X^2$, $X^3$, and $X^4$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^1$, $X^2$, $X^3$, and $X^4$ are optionally substituted with one or more, the same or different, $X^{10}$;

$X^5$ and $X^6$ are each, the same or different, hydrogen or alkyl, wherein $X^5$ and $X^6$ are optionally substituted with one or more, the same or different, $X^{10}$;

$X^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^{10}$ is optionally substituted with one or more, the same or different, $X^{11}$;

$X^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$; and $R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, n is 2.

In certain embodiments, compounds have Formula II,

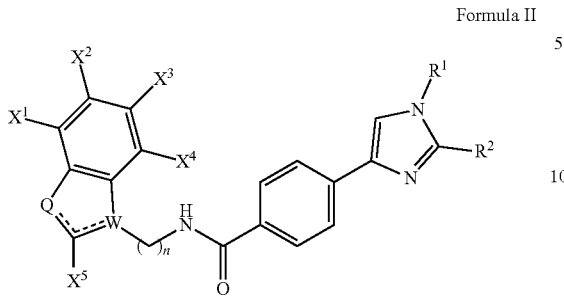

Formula II or pharmaceutically acceptable salt or prodrug thereof, wherein:
a dotted line represents a double or single bond,
n is 1, 2, 3, or 4;
Q is CH, N, or $NX^6$;
W is N or C;
$R^1$ and $R^2$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^1$ and $R^2$ are optionally substituted with one or more, the same or different, $R^{10}$;
$X^1$, $X^2$, $X^3$, and $X^4$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^1$, $X^2$, $X^3$, and $X^4$ are optionally substituted with one or more, the same or different, $X^{10}$;
$X^5$ and $X^6$ are each, the same or different, hydrogen or alkyl, wherein $X^5$ and $X^6$ are optionally substituted with one or more, the same or different, $X^{10}$;
$X^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^{10}$ is optionally substituted with one or more, the same or different, $X^{11}$;
$X^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;
$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;
$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$; and
$R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, Q is $NX^6$ and W is C.
In certain embodiments, Q is CH and W is N.
In certain embodiments, Q is N and W is N.
In certain embodiments, compounds have Formula III,

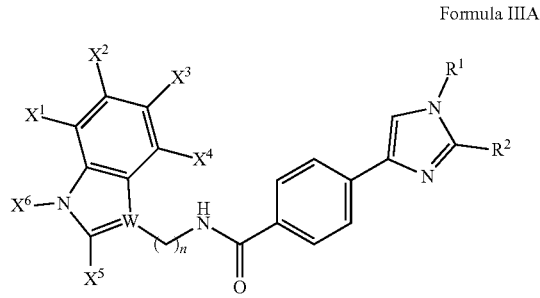

Formula IIIA or pharmaceutically acceptable salt or prodrug thereof, wherein:
n is 1, 2, 3, or 4;
W is N or C;
$R^1$ and $R^2$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^1$ and $R^2$ are optionally substituted with one or more, the same or different, $R^{10}$;
$X^1$, $X^2$, $X^3$, and $X^4$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^1$, $X^2$, $X^3$, and $X^4$ are optionally substituted with one or more, the same or different, $X^{10}$;
$X^5$ and $X^6$ are each, the same or different, hydrogen or alkyl, wherein $X^5$ and $X^6$ are optionally substituted with one or more, the same or different, $X^{10}$;
$X^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^{10}$ is optionally substituted with one or more, the same or different, $X^{11}$;
$X^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$; and $R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, compounds is selected from 4-(1H-imidazol-5-yl)-N-(2-(2-methyl-1H-indol-3-yl)ethyl) benzamide (TG8-260);
4-(2-methyl-1H-imidazol-5-yl)-N-(2-(2-methyl-1H-indol-3-yl)ethyl)benzamide (TG11-232); and
4-(1-methyl-1H-imidazol-5-yl)-N-(2-(2-methyl-1H-indol-3-yl)ethyl)benzamide (TG12-37; or salts thereof.

In certain embodiments, compounds have Formula III,

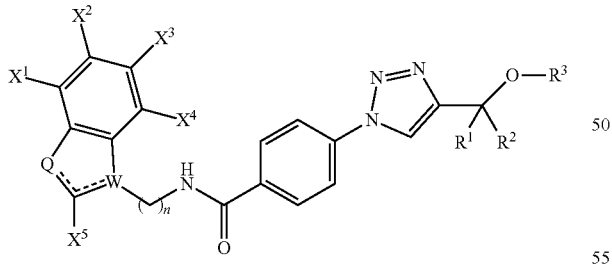

Formula III or pharmaceutically acceptable salt or prodrug thereof, wherein:
a dotted line represents a double or single bond,
n is 1, 2, 3, or 4;
Q is CH, N, or $NX^6$;
W is N or C;
$R^1$, $R^2$, and $R^3$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^1$, $R^2$, and $R^3$ are optionally substituted with one or more, the same or different, $R^{10}$;

$X^1$, $X^2$, $X^3$, and $X^4$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^1$, $X^2$, $X^3$, and $X^4$ are optionally substituted with one or more, the same or different, $X^{10}$;

$X^5$ and $X^6$ are each, the same or different, hydrogen or alkyl, wherein $X^5$ and $X^6$ are optionally substituted with one or more, the same or different, $X^{10}$;

$X^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^{10}$ is optionally substituted with one or more, the same or different, $X^{11}$;

$X^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$; and $R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, Q is $NX^6$ and W is C.
In certain embodiments, Q is CH and W is N.
In certain embodiments, Q is N and W is N.
In certain embodiments, n is 2.

In certain embodiments, compounds have Formula IIIA,

Formula IIIA

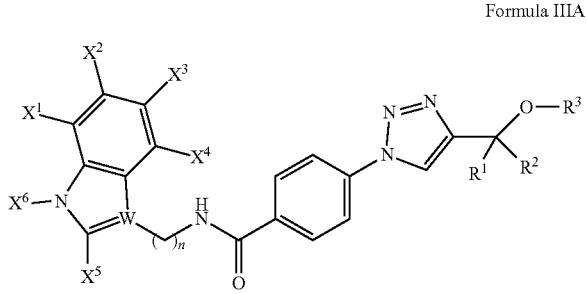

or pharmaceutically acceptable salt or prodrug thereof, wherein:

n is 1, 2, 3, or 4;

W is N or C;

$R^1$, $R^2$, and $R^3$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^1$, $R^2$, and $R^3$ are optionally substituted with one or more, the same or different, $R^{10}$;

$X^1$, $X^2$, $X^3$, and $X^4$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^1$, $X^2$, $X^3$, and $X^4$ are optionally substituted with one or more, the same or different, $X^{10}$;

$X^5$ and $X^6$ are each, the same or different, hydrogen or alkyl, wherein $X^5$ and $X^6$ are optionally substituted with one or more, the same or different, $X^{10}$;

$X^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^{10}$ is optionally substituted with one or more, the same or different, $X^{11}$;

$X^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;

$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$; and $R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, n is 2.

In certain embodiments, the compound is 4-(4-(2-hydroxypropan-2-yl)-1H-1,2,3-triazol-1-yl)-N-(2-(2-methyl-1H-indol-3-yl)ethyl)benzamide or salt thereof (TG10-228).

In certain embodiments, compounds have Formula IVA, Formula IVB, or Formula IVC, Formula IVA

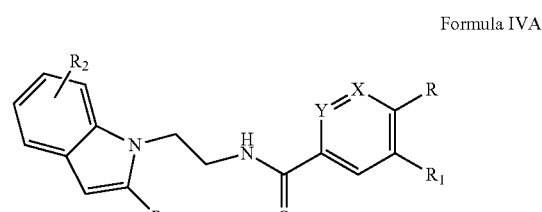

Formula IVB

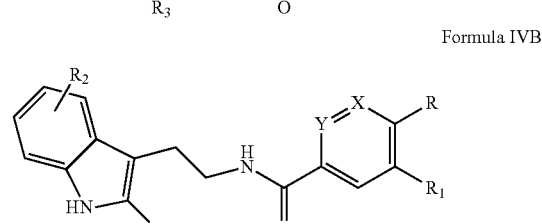

Formula IVC

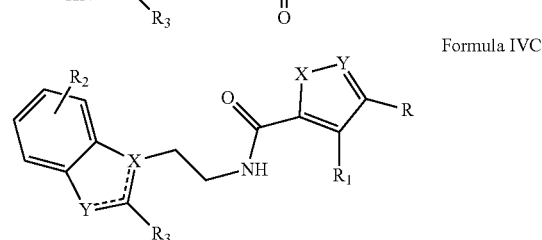

or salts thereof wherein,

R is phenyl ring, substituted-phenyl ring, 5, 6, or 7-membered substituted heterocycles such as pyrrole, pyrazole, imidazole, triazole, tetrazole, morpholine, piperazine, piperidine, thiazoles, and pyridine, pyrimidine, quinoline, isoquinaline or indole;

$R_1$ is hydrogen, alkyl, halogen, and cyano; or R—$R_1$ fused 5-membered or 6 membered heterocyclic rings;

$R_2$ is hydrogen, alkyl, halogen, dihalogen, or any ring structure;

$R_3$=H, F, $CH_3$, $CF_3$, or $NHCH_3$;

X=N or O; and

Y=C, N, O.

In certain embodiments, compounds have Formula IVD or Formula IVE,

Formula IVD

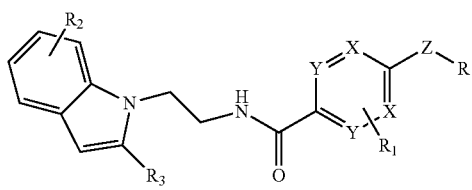

Formula IVE

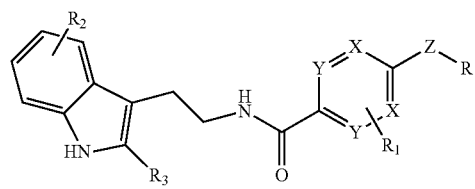

or salts thereof wherein,
R is a phenyl ring, substituted-phenyl ring, 5, 6, or 7-membered substituted heterocycles such as pyrrole, pyrazole, imidazole, triazole, tetrazole, morpholine, piperazine, piperidine, thiazoles, pyridine, pyrimidine, quinoline, isoquinaline, or indole;
$R_1$ is hydrogen, alkyl groups, halogen, or cyano;
$R_2$ is hydrogen, alkyl, halogen, dihalogen, or any ring structure;
$R_3$ is H, $CH_3$, $CF_3$, $CF_2$, $NHCH_3$, or $N(CH_3)_2$;
X is CH or N;
Y is CH or N;
Z=NH, $NHCH_3$, O, S, or $SO_2$.

In certain embodiments, compounds have Formula IVF or Formula IVG,

Formula IVF

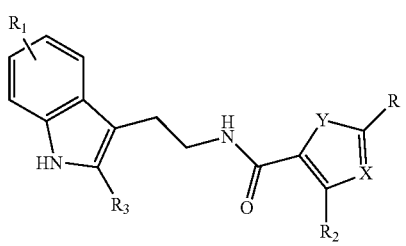

Formula IVG

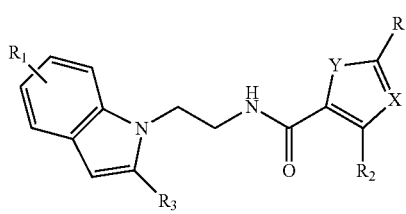

or salts thereof wherein,
R is phenyl, substituted-phenyl, 5, 6 or 7-membered substituted heterocycles such as pyrrole, pyrazole, imidazole, triazole, tetrazole, morpholine, piperazine, piperidine, thiazoles, and pyridine, pyrimidine, quinoline, isoquinaline and indole;
$R^1$ is hydrogen, alkyl, halogen, or cyano;
$R_2$ is hydrogen, alkyl, halogen, $CF_3$, or any ring structure;
$R_3$=H, $CH_3$, $CF_3$, $NHCH_3$, or $N(CH3)_2$;
X is CH, N, or S; and
Y is N or S.

In certain embodiments, compounds have Formula IVH or Formula IVJ,

Formula IVH

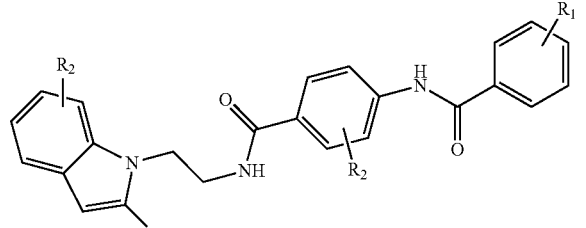

Formula IVJ

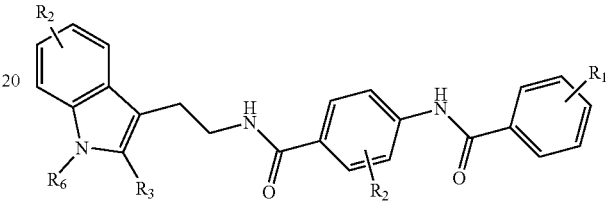

or salts thereof wherein,
$R_1$ is hydrogen, alkyl, halogen, or cyano;
$R_2$ is hydrogen, alkyl, halogen, dihalogen, or any ring structure;
$R_3$ is H, $CH_3$, $CF_3$, or $NHCH_3$; and
$R_6$ is H, $CH_3$, benzoyl, flurobenzoyl, benzyl, or substituted benzyl group.

In certain embodiments, compounds have Formula IVK

Formula IVK

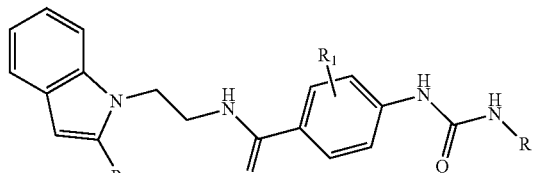

or salts thereof wherein,
R is phenyl, substituted phenyl, cyclic ring, or heterocyclic ring;
$R_1$ is hydrogen, alkyl, halogen, or cyano; and
$R_3$ is H, $CH_3$, $CF_3$, or $NHCH_3$.

In certain embodiments, compounds have Formula IVL or Formula IVM,

Formula IVL

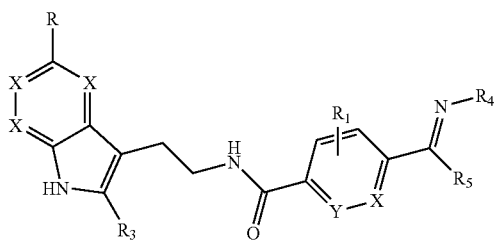

-continued

Formula IVM

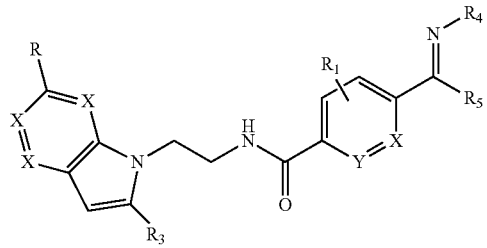

or salts thereof wherein,
X is CH or N;
Y is CH or N:
R is H, CH$_3$, CF$_3$, CN, alkyl, or aryl;
R$_1$ is hydrogen, alkyl, halogen, or cyano;
R$_3$ is H, CH$_3$, CF$_3$, or NHCH$_3$;
R$_4$ is OH, NH$_2$, or OCH$_3$;
R$_5$ is CH$_3$, CF$_3$, phenyl, or aryl;
X is CH or N; and
Y is CH or N.

In certain embodiments, compounds have Formula IVN or Formula IVP,

Formula IVN

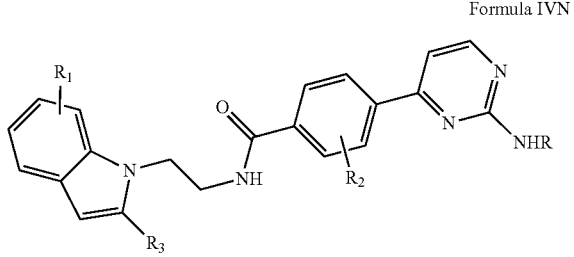

Formula IVP

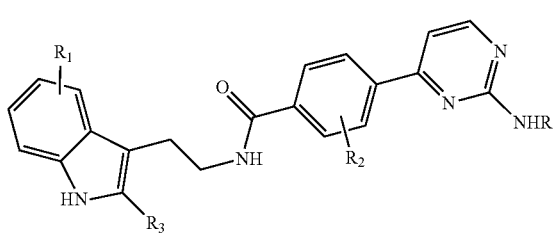

or salts thereof wherein,
R$_1$ is hydrogen, alkyl, halogen, or cyano;
R$_2$ is hydrogen, alkyl, halogen, dihalogen, or any ring structure;
R$_3$ is H, CH$_3$, CF$_3$, or NHCH$_3$; and
R is H, CH$_3$, acetyl, benzoyl, flurobenzoyl, benzyl, or substituted benzyl groups.

In certain embodiments, compounds have Formula IV or Formula IVR,

Formula IVQ

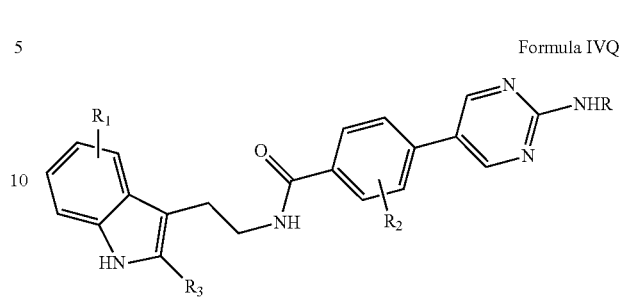

Formula IVR

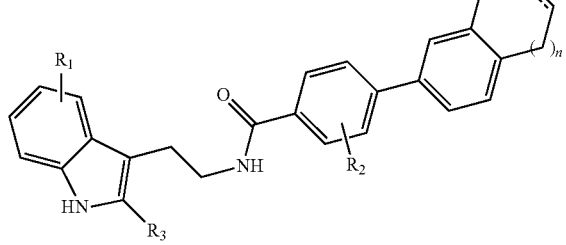

or salts thereof wherein,
n is 0 or 1;
X is NH or C=O;
R$_1$ is hydrogen, alkyl, halogen, or cyano;
R$_2$ is hydrogen, alkyl, halogen, dihalogen, or any ring structure;
R$_3$ is H, CH$_3$, CF$_3$, or NHCH$_3$
R is H, CH$_3$, acetyl, benzoyl, flurobenzoyl, benzyl, or substituted benzyl.

In certain embodiments, compounds have Formula IVS,

Formula IVS

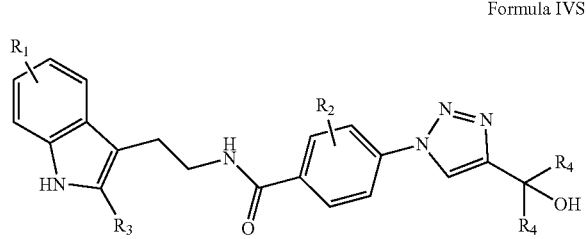

or salts thereof wherein,
R$_1$ is hydrogen, alkyl, halogen, or cyano;
R$_2$ is H, F, CF$_3$, or dihalogen;
R$_3$ is H, CH$_3$, CF$_3$, or NHCH$_3$; and
R$_4$ is H, F, or CF$_3$.

In certain embodiments, compounds have Formula IVT,

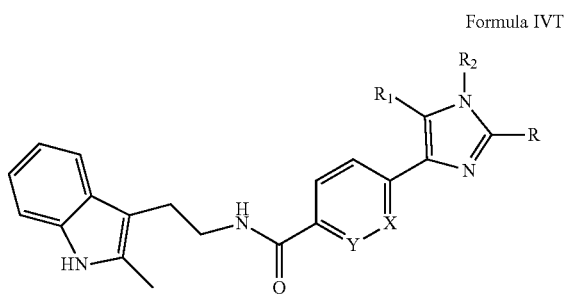

Formula IVT or salts thereof wherein,
R is hydrogen, alkyl, halogen, or cyano;
$R_1$ is hydrogen, alkyl, halogen, or cyano;
$R_2$ is $CH_3$, $CF_3$, or alkyl;
X is CH or N; and
Y is CH or N.

Additional compounds as disclosed herein are shown in FIGS. 2A, 4, 6A-6E, 8A-9D.

Prostaglandin Receptor EP2 Related Diseases and Conditions

Prostaglandin EP2 receptor related diseases or conditions include neurological disorders, brain injury, neuropathic pain, hypertension, ischemic injury, neuroinflammation after a seizure, rupture of cerebral aneurysms, endometriosis, cancer, inflammatory bowel disease (colitis), arthritis/rheumatoid arthritis, skin inflammation, vascular inflammation, Alzheimer's disease (AD), Parkinson's disease (PD), amyotrophic lateral sclerosis (ALS), kidney disease/transplant rejection, atherosclerosis, ischaemic heart disease, acne vulgaris, asthma, chronic prostatitis, glomerulonephritis, hypersensitivities, inflammatory bowel diseases, pelvic inflammatory disease, sarcoidosis, vasculitis, interstitial cystitis, and other autoimmune diseases.

Neurological disorders, diseases, or conditions contemplated include, brain injury such as brain damage according to cerebral lobe, basal ganglia, cerebellum, brainstem, frontal lobe damage, parietal lobe damage, temporal lobe damage, occipital lobe damage, aphasia, dysarthria, apraxia, agnosia, amnesia, spinal cord disorders, peripheral nervous system disorders, cranial nerve disorders, autonomic nervous system disorders, seizure disorders such as epilepsy, movement disorders such as Parkinson's disease, sleep disorders, headaches (including migraine), lower back and neck pain, neuropathic pain, delirium and dementia such as in Alzheimer's disease, dizziness, vertigo, stupor, coma, stroke (CVA, cerebrovascular attack), multiple sclerosis (MS) and other demyelinating diseases, infections of the brain or spinal cord (including meningitis), prion diseases, and complex regional pain syndrome (CRPS).

Status epilepticus refers to a potentially life-threatening condition in which the brain is in a state of persistent seizure or recurrent seizure typically lasting longer than about 20-30 minutes. It is not intended that time of the seizure be of any specific duration, but typically 30-60 minutes is sufficient to damage neurons and seizures are unlikely to self-terminate by that time. The mortality rate of status epilepticus is high in adults who experience at least 1 hour of status epilepticus (30-37% by 1 month).

In certain embodiments, the compounds or compositions are administered at about 0.5, 1, 2, 3, 4, or 5 hours after a subject has stopped having a seizure, e.g., because the subject was administered an anticonvulsant or an anesthetic.

Examples of why one may experience such a seizure include because they have epilepsy and have stopped taking anticonvulsant medication, a stroke, hemorrhage, or as a result of intoxicants, adverse reactions to drugs, sudden withdrawal from chronic consumption of alcoholic beverages, fasting, trauma to the brain, brain disorders such as, but not limited to, meningitis, encephalitis, brain tumors, abscess. It is contemplated that in certain embodiments, the subject may be in a convulsive status epilipticus for any of the reseasons provided herein.

Status epilepticus may be treated with midazolam, valproate, phenobarbital, thiopental pentobarbital, diazepam or other benzodiazepines such as clonazepam, or lorazepam. If these compounds are ineffective one may administer general anesthetics such as propofol or an NMDA antagonist such as ketamine. In certain embodiments, the disclosure contemplates administering compounds disclosed herein after or in combination with being treated with anticonvulsive agents such as those describe above.

COX-2 and prostanoid products have a role in progression of tumors including lung, head and neck, prostate and colon, ovary and breast, hepatocellular carcinoma. Taking COX-2 inhibitor drugs regularly may reduce the rates of certain cancers and cancer related deaths. Upregulation of COX-2 in tumor tissues has been reported to be accompanied by high levels of $PGE_2$. Moreover, EP2 activation by $PGE_2$ can promote cancer cell growth and invasion by activating iNOS/guanylate cyclase (GC) and mitogen-activated protein kinase (MAPK)-ERK1/2 via PKA-mediated epidermal growth factor (EGF) receptor activation. $PGE_2$/EP2 signaling in mammary epithelial cells triggers hyperplasia of mammary glands and EP2 receptor is an important element for $PGE_2$ regulated vascular endothelial growth factor (VEGF) induction in mouse mammary tumor cells. EP2 signaling directly regulates tumor angiogenesis in endothelium by enhancing endothelial cell motility and cell survival, mediates epidermal hypertrophy and tumor aggression in response to ultraviolet (UV)-irradiation, and induces skin carcinogenesis.

Thus, within certain embodiments, it is contemplated that compounds disclosed herein may be used for the treatment of cancers and tumors of the nervous system including those subjects diagnosed with cancer, including, skin, blood vessel, lung, head and neck, prostate and colon, ovary and breast cancer and hepatocellular carcinoma.

Within certain embodiments, it is contemplated that compounds disclosed herein may be used for the treatment of inflammation generally and autoimmune diseases, such as, but not limited to, encephalomyelitis, leukoencephalitis, Addison's disease, agammaglobulinemia, alopecia areata, amyotrophic lateral sclerosis, ankylosing spondylitis, anti-GBM/TBM nephritis, antiphospholipid syndrome, antisynthetase syndrome, atopic allergy, atopic dermatitis, aplastic anemia, cardiomyopathy, enteropathy, hemolytic anemia, hepatitis, inner ear disease, lymphoproliferative syndrome, peripheral neuropathy, pancreatitis, polyendocrine syndrome, progesterone dermatitis, thrombocytopenic purpura, urticaria, uveitis, Balo disease/Balo, concentric sclerosis, Bechets syndrome, Berger's disease, Bickerstaffs encephalitis, Blau syndrome, Bullous pemphigoid, Castleman's disease, celiac disease, inflammatory demyelinating polyneuropathy, multifocal osteomyelitis, Churg-Strauss syndrome, cicatricial pemphigoid, Cogan syndrome, cold agglutinin disease, complement component 2 deficiency, cranial arteritis, CREST syndrome, Crohns Disease, Cushing's Syndrome, cutaneous leukocytoclastic angiitis, Dego's disease, Dercum's disease Suspected, dermatitis herpetiformis, dermatomyositis, diabetes mellitus type 1, diffuse cutaneous systemic sclerosis, Dressler's syndrome, Discoid lupus, erythematosus, eczema, enthesitis-related arthritis, eosinophilic fasciitis, eosinophilic, gastroenteritis, epidermolysis bullosa acquisita, erythema nodosum, cryoglobulinemia, Evan's syndrome, fibrodysplasia ossificans progressive, fibrosing aveolitis, gastritis, gastrointestinal pemphigoid, giant cell arteritis, glomerulonephritis, Goodpasture's syndrome, Graves' disease, Guillain-Barre syndrome (GBS), Hashimoto's encephalitis, Hashimoto's thyroiditis, haemolytic anaemia, Henoch-Schonlein purpura, herpes gestationis, hypogammaglobulinemia, demyelinating diseases, pulmonary fibrosis, thrombocytopenic purpura, nephropathy, inclusion body myositis, demyelinating polyneuopathy, interstitial cystitis, Kawasaki's Disease, Lambert-Eaton myasthenic syndrome, leukocytoclastic vasculitis, lichen planus, lichen sclerosus, linear IgA disease (LAD), lupoid hepatitis, lupus erythematosus, Majeed syndrome, Ménière's disease, microscopic polyangiitis, Miller-Fisher syndrome, mixed connective tissue disease, morphea, Mucha-Habermann disease, multiple sclerosis, myasthenia gravis, myositis, meuromyelitis optica, neuromyotonia, occular cicatricial pemphigoid, psoclonus myoclonus syndrome, ord thyroiditis, palindromic rheumatism, PANDAS (pediatric autoimmune neuropsychiatric disorders associated with streptococcus), paraneoplastic cerebellar degeneration, paroxysmal nocturnal hemoglobinuria (PNH), Parry Romberg syndrome, Parsonnage-Turner syndrome, Pars planitis, pemphigus pernicious anaemia, perivenous encephalomyelitis, POEMS syndrome, polyarteritis nodosa, polymyalgia rheumatic, polymyositis, primary biliary cirrhosis, primary sclerosing cholangitis, progressive inflammatory neuropathy, psoriasis Accepted, psoriatic arthritis, pyoderma gangrenosum, pure red cell aplasia, Rasmussen's encephalitis, Raynaud phenomenon, relapsing polychondritis, Reiter's syndrome, Restless leg syndrome, retroperitoneal fibrosis, rheumatoid arthritis, rheumatoid fever, sarcoidosis, Schmidt syndrome, Schnitzler syndrome, scleritis, scleroderma, Sjögren's syndrome, spondyloarthropathy, Still's disease, stiff person syndrome, subacute bacterial endocarditis (SBE), Susac's syndrome, Sweet's syndrome, sydenham chorea, sympathetic ophthalmia, Takayasu's arteritis, temporal arteritis, Tolosa-Hunt syndrome, transverse myelitis, ulcerative colitis, undifferentiated connective tissue disease, undifferentiated spondyloarthropathy, vasculitis, vitiligo, and Wegener's granulomatosis.

Further provided herein are methods of treating cancer in a subject, comprising administering to the subject an effective amount of a compound or composition as disclosed herein. Methods of killing a tumor cell are also provided herein. The methods comprise contacting a tumor cell with an effective amount of a compound or composition as disclosed herein. The methods can further include administering a second compound or composition (e.g., an anticancer agent) or administering an effective amount of ionizing radiation to the subject. Exemplary cancers that can be treated include, but are not limited to, cancer and/or tumors of the anus, bile duct, bladder, bone, bone marrow, bowel (including colon and rectum), breast, eye, gall bladder, kidney, mouth, larynx, esophagus, stomach, testis, cervix, head, neck, ovary, lung, mesothelioma, neuroendocrine, penis, skin, spinal cord, thyroid, vagina, vulva, uterus, liver, muscle, pancreas, prostate, blood cells (including lymphocytes and other immune system cells), and brain. Specific cancers contemplated for treatment include carcinomas, Karposi's sarcoma, melanoma, mesothelioma, soft tissue sarcoma, pancreatic cancer, lung cancer, leukemia (acute lymphoblastic, acute myeloid, chronic lymphocytic, chronic myeloid, and other), and lymphoma (Hodgkin's and non-Hodgkin's), and multiple myeloma.

Formulations

Pharmaceutical compositions disclosed herein may be in the form of pharmaceutically acceptable salts, as generally described below. Some non-limiting examples of suitable pharmaceutically acceptable organic and/or inorganic acids are hydrochloric acid, hydrobromic acid, sulfuric acid, nitric acid, acetic acid and citric acid, as well as other pharmaceutically acceptable acids known per se (for which reference is made to the references referred to below).

When the compounds of the disclosure contain an acidic group as well as a basic group, the compounds of the disclosure may also form internal salts, and such compounds are within the scope of the disclosure. When a compound contains a hydrogen-donating heteroatom (e.g. NH), salts are contemplated to covers isomers formed by transfer of said hydrogen atom to a basic group or atom within the molecule.

Pharmaceutically acceptable salts of the compounds include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts. For a review on suitable salts, see Handbook of Pharmaceutical Salts: Properties, Selection, and Use by Stahl and Wermuth (Wiley-VCH, 2002), incorporated herein by reference.

The compounds described herein may be administered in the form of prodrugs. A prodrug can include a covalently bonded carrier which releases the active parent drug when administered to a mammalian subject. Prodrugs can be prepared by modifying functional groups present in the compounds in such a way that the modifications are cleaved, either in routine manipulation or in vivo, to the parent compounds. Prodrugs include, for example, compounds wherein a hydroxyl group is bonded to any group that, when administered to a mammalian subject, cleaves to form a free hydroxyl group. Examples of prodrugs include, but are not limited to, acetate, formate and benzoate derivatives of alcohol functional groups in the compounds. Methods of structuring a compound as prodrugs can be found in the book of Testa and Mayer, Hydrolysis in Drug and Prodrug Metabolism, Wiley (2006). Typical prodrugs form the active metabolite by transformation of the prodrug by hydrolytic enzymes, the hydrolysis of amide, lactams, peptides, carboxylic acid esters, epoxides or the cleavage of esters of inorganic acids.

Pharmaceutical compositions for use in the present disclosure typically comprise an effective amount of a compound and a suitable pharmaceutical acceptable carrier. The preparations may be prepared in a manner known per se, which usually involves mixing the at least one compound according to the disclosure with the one or more pharmaceutically acceptable carriers, and, if desired, in combination with other pharmaceutical active compounds, when necessary under aseptic conditions. Reference is again made to U.S. Pat. Nos. 6,372,778, 6,369,086, 6,369,087 and 6,372,733 and the further references mentioned above, as well as to the standard handbooks, such as the latest edition of Remington's Pharmaceutical Sciences.

Generally, for pharmaceutical use, the compounds may be formulated as a pharmaceutical preparation comprising at least one compound and at least one pharmaceutically acceptable carrier, diluent or excipient and/or adjuvant, and optionally one or more further pharmaceutically active compounds.

The pharmaceutical preparations of the disclosure are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, of the at least one compound of the disclosure, e.g. about 10, 25, 50, 100, 200, 300 or 400 mg per unit dosage.

The compounds can be administered by a variety of routes including the oral, ocular, rectal, transdermal, subcutaneous, intravenous, intramuscular or intranasal routes, depending mainly on the specific preparation used. The compound will generally be administered in an "effective amount", by which is meant any amount of a compound that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram body weight of the patient per day, more often between 0.1 and 500 mg, such as between 1 and 250 mg, for example about 5, 10, 20, 50, 100, 150, 200 or 250 mg, per kilogram body weight of the patient per day, which may be administered as a single daily dose, divided over one or more daily doses. The amount(s) to be administered, the route of administration and the further treatment regimen may be determined by the treating clinician, depending on factors such as the age, gender and general condition of the patient and the nature and severity of the disease/symptoms to be treated. Reference is again made to U.S. Pat. Nos. 6,372,778, 6,369,086, 6,369,087 and 6,372,733 and the further references mentioned above, as well as to the standard handbooks, such as the latest edition of Remington's Pharmaceutical Sciences.

Depending upon the manner of introduction, the compounds described herein may be formulated in a variety of ways. Formulations containing one or more inhibitors can be prepared in various pharmaceutical forms, such as granules, tablets, capsules, suppositories, powders, controlled release formulations, suspensions, emulsions, creams, gels, ointments, salves, lotions, or aerosols and the like. Preferably, these formulations are employed in solid dosage forms suitable for simple, and preferably oral, administration of precise dosages. Solid dosage forms for oral administration include, but are not limited to, tablets, soft or hard gelatin or non-gelatin capsules, and caplets. However, liquid dosage forms, such as solutions, syrups, suspension, shakes, etc. can also be utilized. In another embodiment, the formulation is administered topically. Suitable topical formulations include, but are not limited to, lotions, ointments, creams, and gels. In a preferred embodiment, the topical formulation is a gel. In another embodiment, the formulation is administered intranasally.

Formulations containing one or more of the compounds described herein may be prepared using a pharmaceutically acceptable carrier composed of materials that are considered safe and effective and may be administered to an individual without causing undesirable biological side effects or unwanted interactions. The carrier is all components present in the pharmaceutical formulation other than the active ingredient or ingredients. As generally used herein "carrier" includes, but is not limited to, diluents, binders, lubricants, disintegrators, fillers, pH modifying agents, preservatives, antioxidants, solubility enhancers, and coating compositions.

Carrier also includes all components of the coating composition which may include plasticizers, pigments, colorants, stabilizing agents, and glidants. Delayed release, extended release, and/or pulsatile release dosage formulations may be prepared as described in standard references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, MD, 2000, and "Pharmaceutical dosage forms and drug delivery systems", 6th Edition, Ansel et al., (Media, PA: Williams and Wilkins, 1995). These references provide information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Additionally, the coating material may contain conventional carriers such as plasticizers, pigments, colorants, glidants, stabilization agents, pore formers and surfactants.

Optional pharmaceutically acceptable excipients present in the drug-containing tablets, beads, granules or particles include, but are not limited to, diluents, binders, lubricants, disintegrants, colorants, stabilizers, and surfactants. Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross-linked polymers, such as cross-linked PVP (Polyplasdone XL from GAF Chemical Corp).

Stabilizers are used to inhibit or retard drug decomposition reactions which include, by way of example, oxidative reactions.

Surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-beta-alanine, sodium N-lauryl-beta-iminodipropionate, myristoamphoacetate, lauryl betaine and lauryl sulfobetaine.

If desired, the tablets, beads, granules, or particles may also contain minor amount of nontoxic auxiliary substances such as wetting or emulsifying agents, dyes, pH buffering agents, or preservatives.

The concentration of the inhibitor(s) to carrier and/or other substances may vary from about 0.5 to about 100 wt. % (weight percent). For oral use, the pharmaceutical formulation will generally contain from about 5 to about 100% by weight of the active material. For other uses, the pharmaceutical formulation will generally have from about 0.5 to about 50 wt. % of the active material.

The compositions described herein can be formulation for modified or controlled release. Examples of controlled release dosage forms include extended release dosage forms, delayed release dosage forms, pulsatile release dosage forms, and combinations thereof.

The extended release formulations are generally prepared as diffusion or osmotic systems, for example, as described in "Remington—The science and practice of pharmacy" (20th ed., Lippincott Williams & Wilkins, Baltimore, MD, 2000). A diffusion system typically consists of two types of devices, a reservoir and a matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkylcelluloses such as hydroxypropyl-cellulose, hydroxypropylmethylcellulose, sodium carboxymethylcellulose, and Carbopol™ 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

In certain preferred embodiments, the plastic material is a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly (methacrylic acid), methacrylic acid alkylamine copolymer poly(methyl methacrylate), poly(methacrylic acidxanhydride), polymethacrylate, polyacrylamide, poly(methacrylic acid anhydride), and glycidyl methacrylate copolymers.

In certain preferred embodiments, the acrylic polymer is comprised of one or more ammonio methacrylate copolymers. In one preferred embodiment, the acrylic polymer is an acrylic resin lacquer such as that which is commercially available from Rohm Pharma under the tradename Eudragit™ In further preferred embodiments, the acrylic polymer comprises a mixture of two acrylic resin lacquers commercially available from Rohm Pharma under the tradenames Eudragit™ RL30D and Eudragit™ RS30D, respectively. Eudragit™ RL30D and Eudragit™ RS30D are copolymers of acrylic and methacrylic esters with a low content of quaternary ammonium groups, the molar ratio of ammonium groups to the remaining neutral (meth)acrylic esters being 1:20 in Eudragit™ RL30D and 1:40 in Eudragit™ RS30D. The mean molecular weight is about 150,000. Eudragit™ S-100 and Eudragit™ L-100 are also preferred. The code designations RL (high permeability) and RS (low permeability) refer to the permeability properties of these agents. Eudragit™ RL/RS mixtures are insoluble in water and in digestive fluids. However, multiparticulate systems formed to include the same are swellable and permeable in aqueous solutions and digestive fluids.

The polymers described above such as Eudragit™ RL/RS may be mixed together in any desired ratio in order to ultimately obtain a sustained-release formulation having a desirable dissolution profile. Desirable sustained-release multiparticulate systems may be obtained, for instance, from 100% Eudragit™ RL, 50% Eudragit™ RL and 50% Eudragit™ RS, and 10% Eudragit™ RL and 90°/Eudragit™ RS. One skilled in the art will recognize that other acrylic polymers may also be used, such as, for example, Eudragit™ L.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above can be combined in a final dosage form comprising single or multiple units. Examples of multiple units include, but are not limited to, multilayer tablets and capsules containing tablets, beads, or granules An immediate release portion can be added to the extended release system by means of either applying an immediate release layer on top of the extended release core using a coating or compression process or in a multiple unit system such as a capsule containing extended and immediate release beads.

Extended release tablets containing hydrophilic polymers are prepared by techniques commonly known in the art such as direct compression, wet granulation, or dry granulation. Their formulations usually incorporate polymers, diluents, binders, and lubricants as well as the active pharmaceutical ingredient. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful.

Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In congealing method, the drug is mixed with a wax material and either spray-congealed or congealed and screened and processed.

Delayed release formulations are created by coating a solid dosage form with a polymer film, which is insoluble in the acidic environment of the stomach, and soluble in the neutral environment of the small intestine.

The delayed release dosage units can be prepared, for example, by coating a drug or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename Eudragit® (Rohm Pharma; Westerstadt, Germany), including Eudragit® L30D-55 and L100-55 (soluble at pH 5.5 and above), Eudragit® L-100 (soluble at pH 6.0 and above), Eudragit™ S (soluble at pH 7.0 and above, as a result of a higher degree of esterification), and Eudragits™ NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multi-layer coatings using different polymers may also be applied.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition may include conventional additives, such as plasticizers, pigments, colorants, stabilizing agents, glidants, etc. A plasticizer is normally present to reduce the fragility of the coating and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

The formulation can provide pulsatile delivery of the one or more inhibitors. By "pulsatile" is meant that a plurality of drug doses are released at spaced apart intervals of time. Generally, upon ingestion of the dosage form, release of the initial dose is substantially immediate, i.e., the first drug release "pulse" occurs within about one hour of ingestion. This initial pulse is followed by a first time interval (lag time) during which very little or no drug is released from the dosage form, after which a second dose is then released. Similarly, a second nearly drug release-free interval between the second and third drug release pulses may be designed. The duration of the nearly drug release-free time interval will vary depending upon the dosage form design e.g., a twice daily dosing profile, a three times daily dosing profile, etc. For dosage forms providing a twice daily dosage profile, the nearly drug release-free interval has a duration of approximately 3 hours to 14 hours between the first and second dose. For dosage forms providing a three times daily profile, the nearly drug release-free interval has a duration of approximately 2 hours to 8 hours between each of the three doses.

In one embodiment, the pulsatile release profile is achieved with dosage forms that are closed and preferably sealed capsules housing at least two drug-containing "dosage units" wherein each dosage unit within the capsule provides a different drug release profile. Control of the delayed release dosage unit(s) is accomplished by a controlled release polymer coating on the dosage unit, or by incorporation of the active agent in a controlled release polymer matrix. Each dosage unit may comprise a compressed or molded tablet, wherein each tablet within the capsule provides a different drug release profile. For dosage forms mimicking a twice a day dosing profile, a first tablet releases drug substantially immediately following ingestion of the dosage form, while a second tablet releases drug approximately 3 hours to less than 14 hours following ingestion of the dosage form. For dosage forms mimicking a three times daily dosing profile, a first tablet releases drug substantially immediately following ingestion of the dosage form, a second tablet releases drug approximately 3 hours to less than 10 hours following ingestion of the dosage form, and the third tablet releases drug at least 5 hours to approximately 18 hours following ingestion of the dosage form. It is possible that the dosage form includes more than three tablets. While the dosage form will not generally include more than a third tablet, dosage forms housing more than three tablets can be utilized.

Alternatively, each dosage unit in the capsule may comprise a plurality of drug-containing beads, granules or particles. As is known in the art, drug-containing "beads" refer to beads made with drug and one or more excipients or polymers. Drug-containing beads can be produced by applying drug to an inert support, e.g., inert sugar beads coated with drug or by creating a "core" comprising both drug and one or more excipients. As is also known, drug-containing "granules" and "particles" comprise drug particles that may or may not include one or more additional excipients or polymers. In contrast to drug-containing beads, granules and particles do not contain an inert support. Granules generally comprise drug particles and require further processing. Generally, particles are smaller than granules, and are not further processed. Although beads, granules and particles may be formulated to provide immediate release, beads and granules are generally employed to provide delayed release.

In one embodiment, the compound is formulated for topical administration. Suitable topical dosage forms include lotions, creams, ointments, and gels. A "gel" is a semisolid system containing a dispersion of the active agent, i.e., inhibitor, in a liquid vehicle that is rendered semisolid by the action of a thickening agent or polymeric material dissolved or suspended in the liquid vehicle. The liquid may include a lipophilic component, an aqueous component or both. Some emulsions may be gels or otherwise include a gel component. Some gels, however, are not emulsions because they do not contain a homogenized blend of immiscible components. Methods for preparing lotions, creams, ointments, and gels are well known in the art.

The compounds described herein can be administered adjunctively with other active compounds. These compounds include but are not limited to analgesics, anti-inflammatory drugs, antipyretics, antidepressants, antiepileptics, antihistamines, antimigraine drugs, antimuscarinics, anxioltyics, sedatives, hypnotics, antipsychotics, bronchodilators, anti-asthma drugs, cardiovascular drugs, corticosteroids, dopaminergics, electrolytes, gastro-intestinal drugs, muscle relaxants, nutritional agents, vitamins, parasympathomimetics, stimulants, anorectics and anti-narcoleptics. "Adjunctive administration", as used herein, means the inhibitors can be administered in the same dosage form or in separate dosage forms with one or more other active agents.

Specific examples of compounds that can be adjunctively administered with the compounds include, but are not limited to, aceclofenac, acetaminophen, adomexetine, almotriptan, alprazolam, amantadine, amcinonide, aminocyclopropane, amitriptyline, amolodipine, amoxapine, amphetamine, aripiprazole, aspirin, atomoxetine, azasetron, azatadine, beclomethasone, benactyzine, benoxaprofen, bermoprofen, betamethasone, bicifadine, bromocriptine, budesonide, buprenorphine, bupropion, buspirone, butorphanol, butriptyline, caffeine, carbamazepine, carbidopa, carisoprodol, celecoxib, chlordiazepoxide, chlorpromazine, choline salicylate, citalopram, clomipramine, clonazepam, clonidine, clonitazene, clorazepate, clotiazepam, cloxazolam, clozapine, codeine, corticosterone, cortisone, cyclobenzaprine, cyproheptadine, demexiptiline, desipramine, desomorphine, dexamethasone, dexanabinol, dextroamphetamine sulfate, dextromoramide, dextropropoxyphene, dezocine, diazepam, dibenzepin, diclofenac sodium, diflunisal, dihydrocodeine, dihydroergotamine, dihydromorphine, dimetacrine, divalproxex, dizatriptan, dolasetron, donepezil, dothiepin, doxepin, duloxetine, ergotamine, escitalopram, estazolam, ethosuximide, etodolac, femoxetine, fenamates, fenoprofen, fentanyl, fludiazepam, fluoxetine, fluphenazine, flurazepam, flurbiprofen, flutazolam, fluvoxamine, frovatriptan, gabapentin, galantamine, gepirone, ginko bilboa, granisetron, haloperidol, huperzine A, hydrocodone, hydrocortisone, hydromorphone, hydroxyzine, ibuprofen, imipramine, indiplon, indomethacin, indoprofen, iprindole, ipsapirone, ketaserin, ketoprofen, ketorolac, lesopitron, levodopa, lipase, lofepramine, lorazepam, loxapine, maprotiline, mazindol, mefenamic acid, melatonin, melitracen, memantine, meperidine, meprobamate, mesalamine, metapramine, metaxalone, methadone, methadone, methamphetamine, methocarbamol, methyldopa, methylphenidate, methylsalicylate, methysergid(e), metoclopramide, mianserin, mifepristone, milnacipran, minaprine, mirtazapine, moclobemide, modafinil (an anti-narcoleptic), molindone, morphine, morphine hydrochloride, nabumetone, nadolol, naproxen, naratriptan, nefazodone, neurontin, nomifensine, nortriptyline, olanzapine, olsalazine, ondansetron, opipramol, orphenadrine, oxaflozane, oxaprazin, oxazepam, oxitriptan, oxycodone, oxymorphone, pancrelipase, parecoxib, paroxetine, pemoline, pentazocine, pepsin, perphenazine, phenacetin, phendimetrazine, phenmetrazine, phenylbutazone, phenytoin, phosphatidylserine, pimozide, pirlindole, piroxicam, pizotifen, pizotyline, pramipexole, prednisolone, prednisone, pregabalin, propanolol, propizepine, propoxyphene, protriptyline, quazepam, quinupramine, reboxitine, reserpine, risperidone, ritanserin, rivastigmine, rizatriptan, rofecoxib, ropinirole, rotigotine, salsalate, sertraline, sibutramine, sildenafil, sulfasalazine, sulindac, sumatriptan, tacrine, temazepam, tetrabenozine, thiazides, thioridazine, thiothixene, tiapride, tiasipirone, tizanidine, tofenacin, tolmetin, toloxatone, topiramate, tramadol, trazodone, triazolam, trifluoperazine, trimethobenzamide, trimipramine, tropisetron, valdecoxib, valproic acid, venlafaxine, viloxazine, vitamin E, zimeldine, ziprasidone, zolmitriptan, zolpidem, zopiclone and isomers, salts, and combinations thereof.

The additional active agent(s) can be formulated for immediate release, controlled release, or combinations thereof.

EXAMPLES

To further illustrate the principles of the present disclosure, the following examples are put forth so as to provide those of ordinary skill in the art with a complete disclosure and description of how the compositions, articles, and methods claimed herein are made and evaluated. They are intended to be purely exemplary of the invention and are not intended to limit the scope of what the inventors regard as their disclosure. Efforts have been made to ensure accuracy with respect to numbers (e.g., amounts, temperatures, etc.); however, some errors and deviations should be accounted for. Unless indicated otherwise, temperature is ° C. or is at ambient temperature, and pressure is at or near atmospheric. There are numerous variations and combinations of process conditions that can be used to optimize product quality and performance. Only reasonable and routine experimentation will be required to optimize such process conditions.
General Synthetic Procedures:

Proton NMR spectra were recorded in solvent in DMSO-$d_6$/CDCl$_3$ on Varian and Inova-400 (400 MHz). Thin layer chromatography was performed on pre-coated, aluminum-backed plates (silica gel 60 $F_{254}$, 0.25 mm thickness) from EM Science and was visualized by UV lamp, PMA solution and ninhydrin. Chemicals and drugs: PGE$_2$, BW245C, iloprost, and rolipram were purchased from Cayman Chemical. LPS was purchased form Sigma-Aldrich.—Column chromatography was performed with silica gel cartridges on Teledyne-ISCO instrument. Agilent LC-MS was used to determine the mass and purity of the products. LC-MS conditions: Mobile phase A: methanol (0.1% acetic acid); mobile phase B: water (0.1% acetic acid); column: ZORBAX Eclipse XDB C18 5 µM, 4.6×150 mm. Gradient B 80% at 0 min, linearly decreased to 5% by 7 min, and then linear increase to 40% by 12 min; UV wavelength=254 nm; flow rate=1 mL/min. Furthermore, purity of several key compounds is determined by Water's HPLC instrument. HPLC Conditions: Mobile phase A: water (0.1% trifluoroacetic acid); mobile phase B: acetonitrile (0.1% trifluoroacetic acid); column: XBridge C18 5 µM, 4.6×150 mm; gradient: 10% B at 0 min, increased linearly to 90% by 10 min, then decreased to 10% by 12 min; UV wavelength=230 nm; flow rate=1 mL/min. Compounds with >95% purity by HPLC were tested in cellular bioassays and DMPK properties. Compounds 7a (Salikov, R. F., et al., Branching Tryptamines as a Tool to Tune Their Antiproliferative Activity. *Eur. J. Med. Chem.* 2018, 144, 211-217), 7b (Baggett, A. W., et al., Structural Characterization and Computer-Aided Optimization of a Small-Molecule Inhibitor of the Arp2/3 Complex, a Key Regulator of the Actin Cytoskeleton. *ChemMedChem* 2012, 7, 1286-1294), 7e (Liang, X.-W., et al., Asymmetric Fluorinative Dearomatization of Tryptamine Derivatives. *ChemComm* 2017, 53, 5531-5534) were reported in the literature and the characterization data for these derivatives was in good agreement with the literature data. The compound 2-(2-(trifluoromethyl)-1H-indol-3-yl)ethan-1-amine (7f) was synthesized as reported before (Shevchenko, N. E., et al., Practical Synthesis of A-Perfluoroalkyl Cyclic Imines and Amines. *Synthesis* 2010, 120-126; Shmatova, O. I., et al., Fischer Reaction with 2-Perfluoroalkylated Cyclic Imines—an Efficient Route to 2-Perfluoroalkyl-Substituted Tryptamines and Their Derivatives and Homologues. *Eur. J. Org. Chem.* 2015, 6479-6488) and 2-(2-methylpyrazolo[1,5-a]pyridin-3-yl)ethan-1-amine (7g) was synthesized following the literature procedure (Shultz, M. D., et al., Optimization of the in vitro Cardiac Safety of Hydroxamate-Based Histone Deacetylase Inhibitors. *J. Med. Chem.* 2011, 54, 4752-4772). 2-Amino-1-(2-methyl-1H-indol-3-yl)ethan-1-one (7h), and 2-amino-1-(2-methyl-1H-indol-3-yl)ethan-1-ol (7i) were commercially available.
Cell Culture.

The rat C6 glioma (C6G) cells stably expressing human DP1, EP2, EP4, or IP receptors were created in the laboratory (Jiang, J., et al. Inhibition of the Prostaglandin Receptor EP2 Following Status Epilepticus Reduces Delayed Mortality and Brain Inflammation. *Proc. Natl. Acad. Sci. U.S.A.* 2013, 110, 3591-3596; Jiang, J., et al., Small Molecule Antagonist Reveals Seizure-Induced Mediation of Neuronal Injury by Prostaglandin E2 Receptor Subtype EP2. *Proc. Natl. Acad. Sci. U.S.A.* 2012, 109, 3149-3154; Jiang, J., et al., Neuroprotection by Selective Allosteric Potentiators of the EP2 Prostaglandin Receptor. *Proc. Natl. Acad. Sci. U.S.A.* 2010, 107, 2307-2312 and grown in Dulbecco's Modified Eagle Medium (DMEM) (Invitrogen) supplemented with 10% (v/v) fetal bovine serum (FBS) (Invitrogen), 100 U/mL penicillin, 100 µg/mL streptomycin (Invitrogen), and 0.5 µg/mL G418 (Invitrogen).
Cell-Based cAMP Assay.

Intracellular cAMP was measured with a cell-based homogeneous time-resolved fluorescence resonance energy transfer (TR-FRET) method (Cisbio Bioassays), as previously described (Jiang, J., et al. Inhibition of the Prostaglandin Receptor EP2 Following Status Epilepticus Reduces Delayed Mortality and Brain Inflammation. *Proc. Natl. Acad. Sci. U.S.A.* 2013, 110, 3591-3596; Jiang, J., et al., Small Molecule Antagonist Reveals Seizure-Induced Mediation of Neuronal Injury by Prostaglandin E2 Receptor Subtype EP2. *Proc. Natl. Acad. Sci. U.S.A.* 2012, 109, 3149-3154). The assay is based on generation of a strong FRET signal upon the interaction of two molecules, an anti-cAMP antibody coupled to a FRET donor (Cryptate) and cAMP coupled to a FRET acceptor (d2). Endogenous cAMP produced by cells competes with labeled cAMP for binding to the cAMP antibody and thus reduces the FRET signal. Cells stably expressing human DP1, EP2, EP4, or IP receptors were seeded into 384-well plates in 30 µL complete medium (4,000 cells/well) and grown overnight. The medium was carefully withdrawn and 10 µL Hanks' Buffered Salt Solution (HBSS) (Hyclone) containing 20 µM rolipram was added into the wells to block phosphodiesterases. The cells were incubated at room temperature for 0.5-1 h and then treated with vehicle or test compound for 10 min before addition of increasing concentrations of appropriate agonist: BW245C for DP1, PGE$_2$ for EP2 and EP4, or iloprost for IP. The cells were incubated at room temperature for 40 min, then lysed in 10 μL lysis buffer containing the FRET acceptor cAMP-d2 and 1 min later another 10 μL lysis buffer with anti-cAMP-Cryptate was added. After 60-90 min incubation at room temperature, the FRET signal was measured by an Envision 2103 Multilabel Plate Reader (PerkinElmer Life Sciences) with a laser excitation at 337 nm and dual emissions at 665 nm and 590 nm for d2 and Cryptate (50 μs delay), respectively. The FRET signal was expressed as: F665/F590×10$^4$.

Procedure for the Synthesis of 2b (TG9-175) and 2c:

To a solution of commercially available acid 1b or 1c (0.4 mmol, 1 equiv.) and 7 (70 mg, 0.4 mmol, 1 equiv.) in mixture of dichloromethane and N,N-dimethylformamide (3 mL, 5:1) was added DMAP (catalytic amount, 2 mg) followed by EDCI·HCl (114 mg, 0.59 mmol, 1.3 equiv.) and the reaction mixture was stirred at room temperature for 10 h. Organic solvent was evaporated and reaction mixture was added a saturated solution of ammonium chloride (5 mL) and extracted with ethyl acetate (3×10 mL). Organic layer was separated and washed with saturated solution of sodium bicarbonate (5 mL) followed by brine solution (5 mL), dried over sodium sulfate and concentrated to dryness. The crude material was purified on silica gel chromatography using 60-70% ethyl acetate in hexanes to get the required product 2b or 2c (Scheme 1).

N-(2-(2-Methyl-1H-indol-3-yl)ethyl)-6-morpholinonicotinamide (2b) (TG9-175)

$^1$H NMR (400 MHz, DMSO-d$_6$): δ 10.69 (s, 1H), 8.59 (d, J=2.0 Hz, 1H), 8.40 (t, J=5.6 Hz, 1H), 7.95 (dd, J=8.9, 2.4 Hz, 1H), 7.44 (d, J=7.6 Hz, 1H), 7.20 (d, J=7.7 Hz, 1H), 6.97-6.85 (m, 2H), 6.81 (d, J=9.0 Hz, 1H), 3.70-3.63 (m, 4H), 3.58-3.47 (m, 4H), 3.37 (q, J=7.1 Hz, 2H), 2.84 (t, J=7.4 Hz, 2H), 2.27 (s, 3H); LCMS (ESI): >97% purity. MS m/z, 365 [M+H]$^+$; HPLC purity: 99.7%.

N-(2-(2-Methyl-1H-indol-3-yl)ethyl)-6-(piperidin-1-yl)nicotinamide (2c)

$^1$H NMR (400 MHz, CDCl$_3$): δ 8.36 (d, J=2.3 Hz, 1H), 8.08 (s, 1H), 7.74 (dd, J=9.0, 2.5 Hz, 1H), 7.51 (d, J=7.5 Hz, 1H), 7.28-7.22 (m, 1H), 7.11-7.08 (m, 2H), 6.54 (d, J=9.0 Hz, 1H), 6.02 (t, J=5.6 Hz, 1H), 3.67 (q, J=6.4 Hz, 2H), 3.57 (d, J=5.0 Hz, 4H), 2.99 (t, J=6.6 Hz, 2H), 2.32 (s, 3H), 1.67-1.56 (m, 6H); LCMS (ESI): >97% purity. MS m/z 363 [M+H]$^+$; HPLC purity: 98.9%.

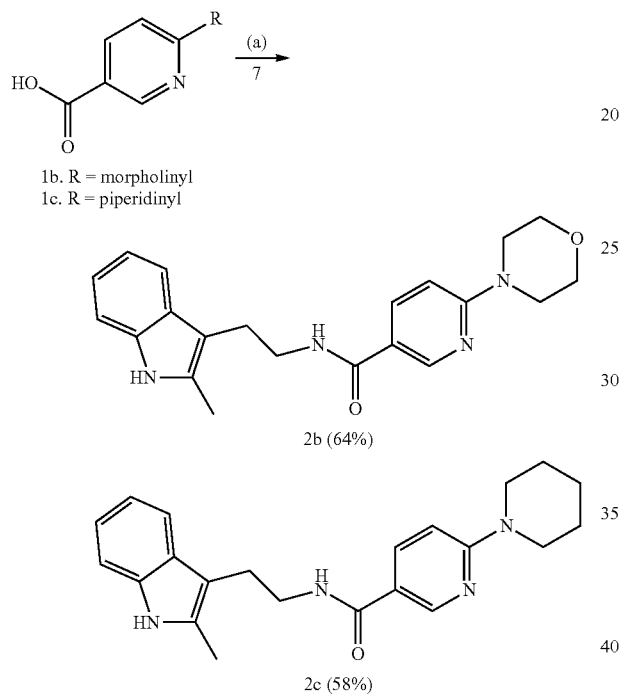

Scheme 1: Synthesis of middle ring modified derivatives 2b and 2c

1b. R = morpholinyl
1c. R = piperidinyl 2b (64%)

2c (58%)

$^a$Reagents and conditions: (a) 7 (see structure in Scheme 2), EDCI•HCl, DMAP, DMF:CH$_2$Cl$_2$ (1:1), RT, 12 h. The product yields are shown in the parenthesis

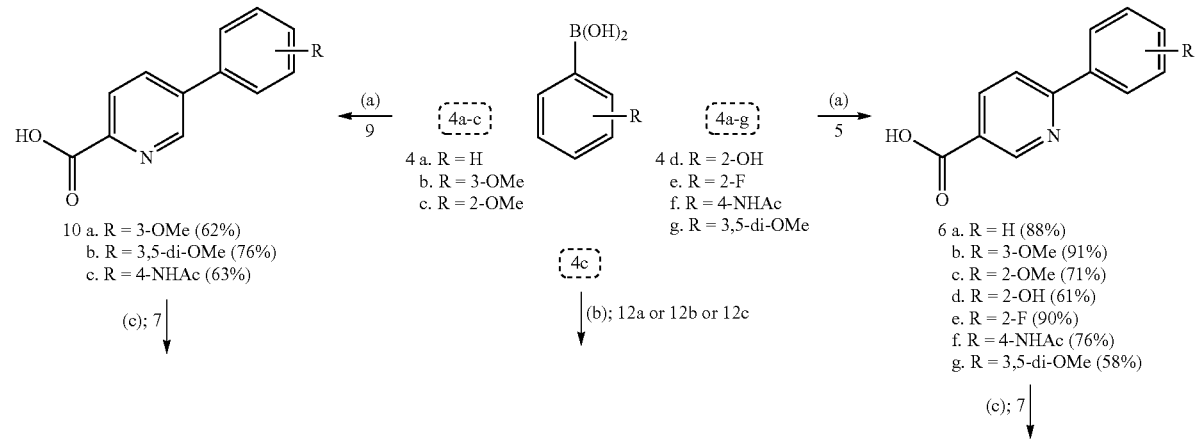

Scheme 2. Synthesis of middle ring modified EP2 antagonist derivatives 10 a. R = 3-OMe (62%)
b. R = 3,5-di-OMe (76%)
c. R = 4-NHAc (63%)

4 a. R = H
b. R = 3-OMe
c. R = 2-OMe 4 d. R = 2-OH
e. R = 2-F
f. R = 4-NHAc
g. R = 3,5-di-OMe 6 a. R = H (88%)
b. R = 3-OMe (91%)
c. R = 2-OMe (71%)
d. R = 2-OH (61%)
e. R = 2-F (90%)
f. R = 4-NHAc (76%)
g. R = 3,5-di-OMe (58%)

-continued

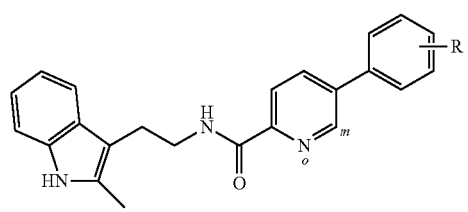

11 a. R = 3-OMe (38%)
b. R = 3,5-di-OMe (76%)
c. R = 4-NHAc (80%)

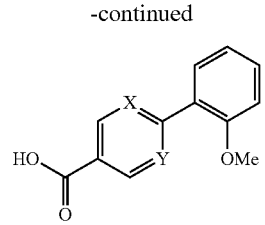

13 a. X, Y = N (25%)
13 b. X = CF, Y = CH (36%)
13 c. X, Y = CH (76%)

↓(c); 7

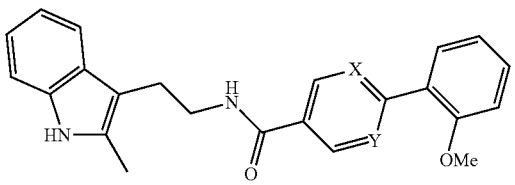

8 a. R = H (71%)
b. R = 3-OMe (74%)
c. R = 2-OMe (69%)
d. R = 2-OH (60%)
e. R = 2-F (70%)
f. R = 4-NHAc (62%)
g. R = 3,5-di-OMe (59%)

14 a. X, Y = N (40%)
b. X = CF, Y = CH (60%)
c. X, Y = CH (83%)

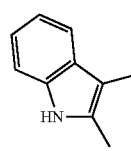 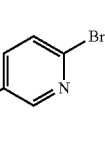 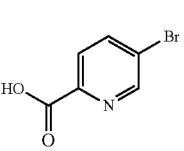 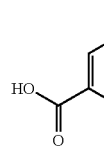 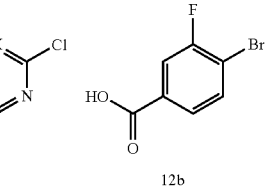 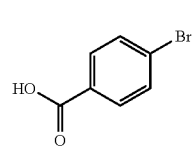

7     5     9     12a     12b     12c

[a]Reagents and conditions: (a) Pd(PPh$_3$)$_4$, Na$_2$CO$_3$ (1M), THF (or) toluene, 100° C., N$_2$; (b) Pd(dppf)Cl$_2$, dioxane:H$_2$O (6:1), Na$_2$CO$_3$, 100° C.;
(c) EDCI·HCl, DMAP, DMF:CH$_2$Cl$_2$ (1:1), rt. Yield for each reaction product is shown in the parenthesis. Yields are isolated yields but are not optimized.

General Procedure for the Synthesis of 6a-g:

A solution of boronic acid (4a-g) (4.1 mmol, 1 equiv.) and bromo-acid, 5 (4.1 mmol, 1 equiv.) in tetrahydrofuran or toluene and water (6:1) were loaded into a sealed tube. To this solution, 1M Na$_2$CO$_3$ (8.2 mmol, 2 equiv.) was added and purged with nitrogen for 10 min. Then, Pd(PPh$_3$)$_4$ (0.2 mmol, 0.05 equiv.) catalyst was added to the reaction mixture, sealed and heated to 100° C. for 12 h. Reaction mixture was cooled to room temperature and solvent was evaporated under vacuum. The residue was washed with dichloromethane to remove organic impurities. Then, aqueous layer was acidified to pH 2 with concentrated HCl to result in white precipitate, which was filtered and dried under vacuum to provide the intermediates (6a, 6b (WO2007008994A2), 6c, 6d (US20080146569A1), 6e (Westway, S. M., et al., Synthesis of 6-Phenylnicotinamide Derivatives as Antagonists of Trpv1. *Bioorg. Med. Chem. Lett.* 2008, 18, 5609-5613), 6f and 6g).

6-Phenylnicotinic acid (6a)

$^1$H NMR (400 MHz, DMSO-d$_6$): δ 13.36 (s, 1H), 9.24-9.03 (m, 1H), 8.35-8.31 (m, 1H), 8.17 (dd, J=8.2, 1.3 Hz, 2H), 8.14-8.09 (m, 1H), 7.54-7.52 (m, 3H). LCMS (ESI): >95% purity; MS m/z, 198 [M−H]$^+$.

6-(2-Methoxyphenyl)nicotinic acid (6c)

$^1$H NMR (300 MHz, DMSO-d$_6$): δ 12.52 (s, 1H), 9.14 (d, J=2.2 Hz, 1H), 8.46 (dd, J=8.4, 2.2 Hz, 1H), 8.11 (d, J=8.3 Hz, 1H), 7.79 (dd, J=7.7, 1.7 Hz, 1H), 7.59-7.47 (m, 1H), 7.23 (d, J=8.2 Hz, 1H), 7.12 (dd, J=11.5, 4.2 Hz, 1H), 3.87 (s, 3H). LCMS (ESI): >95% purity; MS m/z, 228 [M−H]$^+$.

6-(4-Acetamidophenyl)nicotinic acid (6f)

$^1$H NMR (300 MHz DMSO-d$_6$): δ 13.32 (s, 1H), 10.17 (s, 1H), 9.08 (s, 1H), 8.26 (d, J=6.5 Hz, 1H), 8.11 (d, J=8.6 Hz, 2H), 8.02 (d, J=8.3 Hz, 1H), 7.72 (d, J=8.6 Hz, 2H), 2.06 (s, 3H). LCMS (ESI): >97% purity; MS m/z, 255 [M−H]$^+$.

6-(3,5-Dimethoxyphenyl)nicotinic acid (6g)

$^1$H NMR (300 MHz, DMSO-d$_6$): δ 13.31 (bs, 1H), 9.11 (d, J=2.2 Hz, 1H), 8.29 (dd, J=8.3, 2.2 Hz, 1H), 8.12 (d, J=8.4 Hz, 1H), 7.30 (d, J=2.3 Hz, 2H), 6.61 (t, J=2.2 Hz, 1H), 3.81 (s, 6H). LCMS (ESI): >95% purity; MS m/z, 258 [M−H]$^+$.

General Procedure for the Synthesis of Substituted 3-Indole-Ethylamines 7a-g:

To a solution of 25a-e (2 mmol, 1 equiv.) in acetonitrile (20 mL) was added cyclopropyl methyl ketone (4 mmol, 2 equiv.) and refluxed for 24 h. Then, reaction mixtures were cooled to room temperature. Solids precipitated were filtered to obtain corresponding hydrochloride salts of 7a-e. To a suspension of these salts in dichloromethane was added 50% ammonium hydroxide solution (1.2 equiv.) and stirred for 3 h at room temperature. Organic layer was extracted, dried over sodium sulfate and concentrated to dryness to get the amines 7a-e. Corresponding references were provided in the general experimental section for reported compounds and data for 7c and 7d are shown below.

2-(5,7-Difluoro-2-methyl-1H-indol-3-yl)ethan-1-aminiumchloride (7c-HCl)

$^1$H NMR (400 MHz, DMSO-d$_6$): δ 11.48 (s, 1H), 8.15 (bs, 3H), 7.21-7.15 (m, 1H), 6.88-6.79 (m, 1H), 2.98-2.82 (m, 4H), 2.35 (s, 3H); LCMS (ESI): >95% purity. MS m/z, 211 [(M−HCl)+H]$^+$.

2-(5,7-Dichloro-2-methyl-1H-indol-3-yl)ethan-1-aminiumchloride (7d-HCl)

$^1$H NMR (400 MHz, DMSO-d$_6$): δ 11.46 (s, 1H), 8.13 (bs, 3H) 7.58 (s, 1H), 7.14 (s, 1H), 3.02-2.81 (m, 4H), 2.37 (s, 3H); LCMS (ESI): >95% purity. MS m/z, 243 [(M−HCl)+H]$^+$.

General Procedure for the Synthesis of 8a-g:

To a solution of 6a-g (0.5 mmol, 1 equiv.) and 2-(2-methyl-1H-indol-3-yl)ethan-1-amine (7) (0.5 mmol, 1 equiv.) in N,N-dimethylformamide and dichloromethane (1:1) was added DMAP (catalytic amount) followed by EDCI·HCl (0.65 mmol, 1.3 equiv.) and the reaction mixture was stirred at room temperature for 10 h. Then, dichloromethane was evaporated and the crude reaction mixture was added a saturated solution of ammonium chloride (15 mL) and extracted with ethyl acetate (15 mL). Organic layer was separated and washed with saturated solution of sodium bicarbonate (15 mL) followed by brine solution (15 mL). Combined organic layer was dried over sodium sulfate, concentrated to dryness. The crude was purified on silica gel chromatography using 50-70% ethyl acetate in hexanes to get the required products (8a-g).

N-(2-(2-Methyl-1H-indol-3-yl)ethyl)-6-phenylnicotinamide (8a) (TG9-77)

$^1$H NMR (400 MHz, CDCl$_3$): δ 8.85 (dt, J=2.4, 0.8 Hz, 1H), 8.07-8.03 (m, 1H), 8.01-7.96 (m, 2H), 7.90 (s, 1H), 7.76-7.71 (m, 1H), 7.55 (d, J=7.6 Hz, 1H), 7.51-7.41 (m, 3H), 7.31 (dd, J=4.5, 4.0 Hz, 1H), 7.18-7.07 (m, 2H), 6.22 (t, J=6.4 Hz, 1H), 3.76 (dd, J=6.4, 3.4 Hz, 2H), 3.07 (t, J=6.5 Hz, 2H), 2.40 (s, 3H); LCMS (ESI). LCMS (ESI): >97% purity; MS m/z, 356 [M+H]$^+$; HPLC purity: 99.4%.

6-(3-Methoxyphenyl)-N-(2-(2-methyl-1H-indol-3-yl)ethyl)nicotinamide (8b) (TG9-76)

$^1$H NMR (400 MHz, CDCl$_3$): δ 8.85 (dd, J=2.3, 0.7 Hz, 1H), 8.04 (dd, J=8.3, 2.3 Hz, 1H), 7.92 (s, 1H), 7.74 (dd, J=8.3, 0.8 Hz, 1H), 7.60-7.57 (m, 1H), 7.57-7.53 (m, 2H), 7.39 (t, J=7.9 Hz, 1H), 7.32-7.28 (m, 1H), 7.18-7.07 (m, 2H), 7.00 (dd, J=8.2, 2.6 Hz, 1H), 6.23 (t, J=6.0 Hz, 1H), 3.89 (s, 3H), 3.75 (dd, J=6.4, 3.6 Hz, 2H), 3.07 (t, J=6.5 Hz, 2H), 2.39 (s, 3H); LCMS (ESI): LCMS (ESI): >97% purity; MS m/z, 386 [M+H]$^+$; HPLC purity: 96.8%.

6-(2-Methoxyphenyl)-N-(2-(2-methyl-1H-indol-3-yl)ethyl)nicotinamide (8c) (TG9-100)

$^1$H NMR (400 MHz, DMSO-d$_6$): δ 10.74 (s, 1H), 9.06-9.02 (m, 1H), 8.82 (t, J=5.6 Hz, 1H), 8.19-8.15 (m, 1H), 7.96-7.92 (m, 1H), 7.81-7.76 (m, 1H), 7.52-7.40 (m, 2H), 7.25-7.15 (m, 2H), 7.11-7.05 (m, 1H), 7.01-6.89 (m, 2H), 3.85 (bs, 3H), 3.44 (dd, J=7.4, 3.6 Hz, 2H), 2.91 (t, J=7.7 Hz, 2H), 2.32 (s, 3H); LCMS (ESI): >99% purity; MS m/z, 386 [M+H]$^+$.

6-(2-Hydroxyphenyl)-N-(2-(2-methyl-1H-indol-3-yl)ethyl)nicotinamide (8d)

$^1$H NMR (400 MHz, DMSO-d$_6$): δ 13.75 (s, 1H), 10.74 (s, 1H), 9.01 (d, J=1.3 Hz, 1H), 8.89 (t, J=5.6 Hz, 1H), 8.39-8.28 (m, 2H), 8.07 (d, J=8.3 Hz, 1H), 7.48 (d, J=7.5 Hz, 1H), 7.35 (t, J=7.7 Hz, 1H), 7.23 (d, J=8.1 Hz, 1H), 7.00-6.89 (m, 4H), 3.49-3.41 (m, 2H), 2.92 (t, J=7.3 Hz, 2H), 2.32 (s, 3H); LCMS (ESI): LCMS (ESI): >97% purity; MS m/z, 372 [M+H]$^+$; HPLC purity: 97.1%.

6-(2-Fluorophenyl)-N-(2-(2-methyl-1H-indol-3-yl)ethyl)nicotinamide (Se) (TG9-83)

$^1$H NMR (400 MHz, CDCl$_3$): δ 8.89 (d, J=1.6 Hz, 1H), 8.05-7.96 (m, 2H), 7.88 (s, 1H), 7.84-7.80 (m, 1H), 7.54 (d, J=7.6 Hz, 1H), 7.44-7.37 (m, 1H), 7.31-7.25 (m, 2H), 7.19-7.07 (m, 3H), 6.21 (bs, 1H), 3.77 (q, J=6.4 Hz, 2H), 3.07 (t, J=6.5 Hz, 2H), 2.39 (s, 3H); LCMS (ESI): >99% purity; MS m/z, 374.0 [M+H]$^+$.

6-(4-Acetamidophenyl)-N-(2-(2-methyl-1H-indol-3-yl)ethyl)nicotinamide (8f) (T10-09)

$^1$H NMR (400 MHz, DMSO-d$_6$): δ 9.03 (d, J=1.6 Hz, 1H), 8.79 (t, J=5.7 Hz, 1H), 8.22 (dd, J=8.4, 2.3 Hz, 1H), 8.11 (d, J=8.8 Hz, 2H), 8.01 (d, J=8.4 Hz, 2H), 7.73 (d, J=8.7 Hz, 2H), 7.48 (d, J=7.7 Hz, 1H), 7.23 (d, J=7.6 Hz, 1H), 7.01-6.89 (m, 2H), 3.49-3.38 (m, 2H), 2.96-2.86 (m, 2H), 2.32 (s, 3H), 2.08 (s, 3H); LCMS (ESI): LCMS (ESI): >95% purity; m/z, 413 [M+H]$^+$; HPLC purity: 95.8%.

6-(3,5-Dimethoxyphenyl)-N-(2-(2-methyl-1H-indol-3-yl)ethyl)nicotinamide (8g) (T9-131)

$^1$H NMR (400 MHz, CDCl$_3$): δ 8.84 (s, 1H), 8.02 (dt, J=8.3, 2.1 Hz, 1H), 7.92 (s, 1H), 7.70 (d, J=8.3 Hz, 1H), 7.54 (d, J=7.5 Hz, 1H), 7.30 (d, J=7.9 Hz, 1H), 7.18-7.05 (m, 4H), 6.55 (q, J=2.0 Hz, 1H), 6.23 (t, J=4.8 Hz, 1H), 3.86 (d, J=1.8 Hz, 6H), 3.77 (q, J=6.3 Hz, 2H), 3.04 (t, J=6.5 Hz, 2H), 2.39 (d, J=1.5 Hz, 3H). LCMS (ESI): >99% purity; MS m/z, 416.2 [M+H]$^+$.

General Procedure for the Synthesis of 10a-c:

A solution of boronic acid (4a-c) (4.1 mmol, 1 equiv.) and bromo-acid 9 (4.1 mmol, 1 equiv.) in tetrahydrofuran or toluene and water (6:1) were loaded into a sealed tube. To this solution, 1M Na$_2$CO$_3$ (8.2 mmol, 2 equiv.) was added and purged with nitrogen for 10 min. Then, Pd(PPh$_3$)$_4$ (0.2 mmol, 0.05 equiv.) catalyst was added to the reaction mixture, sealed and heated to 100° C. for 12 h. Reaction mixture was cooled to room temperature and solvent was evaporated under vacuum. The residue was washed with dichloromethane to remove organic impurities. Then, aqueous layer was acidified to pH 2 with concentrated HCl to result in white precipitate, which was filtered and dried under vacuum to provide the intermediates 10a (WO2010005783A1), 10b (Id.) and 10c. Often these compounds used for next reaction without purification.

5-(4-Acetamidophenyl)picolinic acid (10c)

$^1$H NMR (400 MHz, DMSO-d$_6$): δ 10.18 (s, 1H), 9.01 (s, 1H), 8.24 (d, J=11 Hz, 1H), 8.08 (d, J=11 Hz, 1H), 7.84-7.70 (m, 4H), 2.08 (s, 3H). LCMS (ESI): >95% purity; MS m/z, 255 [M−H]$^+$.

General Procedure for the Synthesis of 11a-c:

To a solution of 10a-c (0.5 mmol, 1 equiv.) and 2-(2-methyl-1H-indol-3-yl)ethan-1-amine (7) (0.5 mmol, 1 equiv.) in N,N-dimethylformamide and dichloromethane (1:1) was added DMAP (catalytic amount) followed by EDCI·HCl (0.65 mmol, 1.3 equiv.) and the reaction mixture was stirred at room temperature for 10 h. Then, dichloromethane was evaporated and the crude reaction mixture was added a saturated solution of ammonium chloride (15 mL) and extracted with ethyl acetate (15 mL). Organic layer was separated and washed with saturated solution of sodium bicarbonate (15 mL) followed by brine solution (15 mL). Combined organic layer was dried over sodium sulfate, concentrated to dryness. The crude was purified on silica gel chromatography using 50-70% ethyl acetate in hexanes to get the required products (11a-c).

5-(3-Methoxyphenyl)-N-(2-(2-methyl-1H-indol-3-yl)ethyl)picolinamide (11a) (TG9-84-2)

$^1$H NMR (400 MHz, CDCl$_3$): δ 8.68 (d, J=2.2 Hz, 1H), 8.25 (d, J=8.1 Hz, 1H), 8.17 (t, J=5.6 Hz, 1H), 8.04 (s, 1H), 8.00-7.95 (m, 1H), 7.57 (d, J=7.4 Hz, 1H), 7.40 (t, J=8.0 Hz, 1H), 7.28 (d, J=7.7 Hz, 1H), 7.18-7.05 (m, 4H), 6.97 (dd, J=8.3, 2.5 Hz, 1H), 3.86 (s, 3H), 3.72-3.75 (m, 2H), 3.04 (t, J=6.9 Hz, 2H), 2.37 (s, 3H); LCMS (ESI): >98% purity; MS m/z, 386 [M+H]$^+$.

5-(3,5-Dimethoxyphenyl)-N-(2-(2-methyl-1H-indol-3-yl)ethyl)picolinamide (11b) (TG9-143)

$^1$H NMR (400 MHz, CDCl$_3$): δ 8.69 (d, J=6.8 Hz, 1H), 8.26 (d, J=8.1 Hz, 1H), 8.16 (t, J=5.9 Hz, 1H), 8.01-7.97 (m, 1H), 7.86 (s, 1H), 7.58 (d, J=7.5 Hz, 1H), 7.31-7.27 (m, 1H), 7.16-7.06 (m, 2H), 6.71 (d, J=2.2 Hz, 2H), 6.53 (t, J=2.2 Hz, 1H), 3.86 (s, 6H), 3.74 (q, J=6.8 Hz, 2H), 3.05 (t, J=7.0 Hz, 2H), 2.39 (s, 3H); LCMS (ESI):LCMS (ESI): >97% purity; MS m/z, 416 [M+H]$^+$; HPLC purity: 97.6%.

5-(4-Acetamidophenyl)-N-(2-(2-methyl-1H-indol-3-yl)ethyl)picolinamide (11c) (TG10-15)

$^1$H NMR (400 MHz, DMSO-d$_6$): δ 10.69 (s, 1H), 10.14 (s, 1H), 8.87 (d, J=2.1 Hz, 1H), 8.81 (t, J=5.9 Hz, 1H), 8.20 (dd, J=7.4, 3.1 Hz, 1H), 8.05 (d, J=8.1 Hz, 1H), 7.66-7.78 (m, 4H), 7.58-7.43 (m, 1H), 7.20 (d, J=7.7 Hz, 1H), 6.96-6.63 (m, 2H), 3.33-3.46 (m, 2H), 2.88 (t, J=7.2 Hz, 2H), 2.29 (s, 3H), 2.04 (s, 3H); LCMS (ESI): LCMS (ESI): >97% purity; MS m/z, 413 [M+H]$^+$.

General Procedure for the Synthesis 13a-c:

A solution of boronic acid, 4c (4.1 mmol, 1 equiv.) and with 12a-c (4.1 mmol, 1 equiv.) in dioxane and water (6:1) were loaded into a sealed tube. To this solution, 1M Na$_2$CO$_3$ (8.2 mmol, 2 equiv.) was added and purged with nitrogen for 10 min. Then, Pd(dppf)Cl$_2$ (0.2 mmol, 0.05 equiv.) catalyst was added to the reaction mixture, sealed and heated to 120° C. for 12 h. Reaction mixture was cooled to room temperature and solvent was evaporated under vacuum. The residue was washed with dichloromethane to remove organic impurities. Then, aqueous layer was acidified to pH 2 with concentrated HCl to result in white precipitate, which was filtered and dried under vacuum to provide the intermediates (13a, 13b, and 13c). (Fandrick, D. R., et al. General and Rapid Pyrimidine Condensation by Addressing the Rate Limiting Aromatization. *Org. Lett.* 2014, 16, 2834-2837; Juby, P. F., et al. Antiallergy Agents. 2. 2-Phenyl-5-(1H-tetrazol-5-yl)pyrimidin-4(3H)-ones. *J. Med. Chem.* 1982, 25, 1145-1150; Ricci, P., et al. Arene-metal Π-complexation as a Traceless Reactivity Enhancer for C-H Arylation. *J. Am. Chem. Soc.* 2013, 135, 13258-13261; Senaweera, S., et al., Dual C-F, C-H Functionalization via Photocatalysis: Access to Multifluorinated Biaryls. *J. Am. Chem. Soc.* 2016, 138, 2520-2523; Shen, Y., et al. Synthesis of Polyfluoroarene-Substituted Benzofuran Derivatives via Cooperative Pd/Cu Catalysis. *ChemComm* 2018, 54, 2256-2259; Hansen, A. H., et al., Discovery of a Potent Thiazolidine Free Fatty Acid Receptor 2 Agonist with Favorable Pharmacokinetic Properties. *J. Med. Chem.* 2018, 61, 9534-9550)

General Procedure for the Synthesis of 14a-c:

To a solution of 13a-c (0.5 mmol, 1 equiv.) and 2-(2-methyl-1H-indol-3-yl)ethan-1-amine (7) (0.5 mmol, 1 equiv.) in N,N-dimethylformamide and dichloromethane (1:1) was added DMAP (catalytic amount) followed by EDCI·HCl (0.65 mmol, 1.3 equiv.) and the reaction mixture was stirred at room temperature for 10 h. Then, dichloromethane was evaporated and the crude reaction mixture was added a saturated solution of ammonium chloride (15 mL) and extracted with ethyl acetate (15 mL). Organic layer was separated and washed with saturated solution of sodium bicarbonate (15 mL) followed by brine solution (15 mL). Combined organic layer was dried over sodium sulfate, concentrated to dryness. The crude was purified on silica gel chromatography using 50-70% ethyl acetate in hexanes to get the required products (14a-c).

2-(2-Methoxyphenyl)-N-(2-(2-methyl-1H-indol-3-yl)ethyl)pyrimidine-5-carboxamide (14a) (TG9-126)

$^1$H NMR (400 MHz, CDCl$_3$): δ 9.00 (s, 2H), 7.92 (s, 1H), 7.74 (dd, J=7.6, 1.6 Hz, 1H), 7.53 (d, J=7.4 Hz, 1H), 7.49-7.43 (m, 1H), 7.28 (d, J=8.0 Hz, 1H), 7.17-6.99 (m, 4H), 6.25 (s, 1H), 3.86 (s, 3H), 3.75 (q, J=6.4 Hz, 2H), 3.07 (t, J=6.5 Hz, 2H), 2.37 (s, 3H); LCMS (ESI): >97% purity; MS m/z, 387 [M+H]$^+$.

2-Fluoro-2'-methoxy-N-(2-(2-methyl-1H-indol-3-yl)ethyl)-[1,1'-biphenyl]-4-carboxamide (14b)

$^1$H NMR (400 MHz, CDCl$_3$): δ 7.85 (s, 1H), 7.54 (d, J=7.6 Hz, 1H), 7.44-7.26 (m, 4H), 7.22 (d, J=6.3 Hz, 2H), 7.17-7.06 (m, 2H), 7.05-6.95 (m, 2H), 6.16 (t, J=5.3 Hz, 1H), 3.76 (s, 3H), 3.74-3.67 (m, 2H), 3.04 (t, J=6.6 Hz, 2H), 2.38 (s, 3H); LCMS (ESI): >98% purity; MS m/z, 403 [M+H]$^+$.

2'-Methoxy-N-(2-(2-methyl-1H-indol-3-yl)ethyl)-[1,1'-biphenyl]-4-carboxamide (14c)

$^1$H NMR (400 MHz, DMSO-d$_6$): δ 10.70 (s, 1H), 8.60 (t, J=5.9 Hz, 1H), 7.87-7.79 (m, 2H), 7.56-7.49 (m, 2H), 7.46 (d, J=7.5 Hz, 1H), 7.37-7.28 (m, 2H), 7.22-7.17 (m, 1H), 7.11 (dd, J=5.5, 4.6 Hz, 1H), 7.05-6.98 (m, 1H), 6.98-6.86 (m, 2H), 3.75 (d, J=1.9 Hz, 3H), 3.43-3.34 (m, 2H), 2.86 (t, J=7.4 Hz, 2H), 2.29 (d, J=1.9 Hz, 3H); LCMS (ESI): >97% purity; MS m/z, 385 [M+H]$^+$; HPLC purity: 96%.

Scheme 3: Synthesis of middle and right side ring modified EP2 antagonist derivatives

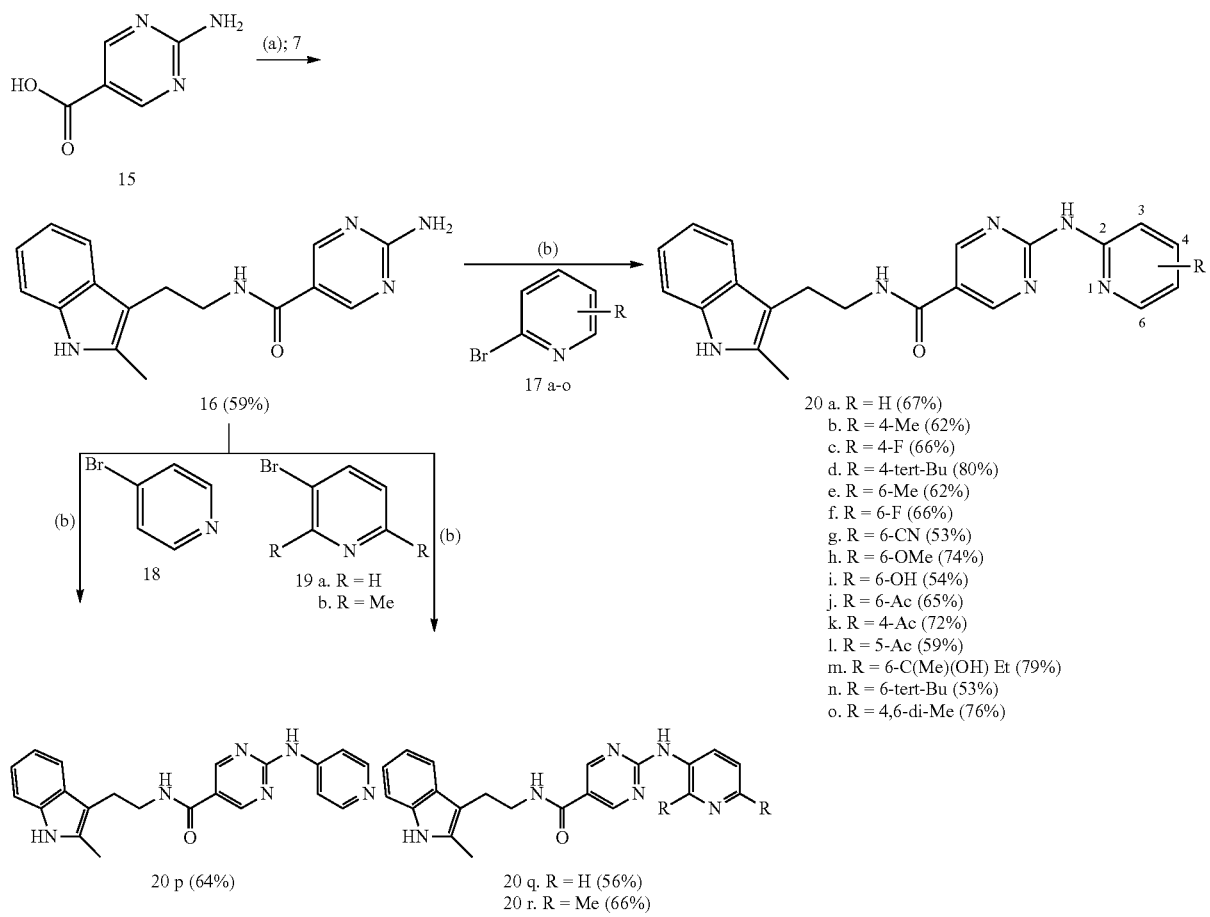

<sup>a</sup>Reagents and conditions: (a) DMAP, EDCI•HCl, DMF, rt, 24 h. (b) 17 or 18 or 19, Pd$_2$(dba)$_3$, Cs$_2$CO$_3$, xantphos, dioxane, 100° C., 12-18 h; Yield for each reaction product is shown in the parenthesis.

2-Amino-N-(2-(2-methyl-1H-indol-3-yl)ethyl)pyrimidine-5-carboxamide (16)

To a solution of commercially available acid 15 (3 g, 21 mmol, 1 equiv.) in N,N-dimethylformamide (20 mL) was added DMAP (0.78 g, 6.3 mmol, 0.3 equiv.) followed by EDCI·HCl (5.35 g, 28 mmol, 1.3 equiv.) and stirred at room temperature for 10 minutes. Then, 2-(2-methyl-1H-indol-3-yl)ethan-1-amine (7) was added to the reaction mixture and stirred at room temperature for 24 h. Reaction mixture was added saturated solution of ammonium chloride (5 mL) and extracted with ethyl acetate (3×10 mL). Organic layer was separated and washed with saturated solution of sodium bicarbonate (5 mL) followed by brine solution. Combined organic layer was dried over sodium sulfate, concentrated to dryness. The crude material was purified on silica gel chromatography using 4-6% methanol in dichloromethane to get the required product 16 as solid (Yield: 59%). $^1$H NMR (400 MHz, DMSO-d$_6$): δ 10.69 (s, 1H), 8.61 (s, 2H), 8.39 (t, J=5.6 Hz, 1H), 7.42 (d, J=7.7 Hz, 1H), 7.22-7.17 (m, 1H), 7.16 (s, 2H), 6.97-6.85 (m, 2H), 3.41-3.27 (m, 2H), 2.82 (t, J=7.4 Hz, 2H), 2.27 (s, 3H); LCMS (ESI): >98% purity. MS m/z, 296 [M+H]$^+$.

General Procedure for the Synthesis of 20a-20r:

To a solution of 16 (0.5 mmol, 1 equiv.) and 2-bromopyridines (17a-o or 18 or 19a-b) (0.5 mmol, 1 equiv.) in dioxane was added Cs$_2$CO$_3$ (1.0 mmol, 2 equiv.). The solution was purged with nitrogen for 10 minutes. Then, Xantphos (0.05 mmol, 0.1 equiv.) was added followed by Pd$_2$(dba)$_3$ catalyst (0.05 mmol, 0.1 equiv.) and heated to 100° C. for 12-18 h. Reaction mixture was cooled to room temperature and added water (10 mL). Resultant solid was filtered and purified on silica gel chromatography using 3-5% methanol in dichloromethane to get the required products 20a-r.

N-(2-(2-Methyl-1H-indol-3-yl)ethyl)-2-(pyridin-2-ylamino)pyrimidine-5-carboxamide (20a) (TG11-265)

$^1$H NMR (400 MHz, DMSO-d$_6$): δ 10.71 (s, 1H), 10.29 (s, 1H), 8.88 (s, 2H), 8.66 (t, J=5.4 Hz, 1H), 8.29 (d, J=4.9 Hz, 1H), 8.21 (d, J=8.4 Hz, 1H), 7.79-7.72 (m, 1H), 7.44 (d, J=7.6 Hz, 1H), 7.20 (d, J=7.8 Hz, 1H), 7.06-6.99 (m, 1H), 6.97-6.86 (m, 2H), 3.35-3.42 (m, 2H), 2.86 (t, J=7.3 Hz, 2H), 2.28 (s, 3H); LCMS (ESI): >97% purity; MS m/z, 373 [M+H]$^+$; HPLC purity: 98.1%.

N-(2-(2-Methyl-1H-indol-3-yl)ethyl)-2-((4-methylpyridin-2-yl)amino)pyramidine-5-carboxamide (20b)

$^1$H NMR (400 MHz, DMSO-d$_6$): δ 10.74 (s, 1H), 10.22 (s, 1H), 8.92-8.89 (m, 2H), 8.67 (t, J=5.7 Hz, 1H), 8.18 (d,

J=5.0 Hz, 1H), 8.08 (s, 1H), 7.47 (d, J=7.6 Hz, 1H), 7.26-7.19 (m, 1H), 7.01-6.87 (m, 3H), 3.45-3.38 (m, 2H), 2.89 (t, J=7.3 Hz, 2H), 2.34 (s, 3H), 2.32 (s, 3H); LCMS (ESI): >95% purity; MS m/z, 387 [M+H]$^+$.

2-((4-Fluoropyridin-2-yl)amino)-N-(2-(2-methyl-1H-indol-3-yl)ethyl)pyrimidine-5-carboxamide (20c)

$^1$H NMR (400 MHz, DMSO-d$_6$): δ 10.74 (s, 1H), 10.70 (s, 1H), 8.95 (s, 2H), 8.72 (t, J=8 Hz 1H), 8.37-8.31 (m, 1H), 8.20-8.13 (m, 1H), 7.46 (d, J=7.7 Hz, 1H), 7.23 (d, J=8.0 Hz, 1H), 7.03-6.89 (m, 3H), 3.45-3.38 (m, 2H), 2.89 (t, J=6.7 Hz, 2H), 2.31 (d, J=2.0 Hz, 3H); LCMS (ESI): >97% purity; MS m/z, 391 [M+H]$^+$; HPLC purity: 98.1%.

2-((4-(tert-Butyl)pyridin-2-yl)amino)-N-(2-(2-methyl-1H-indol-3-yl)ethyl)pyrimidine-5-carboxamide (20d)

$^1$H NMR (400 MHz, DMSO-d$_6$): δ 10.71 (s, 1H), 10.23 (s, 1H), 8.89 (d, J=2.8 Hz, 2H), 8.62 (t, J=5.6 Hz, 1H), 8.27-8.30 (m, 1H), 8.21-8.17 (m, 1H), 7.43 (d, J=7.6 Hz, 1H), 7.20 (dd, J=7.8, 0.8 Hz, 1H), 7.05 (dd, J=5.3, 1.8 Hz, 1H), 6.97-6.85 (m, 2H), 3.42-3.33 (m, 2H), 2.86 (t, J=7.3 Hz, 2H), 2.28 (s, 3H), 1.29-1.24 (m, 9H); LCMS (ESI): >97% purity; MS m/z, 429 [M+H]$^+$.

N-(2-(2-Methyl-1H-indol-3-yl)ethyl)-2-((6-methylpyridin-2-yl)amino)pyrimidine-5-carboxamide (20e)

$^1$H NMR (400 MHz, DMSO-d$_6$): δ 10.74 (s, 1H), 10.17 (s, 1H), 8.90 (d, J=2.1 Hz, 2H), 8.67 (t, J=5.3 Hz, 1H), 8.07 (d, J=8.3 Hz, 1H), 7.68 (t, J=7.8 Hz, 1H), 7.47 (d, J=7.8 Hz, 1H), 7.23 (d, J=7.7 Hz, 1H), 7.00-6.88 (m, 3H), 3.45-3.38 (m, 2H), 2.89 (t, J=7.4 Hz, 2H), 2.41 (s, 3H), 2.31 (s, 3H); LCMS (ESI): >98% purity; MS m/z, 387 [M+H]$^+$.

2-((6-Fluoropyridin-2-yl)amino)-N-(2-(2-methyl-1H-indol-3-yl)ethyl)pyrimidine-5-carboxamide (20f)

$^1$H NMR (400 MHz, DMSO-d$_6$): δ 10.74 (s, 1H), 10.61 (s, 1H), 8.95-8.91 (m, 2H), 8.73 (t, J=5.7 Hz, 1H), 8.22-8.17 (m, 1H), 7.97 (q, J=8.4 Hz, 1H), 7.47 (d, J=7.6 Hz, 1H), 7.25-7.20 (m, 1H), 7.01-6.89 (m, 2H), 6.77 (dd, J=7.8, 2.4 Hz, 1H), 3.45-3.37 (m, 2H), 2.89 (t, J=7.4 Hz, 2H), 2.31 (s, 3H); LCMS (ESI): >97% purity. MS m/z, 391 [M+H]$^+$.

2-((6-Cyanopyridin-2-yl)amino)-N-(2-(2-methyl-1H-indol-3-yl)ethyl)pyrimidine-5-carboxamide (20g)

$^1$H NMR (400 MHz, DMSO-d$_6$): δ 10.89 (s, 1H), 10.74 (s, 1H), 8.95 (s, 2H), 8.74 (t, J=4.8 Hz, 1H), 8.60-8.54 (m, 1H), 8.02 (t, J=8.1 Hz, 1H), 7.71-7.61 (m, 1H), 7.46 (d, J=7.6 Hz, 1H), 7.23 (d, J=7.7 Hz, 1H), 7.00-6.89 (m, 2H), 3.42 (dd, J=12.5, 6.2 Hz, 2H), 2.89 (t, J=6.9 Hz, 2H), 2.31 (s, 3H); LCMS (ESI): >97% purity; MS m/z, 398 [M+H]$^+$; HPLC purity: 97%.

2-((6-Methoxypyridin-2-yl)amino)-N-(2-(2-methyl-1H-indol-3-yl)ethyl)pyrimidine-5-carboxamide (20h)

$^1$H NMR (400 MHz, DMSO-d$_6$) δ 10.74 (s, 1H), 10.07 (s, 1H), 8.91 (s, 2H), 8.68 (t, J=5.7 Hz, 1H), 7.82 (d, J=7.9 Hz, 1H), 7.70 (t, J=7.9 Hz, 1H), 7.47 (d, J=7.5 Hz, 1H), 7.23 (d, J=7.6 Hz, 1H), 7.01-6.87 (m, 2H), 6.46 (d, J=7.8 Hz, 1H), 3.85 (s, 3H), 3.45-3.37 (m, 2H), 2.89 (t, J=7.1 Hz, 2H), 2.32 (s, 3H); LCMS (ESI): >96% purity; MS m/z, 403 [M+H]$^+$.

2-((6-Hydroxypyridin-2-yl)amino)-N-(2-(2-methyl-1H-indol-3-yl)ethyl)pyrimidine-5-carboxamide (20i)

$^1$H NMR (400 MHz, DMSO-d$_6$): δ 12.01 (s, 1H), 10.74 (s, 2H), 8.95 (s, 2H), 8.74 (t, J=5.5 Hz, 1H), 7.50-7.40 (m, 2H), 7.23 (d, J=8.2 Hz, 1H), 7.01-6.87 (m, 2H), 6.41 (bs, 1H), 5.98 (d, J=8.8 Hz, 1H), 3.46-3.38 (m, 2H), 2.89 (t, J=7.4 Hz, 2H), 2.31 (s, 3H); LCMS (ESI): >97% purity; MS m/z, 389 [M+H]$^+$.

2-((6-Acetylpyridin-2-yl)amino)-N-(2-(2-methyl-1H-indol-3-yl)ethyl)pyrimidine-5-carboxamide (20j)

$^1$H NMR (400 MHz, DMSO-d$_6$): δ 10.71 (s, 1H), 10.49 (s, 1H), 8.91 (s, 2H), 8.73-8.63 (m, 1H), 8.41 (d, J=9.2 Hz, 1H), 7.96 (t, J=7.2 Hz, 1H), 7.58 (d, J=7.5 Hz, 1H), 7.44 (d, J=7.2 Hz, 1H), 7.20 (d, J=8.5 Hz, 1H), 6.98-6.82 (m, 2H), 3.39 (dd, J=13.5, 6.7 Hz, 2H), 2.86 (t, J=7.4 Hz, 2H), 2.60 (s, 3H), 2.29 (s, 3H); LCMS (ESI): >97% purity; MS m/z, 415 [M+H]$^+$.

2-((4-Acetylpyridin-2-yl)amino)-N-(2-(2-methyl-1H-indol-3-yl)ethyl)pyrimidine-5-carboxamide (20k)

$^1$H NMR (400 MHz, DMSO-d$_6$): δ 10.71 (s, 1H), 10.61 (s, 1H), 8.92 (s, 2H), 8.71-8.60 (m, 2H), 8.49 (d, J=5.1 Hz, 1H), 7.54-7.37 (m, 2H), 7.20 (d, J=7.7 Hz, 1H), 6.92 (dd, J, 14.1, 7.1 Hz, 2H), 3.39 (dd, J=13.9, 6.5 Hz, 2H), 2.86 (t, J=7.5 Hz, 2H), 2.60 (s, 3H), 2.29 (s, 3H); LCMS (ESI): >97% purity; MS m/z, 415 [M+H]$^+$; HPLC purity: 96.2%.

2-((5-Acetylpyridin-2-yl)amino)-N-(2-(2-methyl-1H-indol-3-yl)ethyl)pyrimidine-5-carboxamide (20l)

$^1$H NMR (400 MHz, DMSO-d$_6$): δ 10.87 (s, 1H), 10.72 (s, 1H), 8.94 (s, 2H), 8.88 (d, J=2.4 Hz, 1H), 8.72 (t, J=5.7 Hz, 1H), 8.38 (d, J=8.9 Hz, 1H), 8.27 (dd, J=8.9, 2.3 Hz, 1H), 7.44 (d, J=7.5 Hz, 1H), 7.20 (d, J=7.5 Hz, 1H), 6.92 (dt, J=14.6, 7.0 Hz, 2H), 3.39 (dd, J=13.4, 6.6 Hz, 2H), 2.87 (t, J=7.3 Hz, 2H), 2.54 (s, 3H), 2.29 (s, 3H); LCMS (ESI): >98% purity; MS m/z, 415 [M+H]$^+$.

2-((6-(2-Hydroxybutan-2-yl)pyridin-2-yl)amino)-N-(2-(2-methyl-1H-indol-3-yl)ethyl) pyrimidine-5-carboxamide (20m)

$^1$H NMR (400 MHz, DMSO-d$_6$): δ 10.71 (s, 1H), 10.06 (s, 1H), 8.88 (s, 2H), 8.65 (t, J=5.7 Hz, 1H), 8.03 (d, J=8.2 Hz, 1H), 7.74 (t, J=7.9 Hz, 1H), 7.43 (d, J=7.6 Hz, 1H), 7.20 (dd, J=7.7, 3.2 Hz, 2H), 6.91 (ddd, J=14.7, 13.6, 6.2 Hz, 2H), 5.07 (s, 1H), 3.38 (dd, J=13.5, 7.0 Hz, 2H), 2.86 (t, J=7.3 Hz, 2H), 2.28 (s, 3H), 1.87-1.58 (m, 2H), 1.37 (s, 3H), 0.64 (t, J=7.4 Hz, 3H); LCMS (ESI): >98% purity; MS m/z, 445 [M+H]$^+$.

2-((6-(tert-Butyl)pyridin-2-yl)amino)-N-(2-(2-methyl-1H-indol-3-yl)ethyl)pyrimidine-5-carboxamide (20n)

$^1$H NMR (400 MHz, DMSO-d$_6$): δ 10.71 (s, 1H), 9.87 (s, 1H), 8.88 (d, J=6.0 Hz, 2H), 8.64 (t, J=5.6 Hz, 1H), 7.98 (d, J=8.1 Hz, 1H), 7.68 (t, J=7.9 Hz, 1H), 7.44 (d, J=7.3 Hz,

1H), 7.20 (d, J=7.3 Hz, 1H), 7.04 (d, J=7.6 Hz, 1H), 7.02-6.80 (m, 2H), 3.43-3.34 (m, 2H), 2.86 (t, J=7.2 Hz, 2H), 2.29 (s, 3H), 1.30-1.25 (m, 9H); LCMS (ESI): >97% purity; MS m/z, 429 [M+H]$^+$.

2-((4,6-Dimethylpyridin-2-yl)amino)-N-(2-(2-methyl-1H-indol-3-yl)ethyl)pyrimidine-5-carboxamide (20o; TG11-77)

$^1$H NMR (400 MHz, DMSO-d$_6$): δ 10.74 (s, 1H), 10.08 (s, 1H), 8.90 (s, 2H), 8.65 (t, J=5.5 Hz, 1H), 7.92 (s, 1H), 7.47 (d, J=7.6 Hz, 1H), 7.23 (d, J=7.8 Hz, 1H), 6.95 (dt, J=20.4, 7.3 Hz, 2H), 6.76 (s, 1H), 3.45-3.37 (m, 2H), 2.89 (t, J=7.3 Hz, 2H), 2.37 (s, 3H), 2.32 (s, 3H), 2.30 (s, 3H); LCMS (ESI): >95% purity. MS m/z, 401 [M+H]$^+$; HPLC purity: 96.4%.

2-((4,6-Dimethylpyridin-2-yl)amino)-N-(2-(2-methyl-1H-indol-3-yl)ethyl)pyrimidine-5-carboxamide. Hydrochloride (20o-HCl; TG11-77-HCl)

To a solution of 20o (500 mg, 1.25 mmol, 1 equiv.) in dichloromethane (5 mL) was added 4M HCl in dioxane (0.62 mL, 2.5 mmol, 2 equiv.) at 0° C. and allowed to stir at room temperature for 12 h. The precipitated solid was filtered and washed with dichloromethane (5 mL) followed by ethyl acetate (5 mL) and dried to get the required salt, 20o.HCl (Yield: 86%). $^1$H NMR (400 MHz, DMSO-d$_6$): δ 11.95 (s, 1H), 10.79 (s, 1H), 9.13 (s, 2H), 8.99 (t, J=5.3 Hz, 1H), 7.61 (s, 1H), 7.46 (d, J=7.7 Hz, 1H), 7.23 (d, J=7.7 Hz, 1H), 7.18 (s, 1H), 7.00-6.88 (m, 2H), 3.66 (bs, 1H), 3.44 (q, J=6.7 Hz, 2H), 2.91 (t, J=7.3 Hz, 2H), 2.62 (s, 3H), 2.47 (s, 3H), 2.32 (s, 3H); LCMS (ESI): >97% purity. MS m/z, 401 [(M−HCl)+H]$^+$; HPLC purity: 99%.

N-(2-(2-Methyl-1H-indol-3-yl)ethyl)-2-(pyridin-4-ylamino)pyrimidine-5-carboxamide (20p)

$^1$H NMR (400 MHz, DMSO-d$_6$): δ 10.78 (d, J=2.3 Hz, 1H), 9.34-9.29 (m, 4H), 9.22-9.14 (m, 2H), 7.45 (d, J=7.7 Hz, 1H), 7.20 (d, J=7.9 Hz, 1H), 7.08-7.01 (m, 2H), 6.97-6.82 (m, 2H), 3.46-3.40 (m, 2H), 2.90 (t, J=7.3 Hz, 2H), 2.29 (d, J=2.0 Hz, 3H); LCMS (ESI): >97% purity. MS m/z, 373 [M+H]$^+$.

N-(2-(2-Methyl-1H-indol-3-yl)ethyl)-2-(pyridin-3-ylamino)pyrimidine-5-carboxamide (20q)

$^1$H NMR (400 MHz, DMSO-d$_6$): δ 10.70 (s, 1H), 10.26 (s, 1H), 8.91 (s, 1H), 8.88 (s, 2H), 8.62 (t, J=5.5 Hz, 1H), 8.26-8.18 (m, 2H), 7.46 (d, J=7.6 Hz, 1H), 7.35 (dd, J=8.2, 4.8 Hz, 1H), 7.22 (d, J=7.8 Hz, 1H), 7.00-6.87 (m, 2H), 3.48-3.35 (m, 2H), 2.89 (t, J=7.3 Hz, 2H), 2.32 (s, 3H); LCMS (ESI): >97% purity. MS m/z, 373 [M+H]$^+$; HPLC purity: 97.6%.

2-((2,6-Dimethylpyridin-3-yl)amino)-N-(2-(2-methyl-1H-indol-3-yl)ethyl)pyrimidine-5-carboxamide (20r)

$^1$H NMR (400 MHz, DMSO-d$_6$): δ 10.73 (s, 1H), 9.44 (s, 1H), 8.75 (s, 2H), 8.55 (t, J=5.7 Hz, 1H), 7.64 (d, J=8.1 Hz, 1H), 7.46 (d, J=7.7 Hz, 1H), 7.21 (d, J=7.6 Hz, 1H), 7.09 (d, J=8.1 Hz, 1H), 7.00-6.88 (m, 2H), 3.43-3.35 (m, 2H), 2.87 (t, J=7.3 Hz, 2H), 2.42 (s, 3H), 2.35 (s, 3H), 2.31 (s, 3H); LCMS (ESI): >97% purity; MS m/z, 401[M+H]$^+$; HPLC purity: 97.3%.

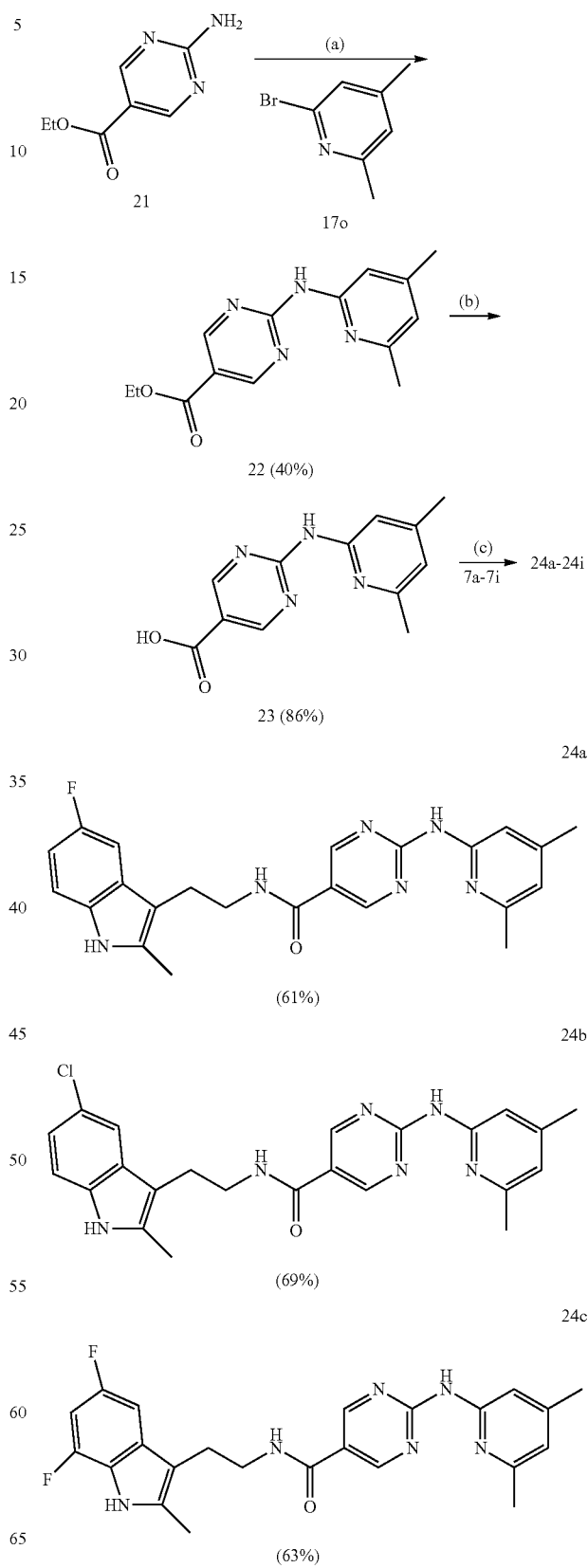

Scheme 4. Synthesis of left side indole and ethylene linker modified analogs

-continued

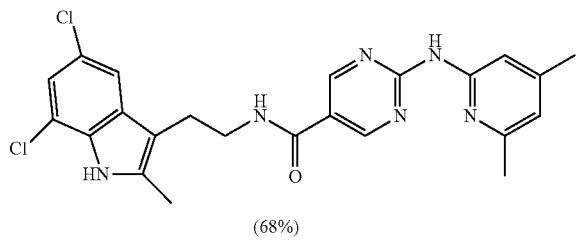
24d
(68%)

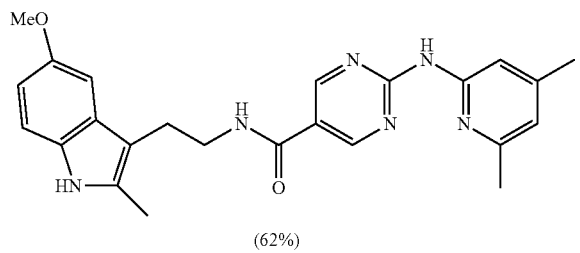
24e
(62%)

24f
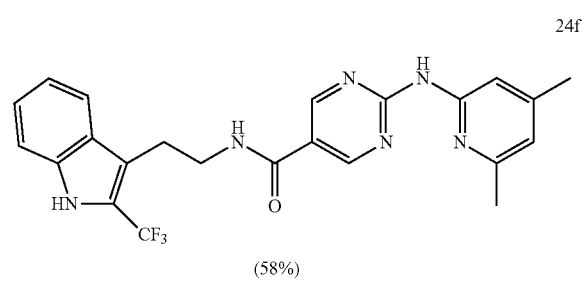
(58%)

24g
(42%)

24h
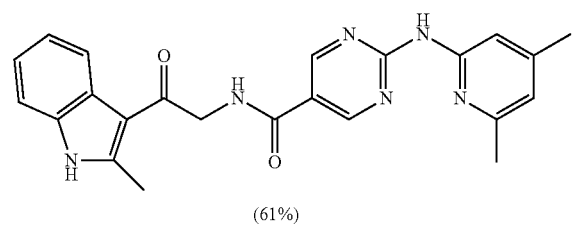
(61%)

-continued

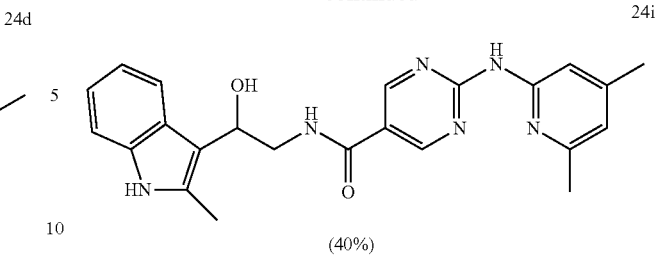
24i
(40%)

<sup>a</sup>Reagents and conditions: (a) Pd(OAc)₂, BINAP, Cs₂CO₃, dioxane, 100° C., 48 h, 40%; (b) LiOH, THF:H₂O, (7:3), 12 h, 60° C.; (c) 7a-7i, EDCI·HCl, DMAP, DMF, 50° C., 24-48 h; Yield for each reaction product is shown in the parenthesis. Yields are isolated but not optimized.

Ethyl 2-((4,6-dimethylpyridin-2-yl)amino)pyrimidine-5-carboxylate (22)

To a solution of 21 (250 mg, 1.6 mmol, 1 equiv.) and 17o (35 mg, 1.6 mmol, 1 equiv.) in dioxane (5 mL) were added Cs₂CO₃ (1.1 g, 3.26 mmol, 2 equiv.) followed by BINAP (100 g, 0.16 mmol, 0.1 equiv.). Reaction mixture was purged with nitrogen for 10 minutes and added Pd(OAc)₂ (36 mg, 0.16 mmol, 0.1 equiv.) and heated to 100° C. for 48 h. Reaction mixture was cooled to room temperature and added water and filtered the solid, which was purified on column chromatography using 30-40% ethyl acetate in hexanes to get the required compound 22. $^1$H NMR (400 MHz, CDCl₃): δ 11.75 (s, 1H), 9.12 (s, 2H), 8.62 (s, 1H), 6.84 (s, 1H), 4.50-4.28 (m, 2H), 2.70 (s, 3H), 2.54 (s, 3H), 1.40 (t, J=7.1 Hz, 3H); LCMS (ESI): >94% purity. MS m/z, 273 [M+H]⁺.

2-((4,6-Dimethylpyridin-2-yl)amino)pyrimidine-5-carboxylic acid (23)

To a solution of 22 (100 mg, 0.38 mmol, 1 equiv.) in tetrahydrofuran and water (7:3, 5 mL) was added LiOH·H₂O (46 mg, 1.14 mmol, 3 equiv.) and heated to 60° C. for 12 h. Reaction mixture was brought to room temperature and acidified with 1N HCl and extracted with ethyl acetate (20 mL). Organic layer was concentrated to dryness to obtain the required acid 23. $^1$H NMR (400 MHz, DMSO-d₆): δ 9.54 (s, 1H), 8.77 (s, 2H), 7.92 (s, 1H), 6.67 (s, 1H), 2.31 (s, 3H), 2.25 (s, 3H); LCMS (ESI): >96% purity; MS m/z, 243 [M–H]⁺.

General Procedure for the Synthesis of Compounds 24a-i:

To a solution of 23 (0.61 mmol, 1 equiv.) and compound 7a-i (0.61 mmol, 1 equiv.) in N,N-dimethylformamide (5 mL) was added DMAP (catalytic amount) followed by EDCI·HCl (0.78 mmol, 1.3 equiv.) and the reaction mixture was stirred at 50° C. for 24-48 h. Reaction mixture was brought to room temperature and added saturated solution of ammonium chloride (10 mL) and extracted with ethyl acetate (10 mL). Organic layer was separated and washed with saturated solution of sodium bicarbonate (10 mL) followed by brine solution (10 mL). Combined organic layer was dried over sodium sulfate, concentrated to dryness. The crude was purified on silica gel chromatography using 5-7% methanol in dichloromethane to get the required products (24a-i).

2-((4,6-Dimethylpyridin-2-yl)amino)-N-(2-(5-fluoro-2-methyl-1H-indol-3-yl)ethyl)pyrimidine-5-carboxamide (24a)

$^1$H NMR (400 MHz, DMSO-d₆): δ 10.85 (s, 1H), 10.06 (s, 1H), 8.88 (s, 2H), 8.63 (t, J=5.8 Hz, 1H), 7.91 (s, 1H),

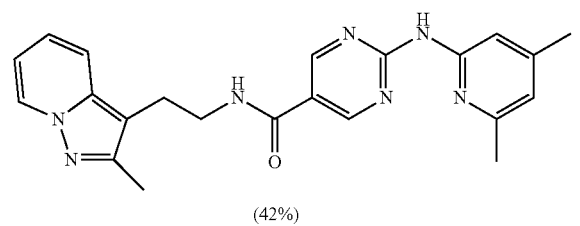

7.22-7.17 (m, 2H), 6.83-6.74 (m, 2H), 3.43-3.35 (m, 2H), 2.85 (t, J=7.3 Hz, 2H), 2.36 (s, 3H), 2.31 (s, 3H), 2.29 (s, 3H); LCMS (ESI): >96% purity; MS m/z, 419 [M+H]+.

N-(2-(5-Chloro-2-methyl-1H-indol-3-yl)ethyl)-2-((4,6-dimethylpyridin-2-yl)amino)pyrimidine-5-carboxamide (24b)

$^1$H NMR (400 MHz, DMSO-d$_6$): δ 10.97 (s, 1H), 10.09 (s, 1H), 8.89 (s, 2H), 8.63 (t, J=4.8 Hz, 1H), 7.92 (s, 1H), 7.48 (s, 1H), 7.23 (d, J=8.5 Hz, 1H) 7.08-6.88 (m, 1H), 6.76 (s, 1H), 3.44-3.37 (m, 2H), 2.91-2.82 (m, 2H), 2.36 (s, 3H), 2.31 (s, 3H), 2.29 (s, 3H); LCMS (ESI): >95% purity; MS m/z, 435 [M+H]+.

N-(2-(5,7-Difluoro-2-methyl-1H-indol-3-yl)ethyl)-2-((4,6-dimethylpyridin-2-yl)amino)pyrimidine-5-carboxamide (24c)

$^1$H NMR (400 MHz, DMSO-d$_6$): δ 11.32 (s, 1H), 10.09 (s, 1H), 8.88 (s, 2H), 8.62 (t, J=5.4 Hz, 1H), 7.91 (s, 1H), 7.11 (dd, J=9.6, 1.8 Hz, 1H), 6.82 (t, J=10.5 Hz, 1H), 6.76 (s, 1H), 3.44-3.36 (m, 2H), 2.86 (t, J=7.0 Hz, 2H), 2.37 (s, 3H), 2.32 (s, 3H), 2.29 (s, 3H); LCMS (ESI): >97% purity; MS m/z, 437 [M+H]+.

N-(2-(5,7-Dichloro-2-methyl-1H-indol-3-yl)ethyl)-2-((4,6-dimethylpyridin-2-yl)amino)pyrimidine-5-carboxamide (24d)

$^1$H NMR (400 MHz, DMSO-d$_6$): δ 11.29 (s, 1H), 10.04 (s, 1H), 8.82 (s, 2H), 8.56 (t, J=6.1 Hz, 1H), 7.92 (s, 1H), 7.45 (s, 1H), 7.09 (s, 1H), 6.73 (s, 1H), 3.36 (dd, J=12.0, 5.3 Hz, 2H), 2.85-2.81 (m, 2H), 2.69 (s, 3H), 2.33 (s, 3H), 2.26 (s, 3H); LCMS (ESI): >95% purity; MS m/z, 469 [M+H]+; HPLC purity: 95.5%.

2-((4,6-Dimethylpyridin-2-yl)amino)-N-(2-(5-methoxy-2-methyl-1H-indol-3-yl)ethyl)pyrimidine-5-carboxamide (24e)

$^1$H NMR (400 MHz, DMSO-d$_6$): δ 10.57 (s, 1H), 10.07 (s, 1H), 8.89 (s, 2H), 8.64 (t, J=5.6 Hz, 1H), 7.91 (s, 1H), 7.11 (d, J=8.6 Hz, 1H), 6.96 (d, J=2.2 Hz, 1H), 6.76 (s, 1H), 6.61 (dd, J=8.6, 2.3 Hz, 1H), 3.71 (s, 3H), 3.46-3.35 (m, 2H), 2.85 (t, J=7.2 Hz, 2H), 2.36 (s, 3H), 2.29 (bs, 6H); LCMS (ESI): >96% purity; MS m/z, 431 [M+H]+.

2-((4,6-Dimethylpyridin-2-yl)amino)-N-(2-(2-(trifluoromethyl)-1H-indol-3-yl)ethyl)pyrimidine-5-carboxamide (24f)

$^1$H NMR (400 MHz, DMSO-d$_6$): δ 11.97 (s, 1H), 10.07 (s, 1H), 8.86 (bs, 2H), 8.71 (t, J=5.7 Hz, 1H), 7.90 (s, 1H), 7.76 (d, J=8.0 Hz, 1H), 7.44 (d, J=8.3 Hz, 1H), 7.32-7.25 (m, 1H), 7.16-7.08 (m, 1H), 6.76 (s, 1H), 3.53-3.44 (m, 2H), 3.11 (t, J=6.8 Hz, 2H), 2.36 (s, 3H), 2.29 (s, 3H); LCMS (ESI): >97% purity; MS m/z, 455 [M+H]+.

2-((4,6-Dimethylpyridin-2-yl)amino)-N-(2-(2-methylpyrazolo[1,5-a]pyridin-3-yl)ethyl)pyrimidine-5-carboxamide (24g)

$^1$H NMR (400 MHz, DMSO-d$_6$): δ 10.03 (s, 1H), 8.81 (s, 2H), 8.59 (t, J=5.6 Hz, 1H), 8.45 (dd, J=7.0, 0.8 Hz, 1H), 7.86 (s, 1H), 7.47 (d, J=8.8 Hz, 1H), 7.13-6.97 (m, 1H), 6.77-6.64 (m, 2H), 3.42-3.37 (m, 2H), 2.87 (t, J=6.1 Hz, 2H), 2.33 (s, 3H), 2.30 (s, 3H), 2.25 (s, 3H); LCMS (ESI): >96% purity; MS m/z, 402 [M+H]+.

2-((4,6-Dimethylpyridin-2-yl)amino)-N-(2-(2-methyl-1H-indol-3-yl)-2-oxoethyl)pyrimidine-5-carboxamide (24h)

$^1$H NMR (400 MHz, DMSO-d$_6$): δ 11.97 (s, 1H), 10.10 (s, 1H), 8.97 (s, 2H), 8.82 (t, J=6.6 Hz, 1H), 8.05-7.95 (m, 1H), 7.91 (s, 1H), 7.46-7.33 (m, 1H), 7.21-7.10 (m, 2H), 6.74 (s, 1H), 4.72-4.53 (m, 2H), 2.71 (s, 3H), 2.34 (s, 3H), 2.27 (s, 3H); LCMS (ESI): >98% purity; MS m/z, 415 [M+H]+.

2-((4,6-Dimethylpyridin-2-yl)amino)-N-(2-hydroxy-2-(2-methyl-1H-indol-3-yl)ethyl)pyrimidine-5-carboxamide (24i)

$^1$H NMR (400 MHz, DMSO-d$_6$): δ 10.77 (s, 1H), 10.06 (s, 1H), 8.63 (t, J=8 Hz, 1H), 8.90 (s, 2H), 7.91 (s, 1H), 7.65 (d, J=8 Hz, 1H), 7.26-7.20 (m, 1H), 7.00-6.88 (m, 2H), 6.76 (s, 1H), 5.21 (d, J=3.3 Hz, 1H), 5.09-5.03 (t, J=8.2 Hz, 1H), 3.66-3.44 (m, 2H), 2.36 (s, 3H), 2.35 (s, 3H), 2.29 (s, 3H); LCMS (ESI): >96% purity; MS m/z, 417 [M+H]+.

SAR Analysis of Derivatives

TABLE 1

CNS desirable properties suggested by MPO approach and calculated biophysical properties of selected EP2 antagonists including earlier leads 2a, 3 and current lead 20o•HCl[a]

| Property | Property range for CNS drugs and candidates | 2a | 3 | 8c | 8g | 14a | 20o•HCl |
|---|---|---|---|---|---|---|---|
| MW/FW | 305-360 | 363 | 346 | 385 | 415 | 386 | 436 |
| cLogP | 2.3-3.3 | 3.25 | 2.64 | 4.02 | 3.86 | 3.49 | 3.58 |
| cLogD (pH 7.4) | 1.7-2.2 | 3.25 | 1.04 | 4.02 | 3.86 | 3.49 | 3.57 |
| pKa | 8.4 | 0.06 | −0.65 | 2.28 | 2.83 | 0.59 | 4.5 |
| HBD | 1 | 2 | 3 | 2 | 2 | 2 | 3 |
| PSA (Å$^2$) | 44.8-51.2 | 57.36 | 96.4 | 67.0 | 76.2 | 79.9 | 95 |
| MPO score | desired MPO score ≥4 | 4.7 | 5.0 | 3.8 | 3.7 | 4.3 | 3.6 |

[a]ChemAxon software was used to calculate the values for compounds 2a, 3 and 20o listed in Table 1

Compound 2a ((E)-N-(2-(2-(trifluoromethyl)-1H-indol-1-yl)ethyl)-3-(3,4,5-trimethoxyphenyl)acrylamide) has good EP2 potency and selectivity, and moderate aqueous solubility (Ganesh, T., et al., Development of Second Generation EP2 Antagonists with High Selectivity. *Eur. J. Med. Chem.* 2014, 82, 521-535). It has a morpholine ring on the right, phenyl ring in the middle, and 3-indole moiety on the left side. Compound 2b with a nicotinic acid ring was then synthesized and tested. Compound 2b displayed 4-fold less EP2 potency than 2a, but it showed 3-fold increased aqueous solubility reinforcing the notion that nitrogen in the ring will enhance the aqueous solubility (Pennington, L. D., et al., The Necessary Nitrogen Atom: A Versatile High-Impact Design Element for Multiparameter Optimization. *J. Med. Chem.* 2017, 60, 3552-3579). Keeping the nitrogen (nicotinic) in the middle ring, the right side morpholine ring was substituted with piperidine ring (2c). This resulted in 6.4-fold loss of potency in comparison to 2a. However, replacement of morpholine with a phenyl ring on the right side resulted in compound 8a, which displayed nearly equal EP2 potency to 2a, but low aqueous solubility (Table 2). Incorporation of a methoxy group either at 3-position (8b), or methoxy or hydroxy at 2-position (8c-8d) on the phenyl ring improved the potency by 2-fold (~10 nM, Table 2) in comparison to 2a. Whereas, fluorine (8e) at 2-position reduced the potency by 2-fold in comparison to 2a, and 4-fold in comparison to 2-methoxy derivatives 8c. Incorporation of 4-acetamido group (8f), or two methoxy groups at 3- and 5-positions (8g) further enhanced the potency with $K_B$ values 4.4 and 2.9 nM respectively. To see if changing the location of nitrogen atom in the middle ring from meta-to-ortho (see o-m positional assignments in Scheme 2), derivatives 11a-c were synthesized. Compound 11a was 4-fold less potent than equivalent derivative 8b. Similarly, 11b was 11-fold less potent than equivalent derivative 8g, and compound 11c was 3-fold less potent than equivalent compound 8f. These observations indicate that nitrogen atom is preferred at m-position than at o-position of the middle ring (meaning nicotinic ring is more favorable than picolinic ring) for optimal potency. Furthermore, a pyrimidine derivative 14a was synthesized and it showed 2.9-fold less potency than the corresponding nicotinic ring compound 8c, but it has the same potency as 2a. Nonetheless, nicotinic middle ring maintains high EP2 Schild potency (<50 nM), except for 2b-c. Derivatives 8a-g and 14a displayed enhanced solubility in simulated gastric fluid at pH 2.0, whereas compounds 11a-c have not showed solubility enhancement in the simulated gastric fluid (Table 2), suggesting nicotinic ring derivatives have better aqueous solubility than picolinic ring derivatives. The nitrogen in the middle ring is not absolutely essential for EP2 potency, because compound with phenyl ring, 14c has also showed high EP2 potency (cf. 8c), but a fluorine-substitution on the middle phenyl ring drastically reduced the potency by 25-fold (cf. 14b vs. 14c or 8c) hinting that additional substitutions on the middle ring might not be tolerated for potency.

TABLE 2

Middle ring modified EP2 antagonists. Potency and aqueous solubility[a]

| Entry | R = | EP2 $K_B$ (nM) | Aqueous Solubility[b] (μM) | Solubility in SGF[c] (μM) |
|---|---|---|---|---|
| 2a | | 28.6 | 70 | ND |
| 2b | | 118 | 206 | ND |
| 2c | | 185 | ND | ND |

TABLE 2-continued

Middle ring modified EP2 antagonists. Potency and aqueous solubility[a]

| Entry | R = | EP2 $K_B$ (nM) | Aqueous Solubility[b] (μM) | Solubility in SGF [c] (μM) |
|---|---|---|---|---|
| 8a | pyridine-phenyl | 23.2 | 25 | >100 |
| 8b | pyridine-phenyl-3-OMe | 9.5 | 13 | >100 |
| 8c | pyridine-phenyl-2-OMe | 10 | 28 | >100 |
| 8d | pyridine-phenyl-2-OH | 11.5 | 8 | 50[e] |
| 8e | pyridine-phenyl-2-F | 48.4 | 22 | >100 |
| 8f | pyridine-phenyl-4-NHCOCH$_3$ | 4.4 | 25 | >100 |

TABLE 2-continued
Middle ring modified EP2 antagonists. Potency and aqueous solubility[a]
| Entry | R = | EP2 $K_B$ (nM) | Aqueous Solubility[b] (μM) | Solubility in SGF[c] (μM) |
|---|---|---|---|---|
| 8g | 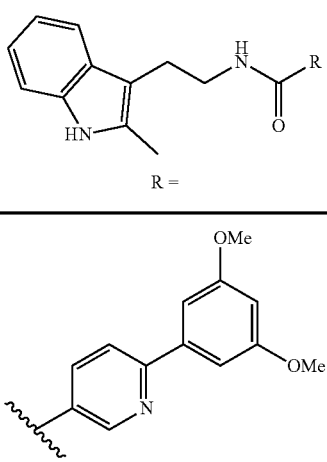 | 2.9 | 12 | >100 |
| 11a | 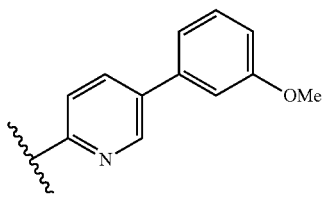 [SMILES: *c1ccc(-c2cccc(OC)c2)cn1] | 48.6 | 14 | 14 |
| 11b | 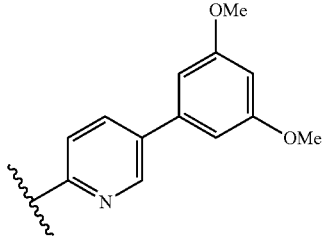 [SMILES: *c1ccc(-c2cc(OC)cc(OC)c2)cn1] | 33.6 | 10 | 10 |
| 11c | 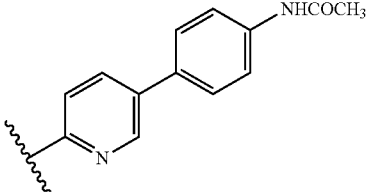 | 12.8 | 10 | 10 |
| 14a | 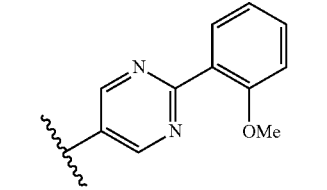 [SMILES: *c1cnc(-c2ccccc2OC)nc1] | 29.6 | 71 | >100 |
| 14b | 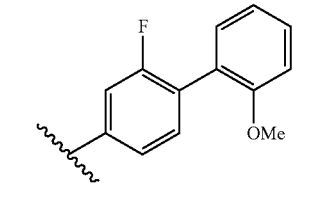 [SMILES: *c1ccc(-c2ccccc2OC)c(F)c1] | 250 | 10 | 10[d] |

TABLE 2-continued

Middle ring modified EP2 antagonists. Potency and aqueous solubility[a]

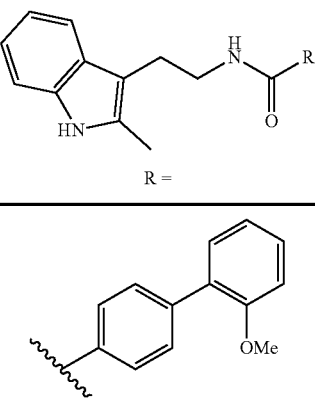

| Entry | R = | EP2 $K_B$ (nM) | Aqueous Solubility[b] (μM) | Solubility in SGF[c] (μM) |
|---|---|---|---|---|
| 14c | (biphenyl-OMe) | 7.7 | 5 | ND |

[a] The potency of the compounds is presented in the form of Schild $K_B$ values, which are calculated using the formula log (dr-1) = log $X_B$ − log $K_B$, where dr (dose ratio) = fold shift in $EC_{50}$ of $PGE_2$ by the antagonist compound, $X_B$ is antagonist concentration 1 μM. $K_B$ value indicates a concentration required to produce a 2-fold rightward shift of $PGE_2$ $EC_{50}$. $K_B$ values are average of 2 measurements run in duplicate.
[b] The solubility of the compounds is measured in PBS buffer (pH 7.4) with 1% DMSO by nephelometry.
[c] The numbers are derived by measuring solubility in simulated gastric fluid (SGF) at pH 2.0 with 1% DMSO by nephelometry.

Although the requisite EP2 potency is obtained for several analogs shown in Table 2, only compound 8c has displayed good selectivity (>100-fold) against other receptors (see Table 6 and next section for selectivity discussion). Moreover, when representative compounds (8c, 8d, 8g, 14a) from the Table 2 were tested for stability in mouse liver microsomes, they displayed very short half-life (Table 5). Therefore, additional novel derivatives were synthesized by keeping the middle ring as pyrimidine and modifying the third ring (Scheme 3). The other key difference between these set of derivatives shown in Table 3 in comparison to the ones shown in Table 2 is the NH functional group, which links the third ring and the middle pyrimidine ring. The NH group can enhance the molecular flexibility and potentially allow anionic salts to be made. 2-pyridyl derivative 20a was synthesized and tested. This compound displayed high EP2 potency with $K_B$=10.7 nM. Addition of methyl group (20b) or a fluorine (20c) at 4-position maintained high potency ($K_B$=<10 nM). Moving the methyl group from 4- to 6-position also maintained a high potency (cf. 20e vs. 20b), but similarly moving the fluorine atom to 6-position recued the potency by 16-fold (cf. 20f vs. 20c). A methoxy group at 6-position also maintained high EP2 potency (20h), whereas cyano-group reduced the potency by 23-fold (20g). The acetyl group on pyridine ring whether it is at 6-, 5- or 4-position (20j, 20l and 20k) reduced the potency by 4-, 20- and 12-fold respectively in comparison to 20b. A compound with bulkier group 3-hydroxybutane at 6-position showed 4-fold less potency than 20b. Similarly, tert-butyl group at 4-position reduced the potency by 5-fold (cf. 20d vs. 20b), or 6-position reduced by 13-fold (cf. 20n vs. 20e). A hydroxy group (20i) at 6-position eliminated the potency of the molecule ($K_B$>1000 nM) (Table 3). Incorporation of two methyl groups as in 20o did not have additive impact on the potency (cf. 20o vs. 20b or 20e). The 4-pyridyl derivative 20p was tested and showed complete loss of potency, whereas the 3-pyridyl derivative 20q regained the potency and shown nearly same potency as 20a. Addition of two methyl groups on 3-pyridyl ring (20r) similar to 20o indicated 10-fold loss of potency.

TABLE 3

Middle ring and right side ring modified EP2 antagonists. Potency and aqueous solubility[a]

| Compound ID | R = | EP2 $K_B$ (nM) | Aqueous Solubility[b] (μM) |
|---|---|---|---|
| 20a | 2-pyridyl | 10.7 | 27 |

TABLE 3-continued

Middle ring and right side ring modified EP2 antagonists. Potency and aqueous solubility[a]

| Compound ID | R = | EP2 K$_B$ (nM) | Aqueous Solubility[b] (μM) |
|---|---|---|---|
| 20b | 4-methylpyridin-2-yl | 8.0 | 25 |
| 20c | 4-fluoropyridin-2-yl | 6.4 | 15 |
| 20d | 4-tert-butylpyridin-2-yl | 44.5 | 5 |
| 20e | 6-methylpyridin-2-yl | 6.1 | 25 |
| 20f | 6-fluoropyridin-2-yl | 96 | 41 |
| 20g | 6-cyanopyridin-2-yl | 230 | 13 |
| 20h | 6-methoxypyridin-2-yl | 7.8 | 15 |

TABLE 3-continued

Middle ring and right side ring modified EP2 antagonists. Potency and aqueous solubility[a]

| Compound ID | R = | EP2 $K_B$ (nM) | Aqueous Solubility[b] (μM) |
|---|---|---|---|
| 20i | 6-hydroxypyridin-2-yl | 1220 | 10 |
| 20j | 6-acetylpyridin-2-yl | 32.5 | 5 |
| 20k | 4-acetylpyridin-2-yl | 104 | ND |
| 20l | 5-acetylpyridin-2-yl | 166 | ND |
| 20m | 6-(2-hydroxybutan-2-yl)pyridin-2-yl | 39 | 6 |
| 20n | 6-tert-butylpyridin-2-yl | 79.3 | 25 |

TABLE 3-continued

Middle ring and right side ring modified EP2 antagonists. Potency and aqueous solubility[a]

| Compound ID | R = | EP2 $K_B$ (nM) | Aqueous Solubility[b] (μM) |
|---|---|---|---|
| 20o | 4,6-dimethylpyridin-2-yl | 9.7 | 15 |
| 20p | pyridin-4-yl | >1000 | 38 |
| 20q | pyridin-3-yl | 8.3 | 17 |
| 20r | 2,6-dimethylpyridin-3-yl | 88.1 | 100 |

[a] Schild $K_B$ values are calculated similarly as indicated at Table 1 legend. $K_B$ values are average of 2 measurements run in duplicate.
ND = not determined
[b] The solubility of the compounds is measured in PBS buffer (pH 7.4) with 1% DMSO by nephelometry.[46]

Additional derivatives (Scheme 4) were synthesized by modifying left side indole moiety and the two carbon linker, keeping the middle ring as pyrimidine and the right side ring as 4,6-dimethyl pyridyl ring as constant. As shown in Table 4, a fluoro, chloro, methoxy, difluoro or dichloro derivatives 24a-e all retained high EP2 potency, whereas changing indole ring to pyrazolo-pyridine ring as in 24g reduced the potency by 32-fold in comparison to 20o. Moreover, substituting the methyl group at second position of indole with a trifluoromethyl group (24f) also reduced the potency by 8-fold. Modification to the linker with ketone group next to indole (24h) eliminated the potency, whereas a hydroxy group as in 24i recued the potency 23-fold in comparison to 20o suggesting unsubstituted ethylene linker is optimal for high EP2 potency within the scaffold. Overall, the SAR study on the leads indicated that a number of compounds exhibit high EP2 potency.

TABLE 4

Modifications at indole ring and linker regions of the scaffold. Potency and aqueous solubility[a]

| Entry | R = | EP2 $K_B$ (nM) | Aqueous Solubility[b] (μM) | Aqueous solubility of corresponding HCl salt in SGF[c] (μM) | Water solubility of corresponding HCl salt[d] (mM) |
|---|---|---|---|---|---|
| 20o | 2-methylindol-3-yl-ethyl | 9.7 | 150 | >250 | 2.52 |
| 24a | 5-F-2-methylindol-3-yl-ethyl | 13.0 | 5 | ND | 1.16 |
| 24aa (TG11-283HCL) | 7-F-2-methylindol-3-yl-ethyl | 1.7 | 150 | >250 | 2.64 |
| 24b | 5-Cl-2-methylindol-3-yl-ethyl | 28.3 | 20 | ND | ND |
| 24c | 5,7-diF-2-methylindol-3-yl-ethyl | 20 | ND | >100 | 1.73 |
| 24d | 5,7-diCl-2-methylindol-3-yl-ethyl | 25.1 | ND | ND | 2.38 |
| 24e | 5-MeO-2-methylindol-3-yl-ethyl | 8.8 | 20 | ND | ND |

TABLE 4-continued

Modifications at indole ring and linker regions of the scaffold. Potency and aqueous solubility[a]

| Entry | R = | EP2 $K_B$ (nM) | Aqueous Solubility[b] (μM) | Aqueous solubility of corresponding HCl salt in SGF[c] (μM) | Water solubility of corresponding HCl salt[d] (mM) |
|---|---|---|---|---|---|
| 24f | (indole with CF3) | 66 | 45 | ND | 0.7 |
| 24g | (pyrazolopyridine) | 254 | 70 | ND | ND |
| 24h | (indole ketone) | >1000 | ND | ND | ND |
| 24i | (indole with OH) | 183 | 57 | ND | ND |

[a]Schild $K_B$ values are calculated similarly as indicated at Table 1 legend. $K_B$ values are average of 2 measurements run in duplicate, except compound 20o for which the values are average of 6 repeats
[b]The solubility of the compounds is measured in PBS buffer (pH 7.4) with 1% DMSO by nephelometry.[46]
[c]The solubility of compounds measured in simulated gastric fluid at pH 2.0 by nephelometry. Compound 24d is a milky-white solution in DMSO and 24 h is an inactive compound. Therefore, their solubility is not determined by nephelometry, however, 24d. HCl is highly water soluble.
[d]Water solubility is determined by 24 h shake flask thermodynamic solubility method in neat water. Briefly, the compounds were dissolved in water at 2 mg/mL and shaken at 2200 rpm for 24 h. Then, the solutions were filtered through 0.2 μ syringe filters and analyzed the area under the curve (AUC) using HPLC, along with standard DMSO solution of each compound.
ND = not determined.

TABLE 5

Mouse liver microsomal (MLM) stability of selected novel EP2 antagonists[a]

| Compd. | MLM T½ (minutes) |
|---|---|
| 3a | <2 |
| 8c | 2.9 |
| 8d | 13 |
| 8g | 2.9 |
| 14a | 6.5 |
| 20b | 8 |
| 20c | 17 |
| 20e | 12 |
| 20f | 96 |
| 20h | 16 |
| 20o | 17 |
| 24a | 17 |
| 24aa | 23 |
| 24c | 26 |
| 24e | 15 |
| 24i | 56 |

[a]The compounds at 1 μM were incubated in 0.125 mg/mL liver microsomes that are activated with addition of NADPH (final concentration 1 mM) and quenched the reaction at 0, 5, 15, 30, 60 and 120 min using ice-cold acetonitrile. The % compound remaining was measured using LC-MS/MS from which half-life was calculated. The work was done at CRO laboratories.

Determination of Aqueous Solubility of EP2 Compounds

To test aqueous solubility, a kinetic assay was used in which the compounds were dissolved in DMSO then serial diluted with phosphate buffered solution (PBS) at pH 7.4, maintaining 1% DMSO in the solutions. Solubility was then determined by nephelometry. Several compounds shown in Table 2 and 3 displayed moderate solubility (<100 μM) in PBS at pH 7.4. However, several of those compounds including 8a-c, 8e-g, 14a, 20o, 24c have shown >100 μM aqueous solubility when determined in simulated gastric fluid (pH 2.0), suggesting that the intrinsic basic nitrogen can create salts that further increase solubility and facilitate the formulation. On this notion, compounds 20o, 24a, c, d and 24f have been converted to hydrochloride salts by stirring them in dichloromethane using dilute hydrochloride solution.

To test whether the hydrochloride salt compounds (20o, 24a, c d and 24f) are soluble in water, a thermodynamic assay (shake flask method) was used where the compounds are shaken (2 mg/mL, at 2200 rpm) in neat water and the soluble fraction was measured against standard DMSO solutions by HPLC or LC-MS/MS quantitation methods. As shown in Table 4, the hydrochloride salt compounds displayed millimolar level aqueous solubility in water. The salt forms did not show increased solubility in PBS buffer at pH 7.4 by nephelometry method in comparison to their neutral compounds. This is likely due to a drop in pH in neat water, in comparison to a buffer. Indeed, the water pH was reduced from 6.4 to 3.5 when 20o.HCl was dissolved at 2 mg/mL.

Prostacyclin Confers Atheroprotection on Female Mice. Science 2004, 306, 1954-1957). Thus, the selectivity of several potent EP2 antagonists ($K_B$<50 nM for EP2) were determined against DP1 first, and if any compound showed >100-fold selectivity to DP1, then it was tested against EP4 and IP receptors. As shown in Table 6, compounds 8a-b, 8e, and 11a-b showed <100-fold selectivity against the DP1 receptor, thus they were not tested against EP4 and IP receptors. The compounds 8c, 14a, 20a, 20c, 20e, 20h, 20o, and 24a-c displayed excellent selectivity against DP1, and subsequently against EP4 and IP receptors. However, compounds 8g and 24c displayed <200-fold selectivity against at least one of the three (DP1, EP4, and IP) receptors suggesting selectivity will depend on the individual structure of the molecule within the scaffold. Several compounds in the class for cytotoxicity in the C6-glioma cell line were tested. As exemplified in Table 6, selected compounds including 20o displayed no cytotoxicity until 50 μM indicating >2100-fold in vitro therapeutic index ($CC_{50}/EP_2\ K_B$), except compound 8c which showed $CC_{50}$ 21 μM with a therapeutic index of 2100-fold.

TABLE 6

EP2 Potency, selectivity index (S.I), and cytotoxicity ($CC_{50}$) of selected novel EP2 antagonists[a]

| Entry | EP2 $K_B$ (nM) | DP1 $K_B$ (μM) | S.I. (DP1/EP2) | EP4 $K_B$ (μM) | S.I (EP4/EP2) | IP $K_B$ (μM) | S.I (IP/EP2) | $CC_{50}$ (μM) |
|---|---|---|---|---|---|---|---|---|
| 8a | 23.2 | 1.0 | 42 | ND | ND | ND | ND | ND |
| 8b | 9.5 | 0.9 | 95 | ND | ND | ND | ND | ND |
| 8c | 10 | 3.0 | 300 | 22.8 | 2280 | 3.47 | 350 | 21 |
| 8e | 48.4 | 0.8 | 16 | ND | ND | ND | ND | ND |
| 8g | 2.9 | 1.2 | 410 | 3.91 | 1350 | 0.73 | 25 | >50 |
| 11a | 48.6 | 1.7 | 35 | ND | ND | ND | ND | ND |
| 11b | 33.6 | 0.5 | 15 | ND | ND | ND | ND | ND |
| 14a | 29.6 | 6.6 | 300 | 15.3 | 517 | 21.5 | 730 | >50 |
| 20a | 10.7 | >10 | >900 | 6.7 | 630 | >10 | >900 | >50 |
| 20c | 6.4 | 3.2 | 500 | >10 | >1500 | >10 | >1500 | >50 |
| 20e | 6.1 | 2.25 | 360 | >10 | >1500 | >10 | >1500 | >50 |
| 20h | 7.8 | >10 | >1280 | 6.7 | 860 | >10 | >1280 | >50 |
| 20o | 9.7 | 7.32 | 750 | 5.3 | 550 | >10 | >1000 | >50 |
| 20q | 8.3 | 1.77 | 213 | >10 | >1200 | >10 | >1200 | >50 |
| 24a | 13.0 | 9.0 | 692 | 3.1 | 240 | >10 | 770 | >50 |
| 24b | 28.3 | 8.2 | 290 | >10 | >350 | >10 | >350 | >50 |
| 24c | 20.0 | 8.2 | 410 | 3.8 | 193 | >10 | >500 | ND |

[a]EP2 $K_B$ values are from average of 2 independent experiments run duplicate, except for 20o. EP4, DP1 and IP $K_B$ values are from 2 independent experiments run in duplicate. $K_B$ values for EP2 are in the nanomolar scale, whereas $K_B$ values for other receptors are shown in micromolar scale. $CC_{50}$ (concentration required to kill 50% C6glioma cells) values are from 1-2 experiments run in triplicate using internal standard doxorubucin, which showed $CC_{50}$ = 0.9 μM.

This observation is in line with findings that the neutral compounds have higher solubility in simulated gastric fluid (pH 2.0) than in PBS at pH 7.4. Overall, the hydrochloride salts of compounds 20o, 24a, 24c and 24d showed 2.52, 1.16, 1.73 and 2.38 mM solubility in neat water (Table 4).

Selectivity Assessment of Novel EP2 Antagonists

The structural identity among the prostanoid receptor family is rather low. EP1, EP2, EP3 and EP4 share only 20-30% structural homology (Sugimoto, Y., et al., Prostaglandin E Receptors. J. Biol. Chem. 2007, 282, 11613-11617). In contrast, EP2 is more homologous to DP1 (44%) and IP receptors (40%). In terms of cellular signaling, EP2, EP4, DP1 and IP induce cAMP mediated cell signaling, whereas EP1 promotes $Ca^{2+}$ mediated signaling and EP3 inhibits cAMP mediated signaling. Functionally, EP2 and DP1 receptors seem to promote inflammation in a variety of disease conditions, whereas EP4 seems to act as pro and anti-inflammatory, and the IP receptor seems to have cardioprotective role (Egan, K. M., et al., Cox-2-Derived DMPK Properties of Novel EP2 Antagonists Several derivatives were tested in pooled liver microsomal fractions to determine the half-life and intrinsic clearance by the mouse liver, and to project in vivo pharmacokinetics. The starting compound 2a was metabolized quickly in liver microsomes (Table 5). To understand the potential metabolites, compound 2a was incubated in mouse liver microsomes and investigated metabolites after 5 minutes. As shown in Scheme 2, the major metabolite is the amide bond cleaved product D (MW 190 Da), which can be formed via intermediate A that would be further cleaved to generate fragments B/C (MW 158 Da) and D. The compound D can also be generated via a vinylamine F (MW 362 Da) intermediate, formation of which can be envisioned via hydroxylation at the $CH_2$ unit (E) next to 3-indole ring. Therefore, compounds blocking the $CH_2$ site with a hydroxy group (e.g. 24i) were synthesized. The half-life of 24i in liver microsomes increased by 3-fold ($t_{1/2}$, 57 min) compared to its equivalent 20o, which showed 17 minutes of half-life (Table 5). However, the hydroxylated derivatives displayed reduced EP2 potency compared with the equivalent compounds. (cf. 24i displayed about 19-fold less potency than 20o, Table 4). In a similar experiment, the tetrazole compound 3 did not produce any fragments even after 20 minutes of incubation in liver microsomes, suggesting the metabolic hydroxylation or cleavage also depends on the right side moiety (Scheme 5). The mouse liver microsomal half-life data presented in Table 5 also indicate that a fluorine atom in place of metabolically prone methyl group enhances the stability. For example, a fluoro-derivative 20c has 2-fold higher half-life in comparison to 20b, likewise 20f has 8-fold higher half-life than 20e. Regrettably, 20c is unstable in vivo, and 20f displayed less potency to EP2 receptor (Table 3), therefore, these compounds are not promoted for further studies.

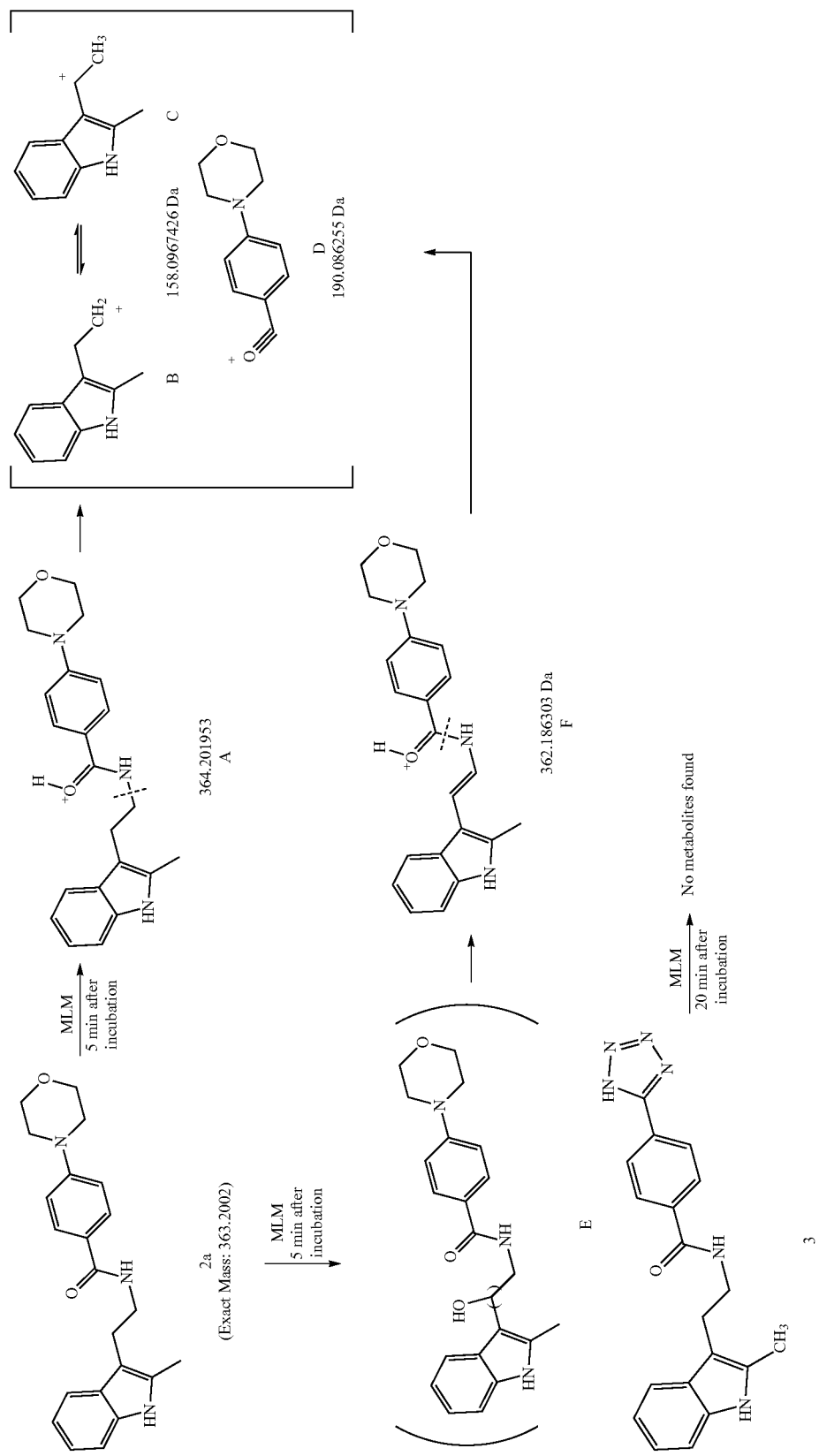
Scheme 5. Metabolites identified from the lead EP2 antagonists in mouse liver microsomes. Compound 2a was incubated for 5 min and metabolic fragments (A-F) were detected using LC-MS/MS. Unlike compound 2a, compound 3 has not shown any metabolic fragments even after 20 min of incubation in mouse liver microsomes.

MIPO scores indicated that several EP2 antagonists in the class as exemplified in Table 7, display a desired MPO score of ≥4, but several others do not achieve the desired score >4 derived using their physicochemical properties. Compounds ≥4 MIPO score should have desirable CNS activity and permeability features. However, the compounds 3 while it displayed >5 score does not have good permeability properties and does not get in to the brain (Table 7). A corollary which displayed ER ratio 16 indicating it may be a substrate for efflux pumps (Table 7). On the other hand, the compound 20 found to show good permeability and showed similar efflux ratio in the presence and absence of an efflux pump inhibitor verapamil, confirming that it is not the substrate of efflux pumps. (Table 7). Moreover, compound 20s showed 0.4% plasma protein unbound fraction in mouse plasma proteins.

TABLE 7

BBB-permeability, mouse and human liver microsomal stability, key pharmacokinetic properties for selected compounds[a]

| Entry | MLMt$_{1/2}$(min) | HLM t$_{1/2}$ (min) | In vivo plasma t$_{1/2}$ (h)[a] | Brain-to-plasma ratio[b] | Permeability across MDR1-MDCK cell line[c] | Efflux ratio (B − A/ A − B) | MPO score[d] (Desired score for CNS permeability ≥4) |
|---|---|---|---|---|---|---|---|
| 1 | 10 | 11 | 1.7 (ip/po, 10 mg/kg dose) | 1.7 | B − A: 27.1 × 10$^{-6}$ cm/s<br>A − B: 25.4 × 10$^{-6}$ cm/s | 1.1 | 4.7 |
| 3 | >60 | >60 | >6 h (po, 10 mg/kg) | 0.02 | B − A: 0.12 × 10$^{-6}$ cm/s<br>A − B: 0.41 × 10$^{-6}$ cm/s | 0.3 | 5.0 |
| 8c | 2.9 | ND | <1 h (ip, 10 mg/kg) | 0.5 | B − A: 51.0 × 10$^{-6}$ cm/s<br>A − B: 19.8 × 10$^{-6}$ cm/s | 2.6 | 3.8 |
| 8g | 2.9 | ND | <1 h (ip, 10 mg/kg) | ND | B − A: 55.3 × 10$^{-6}$ cm/s<br>A − B: 20.6 × 10$^{-6}$ cm/s | 2.7 | 3.7 |
| 14a | 6.5 | ND | <1 h (ip, 10 mg/kg) | 0.16 | B − A: 71.1 × 10$^{-6}$ cm/s<br>A − B: 4.54 × 10$^{-6}$ cm/s | 16 | 4.3 |
| 20o TG11-77.HCl | 17 | 87.7 | 1.1 h (IP, 10 mg/kg) & 2.4 h (po, 50 mg/kg) | 0.4 | B − A: 21.5 × 10$^{-6}$ cm/s<br>A − B: 10.2 × 10$^{-6}$ cm/s | 2.1 | 3.6 |
| 24aa TG11-283HCl) | 23 | ND | 5.4 h (ip, 20 mg/kg) | 0.4 | IP | IP | IP |
| In the presence of a pgp-inhibitor (verapamil) | | | | | | | |
| 20o | | | | | B − A: 22.2 × 10$^{-6}$ cm/s<br>A − B: 13.2 × 10$^{-6}$ cm/s | 1.7 | |

[a]MLM = mouse liver microsomes; HLM = human liver microsomes. In liver microsomal stability tests, 1 μM compound test compound was incubated with 0.5 mg/mL liver microsomes for compounds 1 and 3. However, other compounds in the table were incubated with 0.125 mg/mL liver microsomal concentration. The plasma half-life is estimated based on the 3-time point B/P ratio studies conducted with single injection of 10 mg/kg dose to male mice. A full-scale pharmacokinetic study with 8-time points was done for selected compounds (1, 3, 20o).
[b]Brain-to-plasma are derived from peak concentrations observed at 0.5 h after injection into mice.
[c]BBB potential was determined using MDR1-expressed cell monolayers. All these studies are conducted at CRO laboratories following industry standard procedures.
[d] See Table 1 for the physicochemical properties used to calculate the MPO score.

to this, the current lead compound 20o.HCl showed <4 MPO score, yet crosses the blood-brain-barrier with in vivo brain-to-plasma ratio 0.4. Likewise, compounds 8c, 8g and 14a behaved similarly. Overall, a positive correlation was seen between MPO score to in vivo brain to plasma ratio. Nonetheless, the MPO score does not quantitatively predict the brain permeability. Several compounds were tested for permeability across MDR1 expressed MDCK cell line to investigate the potential of blood brain barrier (BBB) permeability within the class. As shown in Table 7, many of these compounds have good passive permeability from the apical-to-basolateral (A-B) side as well as the basolateral-to-apical side (>0.6×10$^{-4}$ cm/s) in comparison to compound 3. and their efflux ratio is <3, except for compound 14a To determine in vivo brain-to-plasma ratio in mice, several compounds were tested whose mouse liver microsomal stability was greater than 15 min, by administering a dose of 10 mg/kg via intraperitoneal injection. Analysis of the compound concentration in the plasma and the brain tissues at 0.5, 2, and 4 h time points suggested that most of these compounds, exemplified as in Table 7 for 8c, 8g & 14a, will have a plasma half-life below 1 h, except compound 20o. A subsequent pharmacokinetic analysis on 20o.HCl with concentration analysis at 8-time points after a single i.p. injection (10 mg/kg) (FIG. 10) indicated that it has terminal plasma half-life 1.1 h with clearance rate of 124.1 mL/min/kg and brain-to-plasma ratio of 0.4. Additional studies with oral gavage dosing (50 mg/kg, B.I.D. dosing 8h apart) indicated that the plasma half-life could be extended to 2.4 h for 20o.HCl.

Competitive Mode of EP2 Antagonism by 20o.HCl and Derivatives.

To determine whether the novel derivatives in this class exhibit competitive antagonism of EP2, several compounds were tested in a concentration-response manner against $PGE_2$ concentration effect on EP2 receptors. The Schild $K_B$ indicates the antagonist concentration required for a two-fold rightward shift in the $PGE_2$ concentration-response curve. Schild $K_B$ values are derived by the equation log (dr−1)=log $X_B$–log $K_B$, where dr=dose ratio, i.e. the fold shift in agonist $EC_{50}$ caused by the antagonist, $X_B$ is antagonist concentration. As illustrated in FIG. 11B, a linear regression of log (dr−1) on log $X_B$ with slope of unity characterizes a competitive antagonism. A smaller $K_B$ value indicates a higher inhibitory potency. As shown in FIGS. 11A and C, compound 20o (TG11-77 neutral and the hydrochloride salt form) induced a concentration-dependent, parallel rightward shift in the $PGE_2$ concentration-response curve. Schild regression analyses (FIG. 11B) is consistent with a competitive mechanism of antagonism on EP2 with average Schild $K_B$ 9.7 nM and average slope value 1.05. The average $K_B$ value is used throughout. Moreover, several other compounds synthesized in this class displayed a concentration-dependent rightward shift of $PGE_2$ $EC_{50}$ and with slope of unity. Thus, the mechanism is competitive in general for the class of EP2 antagonists presented in this study. However, compound 20o did not show a concentration-dependent inhibition of DP1 receptor, indicating it is selective for EP2 over DP1 with selective index (DP1 $K_B$/EP2 $K_B$) of 750-fold. Moreover, this compound also showed high selectivity against EP4 and IP receptors with selective index of 550-fold and >1000-fold respectively (Table 6).

EP2 Antagonists Display Anti-Inflammatory Properties in a Novel Microglia Cell Line Expressing Human EP2.

The EP2 receptor acts as an immunomodulator with exacerbating role in chronic neurodegenerative disease such as epilepsy and Alzheimer's disease. EP2 receptors also play an exacerbating role in chronic inflammatory diseases such as rheumatoid arthritis, inflammatory bowel disease (colitis) and endometriosis (Greaves, E., et al., EP2 Receptor Antagonism Reduces Peripheral and Central Hyperalgesia in a Preclinical Mouse Model of Endometriosis. *Sci. Rep.* 2017, 7, 44169-44178; Sheibanie, A. F., et al., Prostaglandin E2 Exacerbates Collagen-Induced Arthritis in Mice through the Inflammatory Interleukin-23/Interleukin-17 Axis. *Arthritis Rheumatol.* 2007, 56, 2608-2619; Sheibanie, A. F., et al., The Proinflammatory Effect of Prostaglandin E2 in Experimental Inflammatory Bowel Disease is Mediated through the Il-23→Il-17 Axis. *J. Immunol.* 2007, 178, 8138-8147). To determine whether the new EP2 antagonists are anti-inflammatory, several of these EP2 antagonists, including 20o (TG11-77), were tested for anti-inflammatory activity in vitro. A routine isolation of microglia from mouse brain proved to be low throughput and these primary cells behave variably depending on the animal. Thus, a hEP2-BV2 cell line was created, a mouse microglia cell line overexpressing human EP2 receptors (Rojas, A., et al., Novel Microglia Cell Line Expressing the Human EP2 Receptor. *ACS Chem. Neurosci.* 2019, 10, 4280-4292).

To determine whether there is a correlation between the potency of EP2 antagonists in the cAMP-production assay and their ability to inhibit inflammatory gene expression in the BV2-hEP2 cell line, four selected EP2 antagonists were tested (3, 20o, 26 (TG4-155)(Jiang, J., et al., Role of Prostaglandin Receptor EP2 in the Regulations of Cancer Cell Proliferation, Invasion, and Inflammation. *J. Pharmacol. Exp. Ther.* 2013, 344, 360-367) and 27 (TG8-237) (Ganesh, T., et al., Peripherally Restricted, Highly Potent, Selective, Aqueous-Soluble EP2 Antagonist with Anti-Inflammatory Properties. *Mol. Pharm.* 2018, 15, 5809-5817)) with $K_B$ values ranging between 2 and 50 nM. The percent inhibition of inflammatory genes is plotted against log of multiple Schild $K_B$ values. The results show that the inhibition of cytokines was positively correlated to their respective Schild $K_B$, suggesting the higher the potency of antagonists in the cAMP assay, the lower the concentration required to display maximum effect on the inflammatory genes.

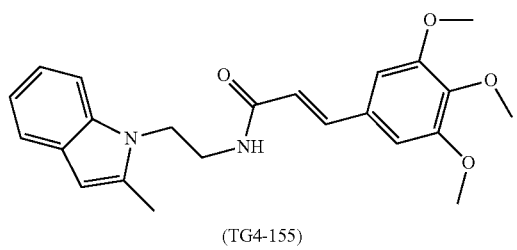

(TG4-155)

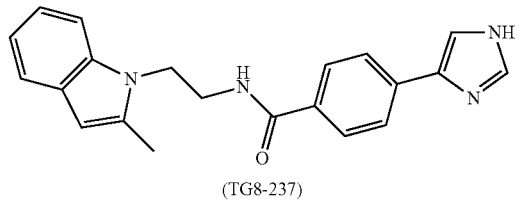

(TG8-237)

Pharmacological Data TG11-283 HC Salt (24aa) is Presented in Tables 4, 5 and 7.

Compounds containing either one or two nitrogen atoms in the middle ring seem to show high aqueous-solubility in simulated gastric fluid (SGF) at pH 2.0. By taking advantage of nitrogen atoms, hydrochloride salts for compounds were synthesized. The compound (TG11-77 HCl) showed 1 mg/mL water solubility, which facilitates the administration of this agent in drinking water by oral continuous feeding method.

The aqueous solubility of EP2 antagonists in phosphate buffered saline (PBS) was determined at pH 7.2 and simulated gastric fluid (SGF) at pH 2.0 in 1% DMSO, by nephelometry or by the classical shake-flask method in neat water and analyzed by LC-MS/MS. Several derivatives displayed >100 µM aqueous solubility in PBS at pH 7.2. The solubility for several compounds was further increased in SGF solution at pH 2.0.

Figure 1A:
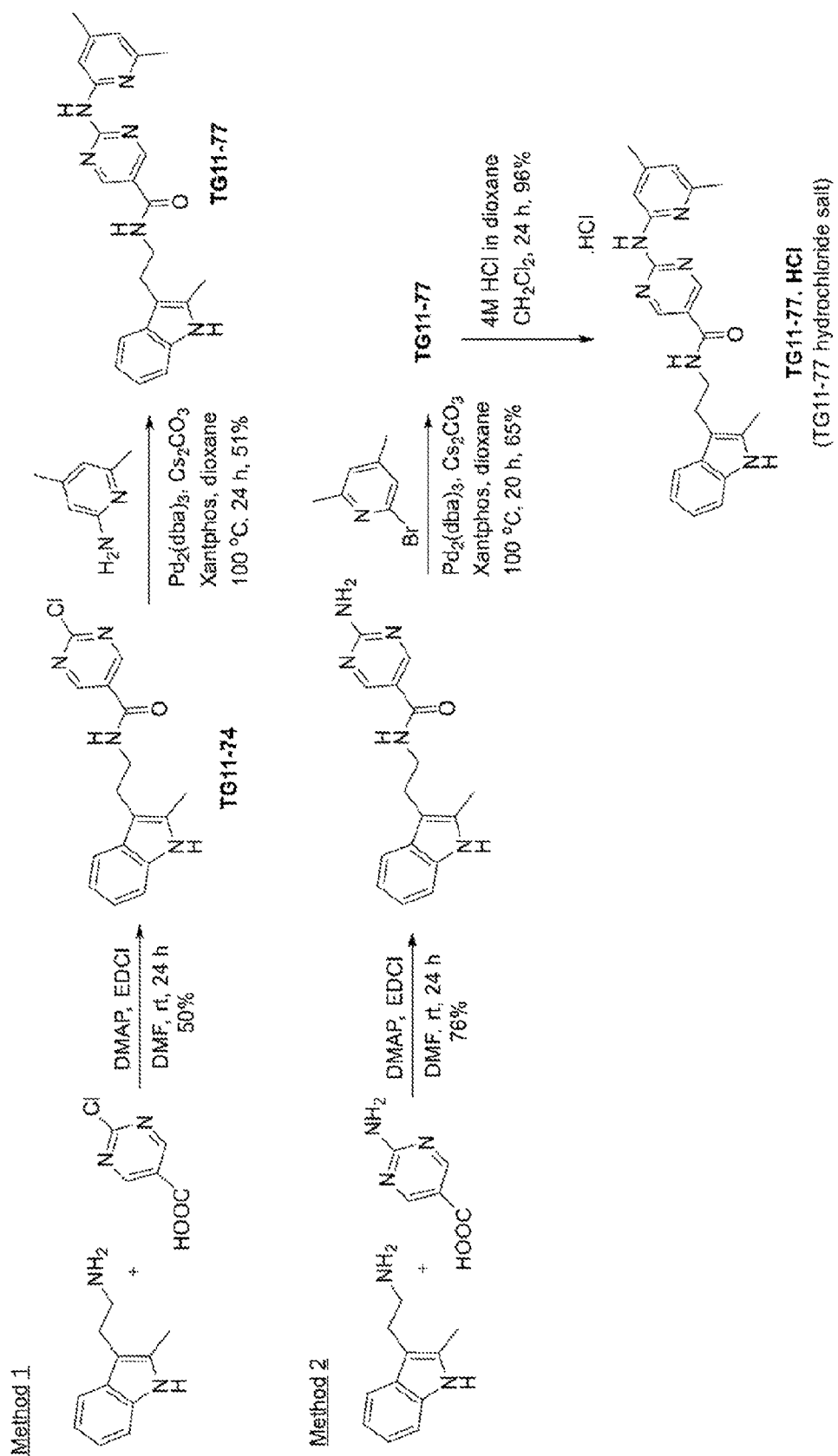
FIG. 1A illustrates the synthesis of TG11-77 and TG11-77HCl.
Figure 1B:
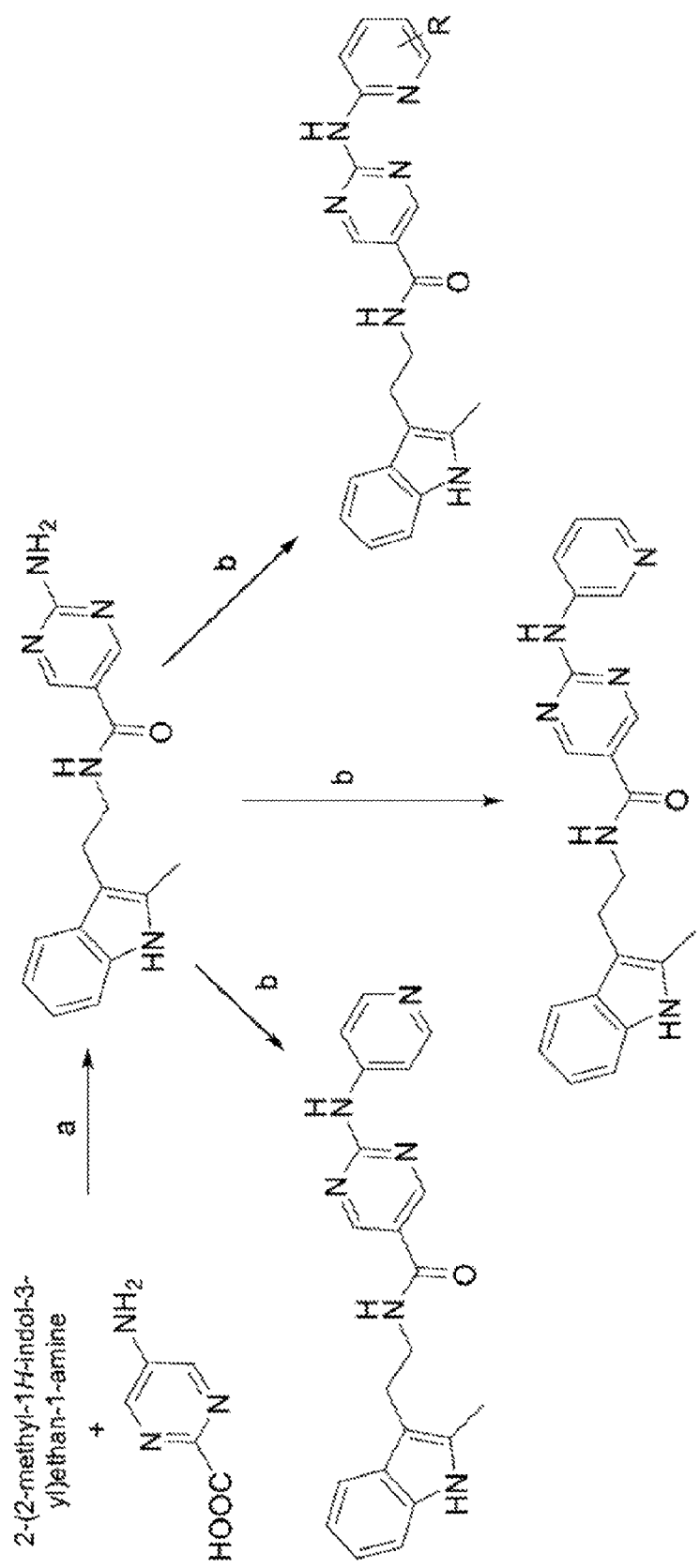
FIG. 1B illustrates the synthesis of derivatives using the methods provided for in FIG. 1 and appropriately modified starting materials, (a) is DMAP EDCl, rt, 24 h, (b) R4-Br, $Pd_2(dba)_3$, $Cs_2CO_3$, Xantpos, dioxane, 100 C, 24 h, or R5-B(OH)$_2$, PD(PPh$_3$)$_4$, Sat. $Na_2CO_3$, toluene, ethanol, 100 C, 24 h.
Figure 1C:
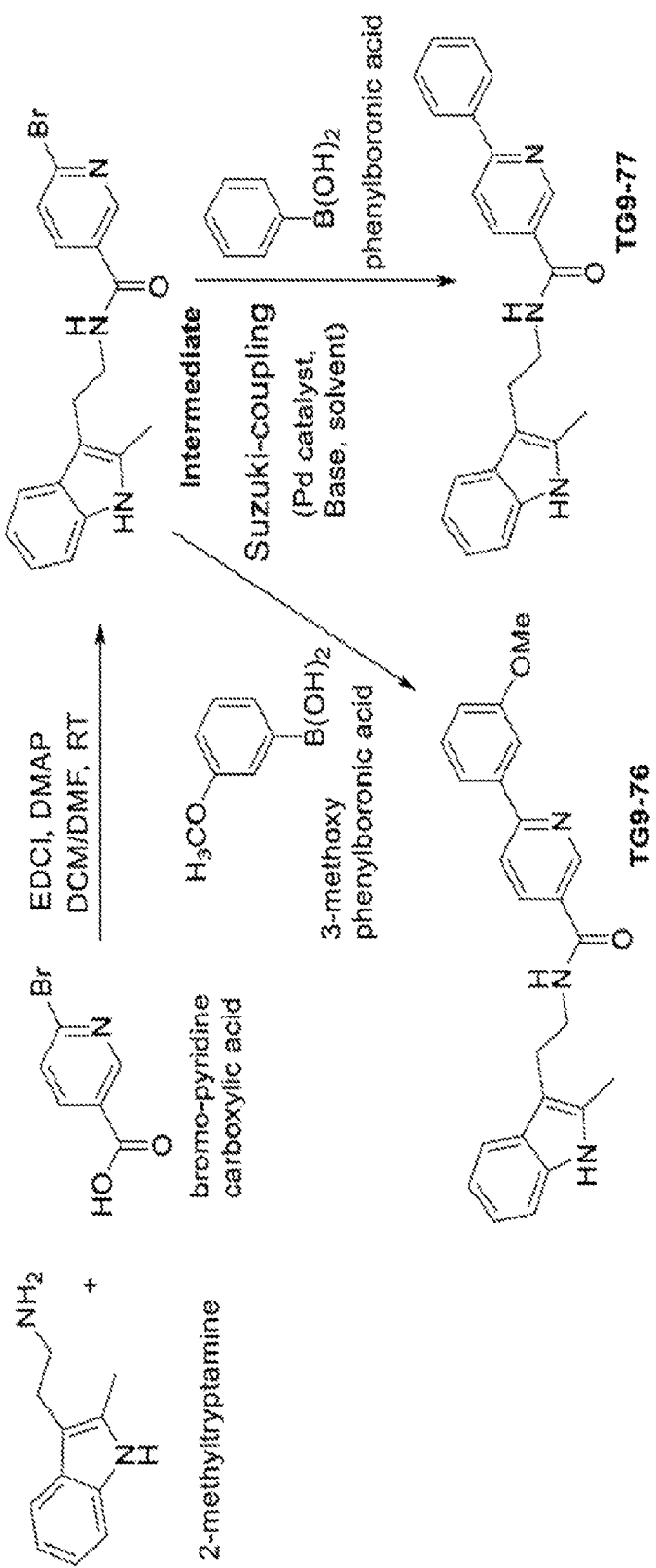
FIG. 1C illustrates the synthesis of embodiments of this disclosure.
Figure 1D:
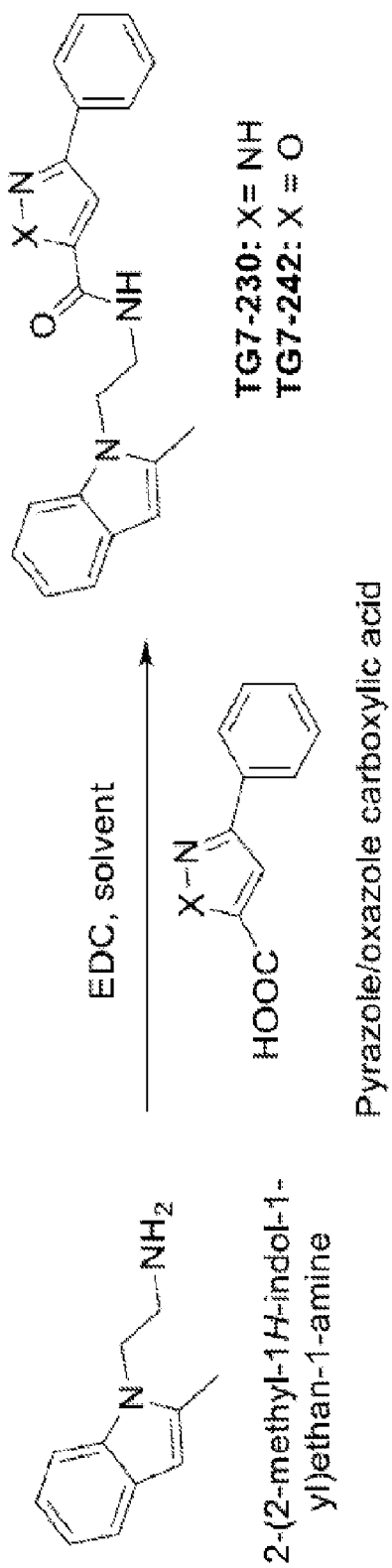
FIG. 1D illustrates the synthesis of embodiments of this disclosure.
Figure 1E:
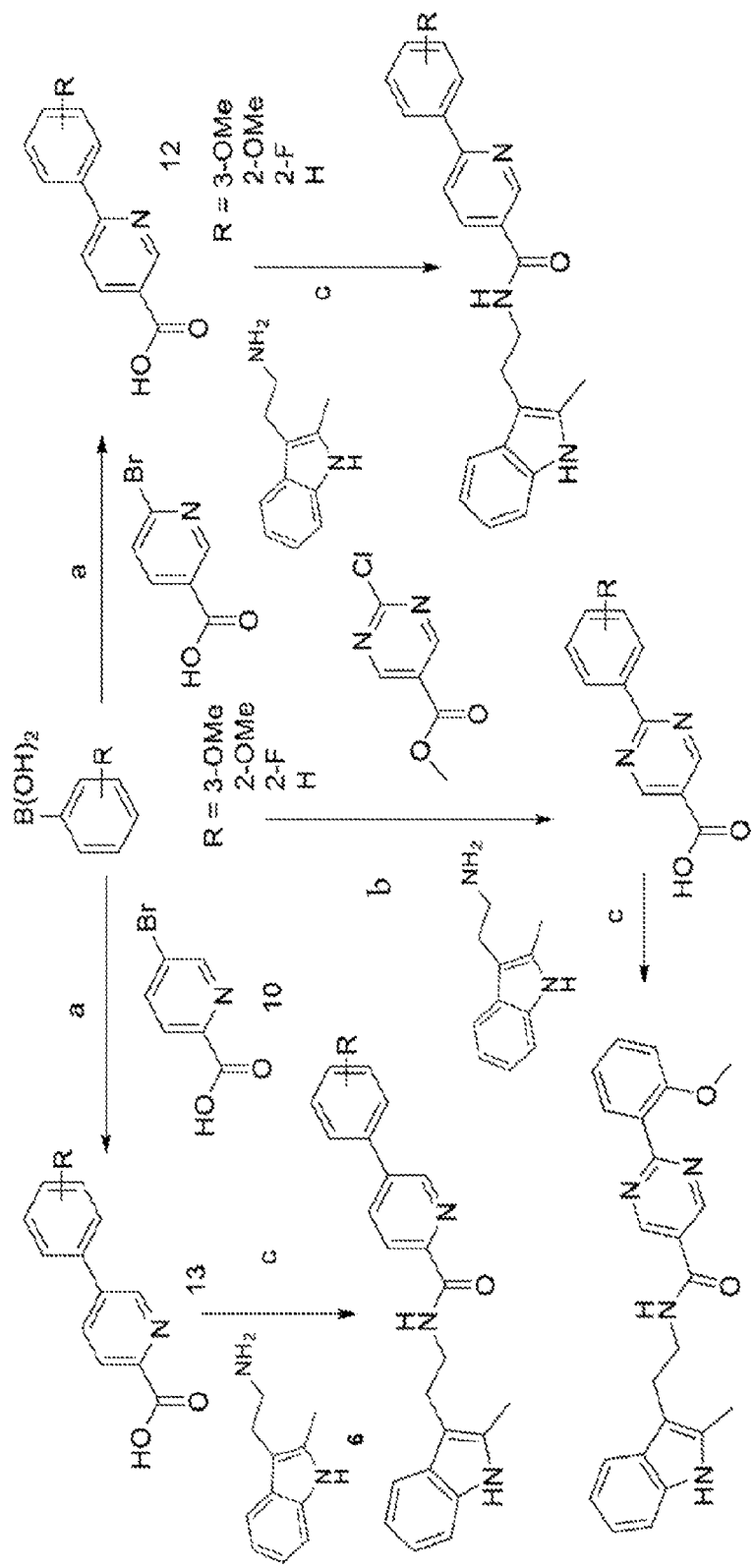
FIG. 1E illustrates the synthesis of embodiments of this disclosure.
Figure 2A:
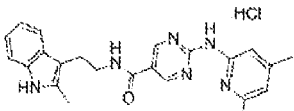
FIG. 2A illustrates compounds of this disclosure.
Figure 2A:
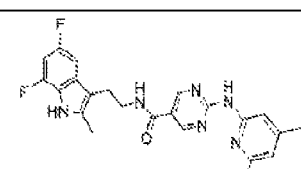
Figure 2A:
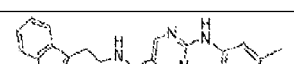
Figure 2A:
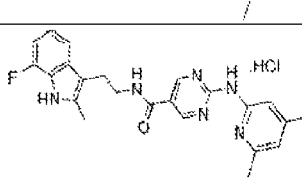
Figure 2A:
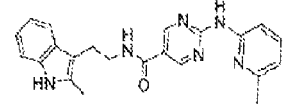
Figure 2A:
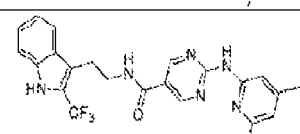
Figure 2A:
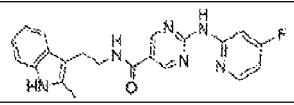
Figure 2A:
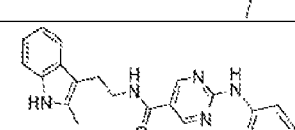
Figure 2A:
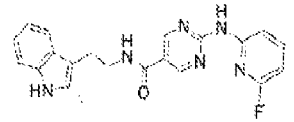
Figure 2A:
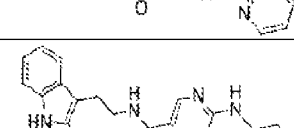
Figure 2A:
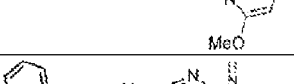
Figure 2A:
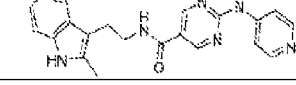
Figure 2A:
Figure 2A:
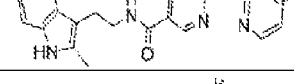
Figure 2A:
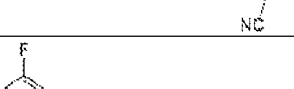
Figure 2A:
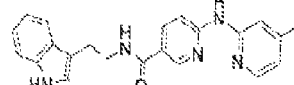
Figure 2A:
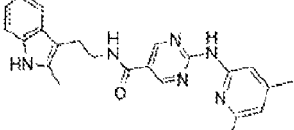
Figure 2A:
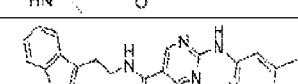
Figure 2A:
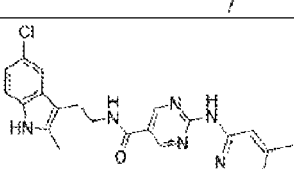
Figure 2A:
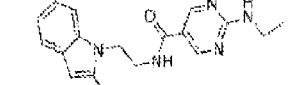
Figure 2A:
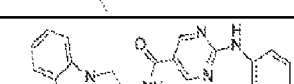
Figure 3A:
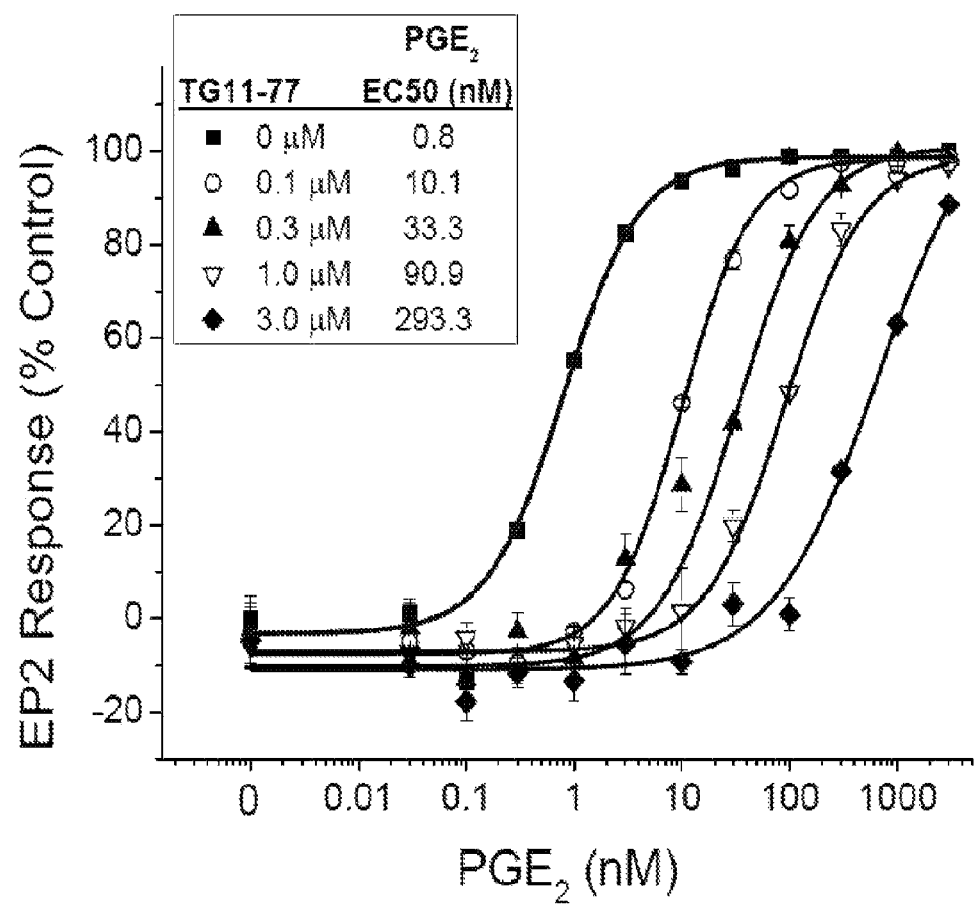
FIG. 3A shows data indicating Compound TG11-77 inhibited PGE2-induced human EP2 receptor activation in a concentration dependent manner. EP2 antagonists were subjected to ADME tests, including aqueous solubility, liver microsomal stability, inhibition of CYP450 enzymes, and blood-brain-barrier permeability. From these studies, compounds that displayed acceptable ADME characteristics were tested for in vivo pharmacokinetics with various routes (intravenous, intraperitoneal, oral delivery), various dosing amounts and regimens (5, 10, 25, 100 mg/kg/day, single dose, or b.i.d. dosing). The compound TG11-77 displayed excellent EP2 potency (9.7 nM) and >300-fold selectivity against DP1, EP4 and IP receptors, and no significant cytotoxicity up to 50 µM.
Figure 3B:
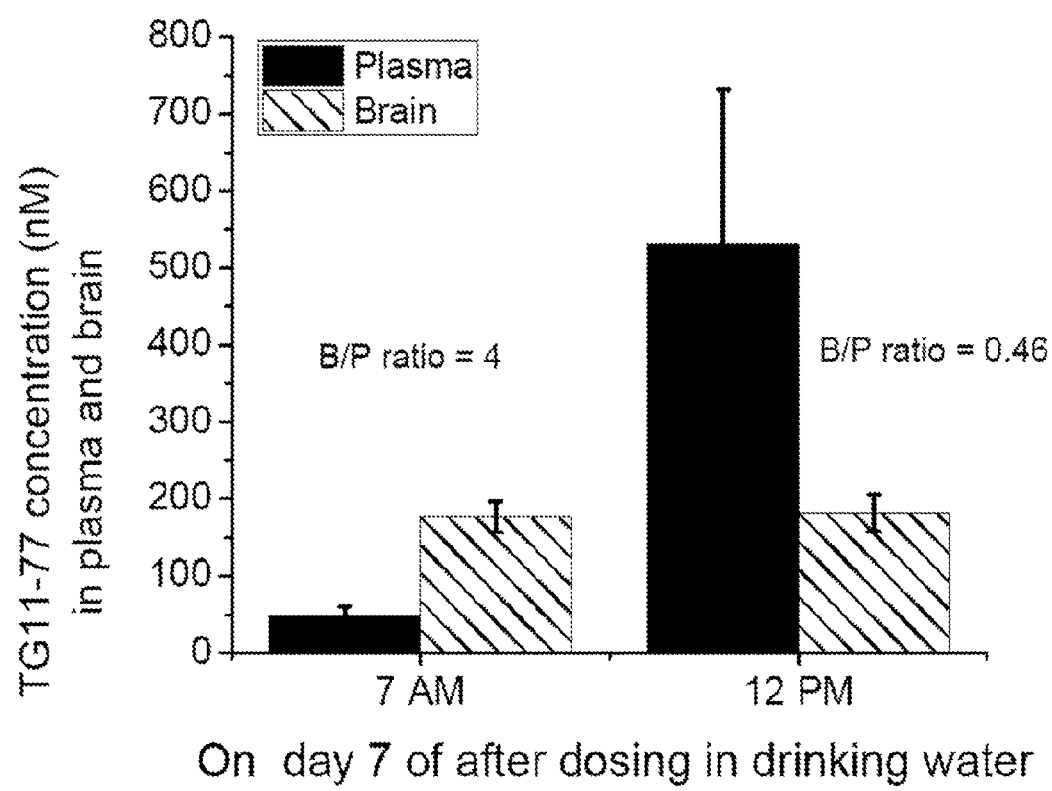
FIG. 3B shows brain-to-plasma ratio of TG11-77 HCl in C57BL6 mice (n=4 in each time point) dosing after 1 week. TG11-77 HCl was prepared at 0.5 mg/mL in water and supplied ad-libitum; a dose of ~100 mg/kg/day was projected from this solution based on the average water consumption by a mouse per day. Animals (n=4) were sacrificed in the morning and in the afternoon to compare the drug levels in a given day. The plasma concentration was low in the morning compared to afternoon, but the brain levels were consistent. The density of brain tissue is assumed as 1, to calculate the concentration in nM units.
Figure 4:
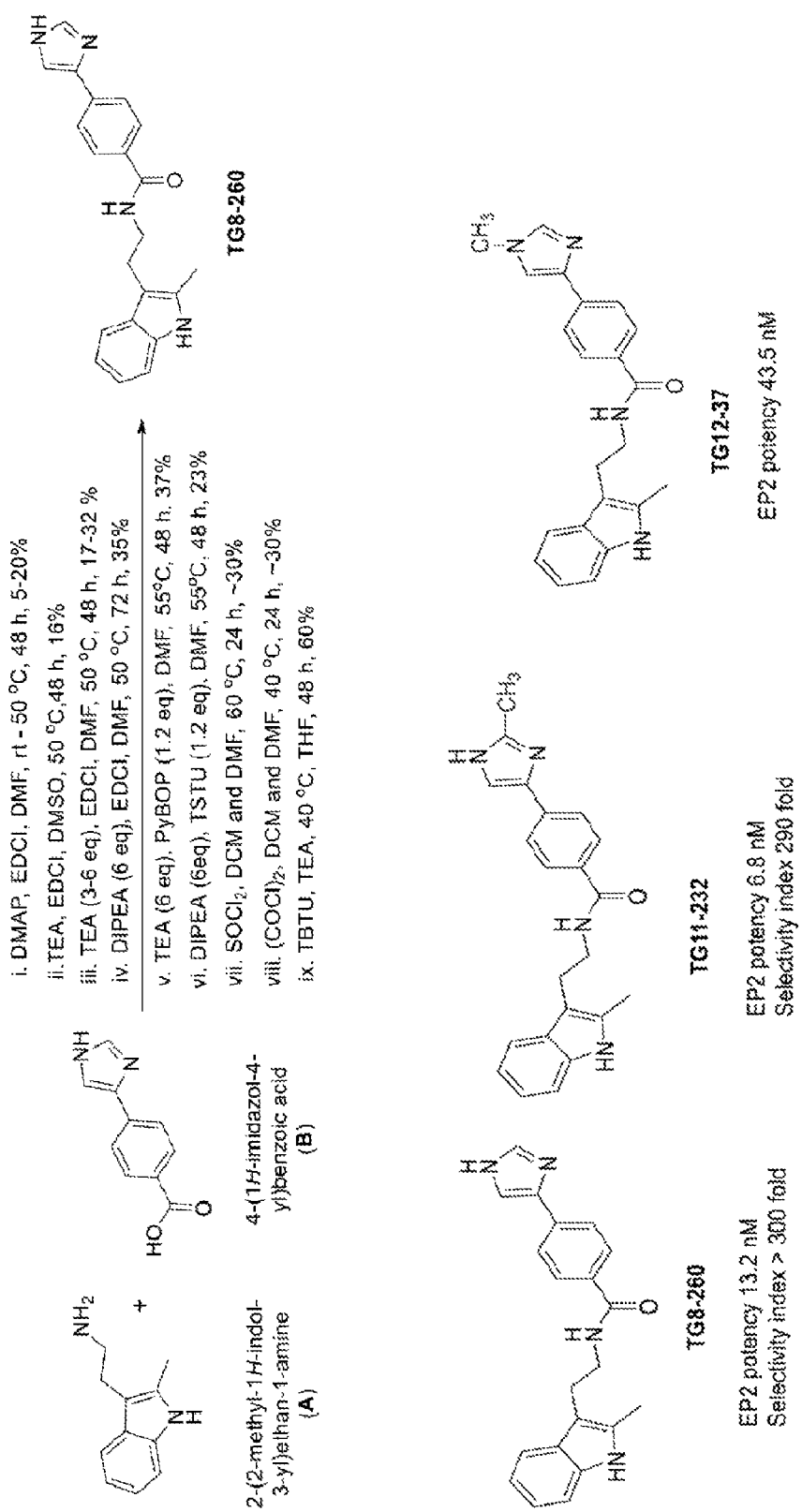
FIG. 4 illustrates the structures and synthesis of TG8-260 and derivatives. Initially TG8-260 was synthetized (<20% yield by method i., the yield improved to 60% (see method ix). TG11-232 and TG12-37 were synthesized using the methods provided TG8-260 with appropriately modified starting materials.
Figure 5A:
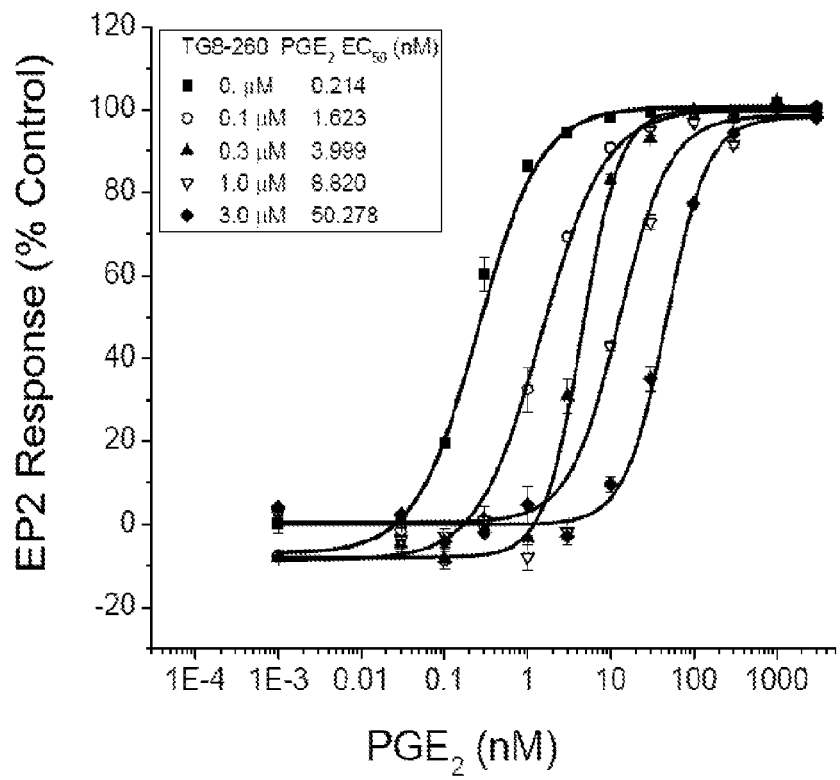
FIG. 5A shows data indicating TG8-260 inhibits PGE2-induced human EP2 receptor activation in a concentration dependent manner.
Figure 5B:
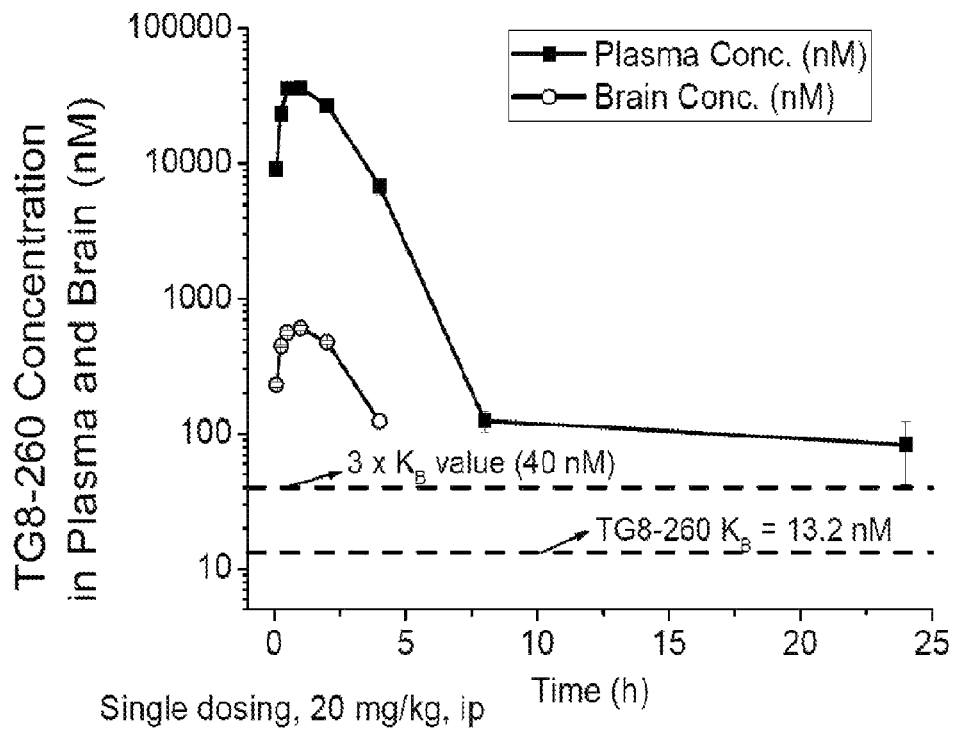
FIG. 5B shows data on pharmacokinetics in mice by single intraperitoneal (ip) injection indicated that TG8-260 remain in plasma until 24 h and in the brain until 4 h, at >3-fold higher concentration than the Schild KB value of the compound.
Figure 5C:
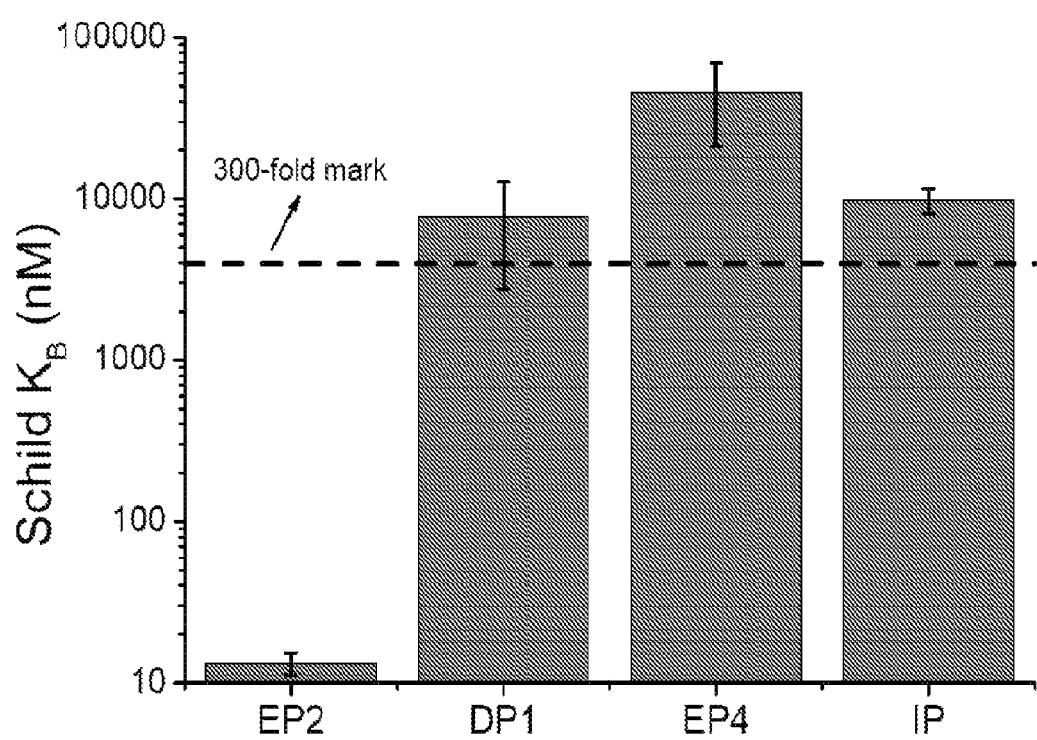
FIG. 5C shows data indicating selectivity potency of TG8-260 against DP1, EP4 and IP receptors indicates it is at least 300-fold selective to EP2 over these prostanoid receptors.
Figure 6B:
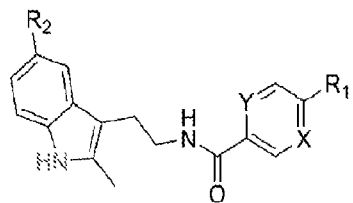
FIG. 6B shows data for additional compounds of this disclosure.
Figure 7:
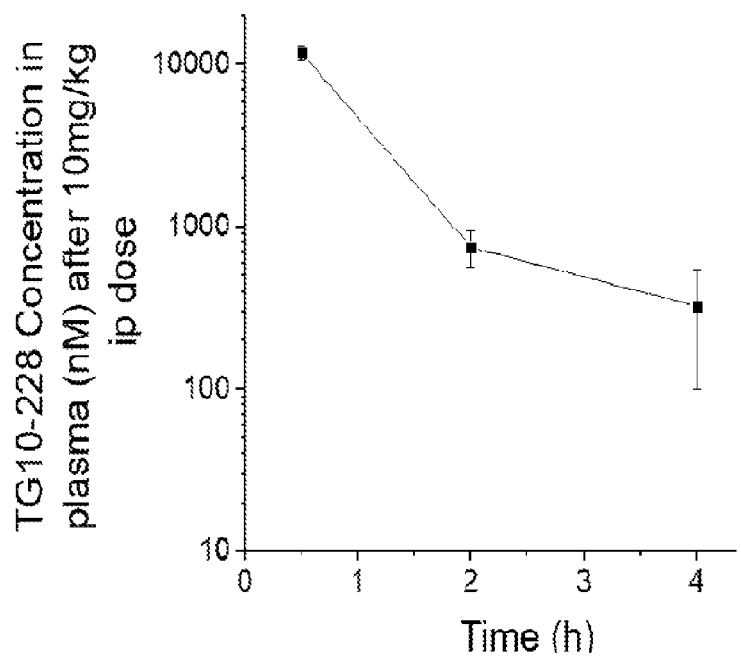
FIG. 7 shows data on vivo mouse plasma exposure of TG10-228.

TG11-77 HCl and a sister derivative TG11-283 HCl salt displayed superior (1.1-1.2 mg/mL) thermodynamic solubility in water relative to other derivatives, which showed <1 mg/mL water solubility. Initial pharmacokinetic analysis of the neutral compound TG11-77 indicated that it has a plasma half-life in mice of 2.4 hours, brain-to plasma ratio of about 0.4, and oral bioavailability 25%. Guided by this brain-to-plasma ratio and the water solubility of the salt, optimum dose finding studies for TG11-77 HCl salt were investigated with a continuous delivery method via drinking water at a projected dose of 100 mg/kg/day. A requisite drug concentration in plasma and the brain tissues were found. In the brain, 17-18 fold higher concentration was found compared to the potency of the compound (Schild KB=9.7 nM). The concentration in the plasma varied depending on the time of day (cf. 7 AM vs 12 noon, FIG. 3B), however, the concentration of drug in the brain is consistent in the morning and noon. The brain-to-plasma ratio (>0.46) at 12 noon by oral dosing is similar to the ratio found by single intraperitoneal injection of 10 mg/kg dose.

What is claimed is:

1. A compound having Formula III,

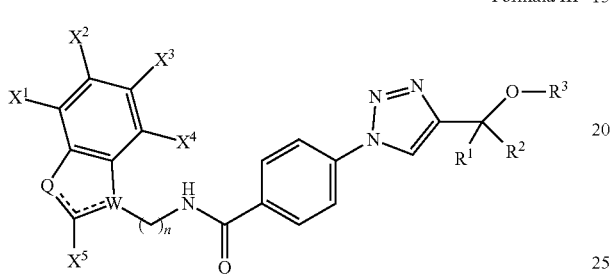

Formula III or pharmaceutically acceptable salt or prodrug thereof, wherein:
a dotted line represents a double or single bond,
n is 1, 2, 3, or 4;
Q is CH, N, or $NX^6$;
W is N or C;
$R^1$, $R^2$, and $R^3$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^1$, $R^2$, and $R^3$ are optionally substituted with one or more, the same or different, $R^{10}$;
$X^1$, $X^2$, $X^3$, and $X^4$ are each, the same or different, hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^1$, $X^2$, $X^3$, and $X^4$ are optionally substituted with one or more, the same or different, $X^{10}$;
$X^5$ and $X^6$ are each, the same or different, hydrogen or alkyl, wherein $X^5$ and $X^6$ are optionally substituted with one or more, the same or different, $X^{10}$;
$X^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $X^{10}$ is optionally substituted with one or more, the same or different, $X^{11}$;
$X^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;
$R^{10}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{10}$ is optionally substituted with one or more, the same or different, $R^{11}$;
$R^{11}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$; and
$R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

2. A compound 4-(4-(2-hydroxypropan-2-yl)-1H-1,2,3-triazol-1-yl)-N-(2-(2-methyl-1H-indol-3-yl)ethyl)benzamide or salt thereof.

* * * * *